United States Patent
Orkin et al.

(10) Patent No.: US 11,021,696 B2
(45) Date of Patent: Jun. 1, 2021

(54) NUCLEASE-MEDIATED REGULATION OF GENE EXPRESSION

(71) Applicants: Children's Medical Center Corporation, Boston, MA (US); Sangamo Therapeutics, Inc., Brisbane, CA (US)

(72) Inventors: Stuart H. Orkin, Boston, MA (US); Andreas Reik, Brisbane, CA (US); Fyodor Urnov, Brisbane, CA (US)

(73) Assignees: Children's Medical Center Corporation, Boston, MA (US); Sangamo Therapeutics, Inc., Brisbane, CA (US)

( * ) Notice: Subject to any disclaimer, the term of this patent is extended or adjusted under 35 U.S.C. 154(b) by 0 days.

(21) Appl. No.: 14/540,729

(22) Filed: Nov. 13, 2014

(65) Prior Publication Data
US 2015/0132269 A1    May 14, 2015

Related U.S. Application Data

(60) Provisional application No. 62/042,075, filed on Aug. 26, 2014, provisional application No. 61/903,823, filed on Nov. 13, 2013.

(51) Int. Cl.
| | |
|---|---|
| *A61K 48/00* | (2006.01) |
| *C07H 21/04* | (2006.01) |
| *C12N 15/63* | (2006.01) |
| *C12N 9/22* | (2006.01) |
| *C12N 15/85* | (2006.01) |
| *A61K 35/12* | (2015.01) |
| *C12N 15/113* | (2010.01) |
| *C07K 14/47* | (2006.01) |
| *A61K 38/46* | (2006.01) |
| *A61K 35/28* | (2015.01) |
| *A01K 67/00* | (2006.01) |

(52) U.S. Cl.
CPC ............... *C12N 9/22* (2013.01); *A61K 35/12* (2013.01); *A61K 35/28* (2013.01); *A61K 38/465* (2013.01); *C07K 14/4702* (2013.01); *C12N 15/113* (2013.01); *C12N 15/85* (2013.01); *A61K 48/00* (2013.01); *C07K 2319/81* (2013.01); *C12N 2310/10* (2013.01); *C12N 2310/20* (2017.05)

(58) Field of Classification Search
CPC ........ A61K 35/28; A61K 35/12; A61K 48/00; C07K 14/47; C12N 9/22; C12N 15/85; C12N 15/113
See application file for complete search history.

(56) References Cited

U.S. PATENT DOCUMENTS

| | | |
|---|---|---|
| 5,356,802 A | 10/1994 | Chandrasegaran |
| 5,420,032 A | 5/1995 | Marshall et al. |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas, III |
| 6,140,466 A | 10/2000 | Barbas, III et al. |
| 6,180,613 B1 | 1/2001 | Kaplitt et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenbarg et al. |
| 6,479,626 B1 | 11/2002 | Kim et al. |
| 6,503,717 B2 | 1/2003 | Case et al. |
| 6,503,888 B1 | 1/2003 | Kaplitt et al. |
| 6,534,261 B1 | 3/2003 | Cox et al. |
| 6,599,692 B1 | 6/2003 | Case et al. |
| 6,607,882 B1 | 8/2003 | Cox et al. |
| 6,689,558 B2 | 2/2004 | Case |
| 6,794,136 B1 | 9/2004 | Eisenberg et al. |
| 6,824,978 B1 | 11/2004 | Cox et al. |
| 6,832,252 B1 | 12/2004 | Cieslak et al. |
| 6,903,185 B2 | 6/2005 | Kim et al. |
| 6,933,113 B2 | 8/2005 | Case et al. |
| 6,979,539 B2 | 12/2005 | Cox et al. |
| 6,998,118 B2 | 2/2006 | Kaspar et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,074,596 B2 | 7/2006 | Darzynkiewicz et al. |
| 7,101,540 B2 | 10/2006 | Kaspar et al. |
| 7,153,949 B2 | 12/2006 | Kim et al. |
| 7,163,824 B2 | 1/2007 | Cox et al. |
| 7,253,273 B2 | 8/2007 | Collingwood |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Funnel et al , 2015, Blood 126:89-93.*

(Continued)

*Primary Examiner* — Quang Nguyen
(74) *Attorney, Agent, or Firm* — Lathrap GPM LLP; James H. Velema, Esq.

(57) ABSTRACT

The present disclosure is in the field of genome engineering, particularly targeted modification of the genome of a hematopoietic cell.

6 Claims, 22 Drawing Sheets

Specification includes a Sequence Listing.

(56) References Cited

U.S. PATENT DOCUMENTS

| | | |
|---|---|---|
| 7,262,054 B2 | 8/2007 | Jamieson et al. |
| 7,361,635 B2 | 4/2008 | Miller et al. |
| 7,629,326 B2 | 12/2009 | Choulika et al. |
| 7,837,668 B2 | 11/2010 | Gasmi et al. |
| 7,888,121 B2 | 2/2011 | Urnov et al. |
| 7,914,796 B2 | 3/2011 | Miller et al. |
| 7,951,925 B2 | 5/2011 | Ando et al. |
| 7,972,854 B2 | 7/2011 | Miller et al. |
| 8,034,598 B2 | 10/2011 | Miller et al. |
| 8,092,429 B2 | 1/2012 | Gasmi et al. |
| 8,110,379 B2 | 2/2012 | DeKelver et al. |
| 8,153,773 B2 | 4/2012 | Jemiility et al. |
| 8,409,861 B2 | 4/2013 | Gushin et al. |
| 8,586,526 B2 | 11/2013 | Gregory et al. |
| 8,623,618 B2 | 1/2014 | Doyon et al. |
| 8,772,453 B2 | 7/2014 | Paschon et al. |
| 8,921,332 B2 | 12/2014 | Choulika et al. |
| 2003/0104526 A1 | 6/2003 | Liu et al. |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2005/0267061 A1 | 12/2005 | Martin |
| 2006/0063231 A1 | 3/2006 | Li et al. |
| 2006/0188987 A1 | 8/2006 | Guschin |
| 2006/0239966 A1 | 10/2006 | Tornøe et al. |
| 2007/0117128 A1 | 5/2007 | Smith et al. |
| 2007/0141038 A1 | 6/2007 | Choulika et al. |
| 2007/0218528 A1 | 9/2007 | Miller |
| 2008/0131962 A1 | 6/2008 | Miller |
| 2008/0159996 A1 | 7/2008 | Ando et al. |
| 2008/0299580 A1 | 12/2008 | DeKelver et al. |
| 2009/0068164 A1 | 3/2009 | Segal et al. |
| 2009/0111188 A1 | 4/2009 | Cai et al. |
| 2009/0117617 A1 | 5/2009 | Holmes et al. |
| 2009/0305419 A1 | 12/2009 | Miller |
| 2010/0047805 A1 | 2/2010 | Wang |
| 2010/0218264 A1 | 8/2010 | Cui et al. |
| 2011/0027235 A1 | 2/2011 | Gregory et al. |
| 2011/0182867 A1 | 7/2011 | Orkin et al. |
| 2011/0201055 A1 | 8/2011 | Doyon et al. |
| 2011/0207221 A1 | 8/2011 | Cost et al. |
| 2011/0265198 A1 | 10/2011 | Gregory et al. |
| 2011/0301073 A1 | 12/2011 | Gregory et al. |
| 2012/0017290 A1 | 1/2012 | Cui et al. |
| 2012/0195936 A1 | 8/2012 | Rudolph et al. |
| 2012/0222143 A1* | 8/2012 | Fahrenkrug et al. |
| 2012/0230971 A1 | 10/2012 | Choulika et al. |
| 2012/0294826 A1* | 11/2012 | Spitalnik .............. A01N 1/0263 424/78.37 |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar |
| 2013/0326645 A1 | 12/2013 | Cost et al. |
| 2014/0093913 A1 | 4/2014 | Cost et al. |
| 2015/0056705 A1 | 2/2015 | Conway et al. |
| 2015/0064789 A1 | 3/2015 | Paschon et al. |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/46386 A3 | 2/2000 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/077277 A2 | 10/2002 |
| WO | WO 02/099084 A2 | 12/2002 |
| WO | WO 07/014275 A2 | 2/2007 |
| WO | WO 03/016496 A2 | 2/2008 |
| WO | WO 10/079430 A1 | 7/2010 |
| WO | WO2013/055985 A1 | 4/2013 |
| WO | WO2013/126794 A1 | 8/2013 |
| WO | WO2014/036219 A2 | 3/2014 |
| WO | WO2014/085593 A1 | 6/2014 |
| WO | WO2016/183298 A2 | 11/2016 |

OTHER PUBLICATIONS

Smith et al., 2016, Hum. Mol. Genet. 2016, 0:1-7.*
Glarneau et al, 2010, Nature Genetics 42:1049-1051.*
Uda et al., 2008, PNAS (USA) 105:1620-1625.*
Funnell et al 2015, Blood 126:89-93.*
USPTO-STIC Sequence Search Mar. 28, 2016, pp. 1-3.*
Xiao et al 2013 Nucleic Acids Res. 41:1-11.*
Osborn et al 2011, Human Gene Therapy 22:1155-1165.*
Gaj et al 2013, Trends in Biotechnology 7:397-405.*
Bauer et al. HbF-associated genetic variation marks an erythroid regulatory element essential for BCL11a transcription and subsequent stage-specific globin expression. Abstract 828 (1 page). Blood 120.21, American Society of Hematology, Nov. 16, 2012.*
Gaj et al. ZFN, TALEN, and CRISPR/Cas-based methods for genome engineering. Trends in Biotechnology 31:397-405, (Year: 2013).*
Niu et al. Applications of TALENs and CRISPR/Cas9 in human cells and their potentials for gene therapy. Mol. Biotechnol. 56:681-688, (Year: 2014).*
Chandrakasan et al. Gene therapy for hemoglobinopathies: The state of the field and the future. Hematol. Oncol. Clin. North Am. 28:199-216, (Year: 2014).*
Argast, et al., "I-PPOI and I-CREI Homing Site Sequence Degeneracy Determined by Random Mutagenesis and Sequential In Vitro Enrichment," *J. Mol. Biol.* 280:345-353 (1998).
Ashworth, et al., "Computational Redesign of Endonuclease DNA Binding and Cleavage Specificity," *Nature* 441:656-659 (2003).
Bauer, et al., "An Erythroid Enhancer of BCL11A Subject to Genetic Variation Determines Detal Homoglobin Level," *Science* 342(6155):253-257 (2013).
Beerli, et al., "Engineering Polydactyl Zinc-Finger Transcription Factors," *Nature Biotechnol* 20:135-141 (2002).
Belfort, et al., "Homing Endonucleases: Keeping the House in Order," *Nucleic Acids Research* 25:3379-3388 (1997).
Bitinaite, et al., "FOKI Dimerization Is Required for DNA Cleavage," *PNAS USA* 95:10570-10575 (1998).
Boch, et al., "Breaking the Code of DNA Binding Specificity of TAL-Type III Effectors," *Science* 326:1509-1512 (2009).
Bonas, et al., "Genetic and Structural Characterization of the Avirulence Gene AVRBS3 From Xanthomonas Campestris PV. Vesicatoria," *Mol. Gen. Genet.* 218:127-136 (1989).
Chevalier, et al., "Design, Activity, and Structure of a Highly Specific Artificial Endonuclease," *Molecular Cell* 10:895-905 (2002).
Choo, et al., "Advances in Zinc Finger Engineering," *Curr. Opin. Struct. Biol.* 10:411-416 (2000).
Christian, et al., "TAL Effector Nucleases Create Targeted DNA Double-Strand Breaks," *Genetics* epub 10.1534/genetics.110.120717 (2010).
Cong, et al., "Multiplex Genome Engineering Using CRISPR/CAS Systems," *Sciencexpress* 1/10.1126/science1231143 (2013).
Constantoulakis, et al., "Alpha-Amino-N-Butyric Acid Stimulates Fetal Hemoglobin in the Adult," *Blood* 72(6):1961-1967 (1988).
DeSimone, "5-Azacytidine Stimulates Fetal Hemoglobin Synthesis in Anemic Baboons," *PNAS USA* 79(14):4428-4431(1982).
Dujon, et al., "Mobile Introns: Definition of Terms and Recommended Nomenclature," *Gene* 82:115-118 (1989).
Epinat, et al., "A Novel Engineered Meganuclease Induces Homologous Recombination in Yeast and Mammalian Cells," *Nucleic Acids Research* 31(11):3252-2962 (2003) doi: 10.1093/nar/gkg375.
Fu, et al., "Improving CRISPR-CAS Nuclease Specificity Using Truncated Guide RNAS," *Nature Biotechnology* 32(3):279-284 (2014).

(56) References Cited

OTHER PUBLICATIONS

Fujiwara, et al., "Discovering Hematopoietic Mechanisms Through Genome-Wide Analysis of Gata Factor Chromatin Occupancy," *Molecular Cell* 36:667-681 (2009).
Giarratana, et al., "Proof of Principle for Transfusion of In Vitro—Generated Red Blood Cells," *Blood* 118(19):5071-5079 (2011).
Gimble, et al., "Substrate Recognition and Induced DNA Distortion by the PI-SCEI Endonuclease, An Enzyme Generated by Protein Splicing," *J. Mol. Biol.* 263:163-180 (1996).
Grossman, et al., "Successful Ex Vivo Gene Therapy Directed to Liver in a Patient With Familial Hypercholesterolaemia," *Nature Genetics* 6:335-341 (1994) doi:10.1038/ng0494-335.
Guo, et al., "Directed Evolution of an Enhanced and Highly Efficient FOKI Cleavage Domain for Zinc Finger Nucleases," *J. Mol. Biol.* 400(1):96-107 (2010) doi:10.1016/j.jmb.2010.04.060.
Guschin, et al., "A Rapid and General Assay for Monitoring Endogenous Gene Modification," *Methods Mol. Biol.* 649:247-256 (2010).
Haft, et al., "A Guild of 45 CRISPR-Associated (CAS) Protein Families and Multiple CRISPR/CAS Subtypes Exist in Prokaryotic Genomes," *PLoS Comput Biol.* 1:e60 (2005).
Heuer, et al., "Repeat Domain Diversity of AVRBS3-Like Genes in *Ralstonia solanacearum* Strains and Association With Host Preferences in the Field," *Appl. and Envir. Micro.* 73:4379-4384 (2007).
Ho, et al., "Pathogenic Infection of Macaca Nemestrina With a CCR5-Tropic Subtype-C Simian-Human Immunodeficiency Virus," *Retrovirology* 6:65 (2009).
Holt, et al., "Zinc Finger Nuclease-Mediated CCR5 Knockout Hematopoietic Stem Cell Transplantation Controls HIV-1 In Vivo," *Nat. Biotech.* 28(8):839-847 (2010) doi:10.1038/nbt.1663.
Isalan, et al., "A Rapid, Generally Applicable Method to Engineer Zinc Fingers Illustrated by Targeting the HIV-1 Promoter," *Nature Biotechnology* 19(7):656-660 (2001).
Jansen, et al., "Identification of Genes That Are Associated With DNA Repeats in Prokaryotes," *Molecular Microbiology* 43(6):1565-1575 (2002).
Jasin, et al., "Genetic Manipulation of Genomes With Rare-Cutting Endonucleases," *Trends Genet.* 12:224-228 (1996).
Karikó, et al., "Incorporation of Pseudouridine Into MRNA Yields Superior Nonimmunogenic Vector With Increased Translational Capacity and Biological Stability," Molecular Therapy 16(11):1833-1840 (2012).
Kay, et al., "A Bacterial Effector Acts as a Plant Transcription Factor and Induces a Cell Size Regulator," *Science* 318:648-651 (2007).
Kim, et al., "Chimeric Restriction Endonuclease," *PNAS USA* 91:883-887 (1994).
Kim, et al., "Insertion and Deletion Mutants of FOKI Restriction Endonuclease," *J. Biol. Chem.* 269:31978-31982 (1994).
Kim, et al., "Hybrid Restriction Enzymes: Zinc Finger Fusions to FOK I Cleavage Domain," *PNAS USA* 93(31:1156-1160 (1996).
Kormann, et al., "Expression of Therapeutic Proteins After Delivery of Chemically Modified MRNA in Mice," *Nature Biotechnology* 29(21:154-157 (2011).
Ley, et al., "5-Azacytidine Increases Gamma-Globin Synthesis and Reduces the Proportion of Dense Cells in Patients With Sickle Cell Anemia," *Blood* 62:370-380 (1982).
Ley, et al., "5-Azacytidine Selectively Increases γ-Globin Synthesis in a Patent With B+ Thalassemia," *N. Engl. J. Medicine* 307:1469-1475 (1982).
Li, et al., "Alteration of the Cleavage Distance of FOK I Restriction Endonuclease by Insertion Mutagenesis," *PNAS USA* 90:2764-2768 (1993).
Li, et al., "Functional Domains in FOK I Restriction Endonuclease," *PNAS USA* 89:4275-4279 (1992).
Liu, et al., "Functional Studies of BCL11A: Characterization of the Conserved BCL11A-XL Splice Variant and Its Interaction With BCL6 in Nuclear Paraspeckles of Germinal Center B Cells," *Molecular Cancer* 5:18 (2006).

Makarova, et al., "A DNA Repair System Specific for Thermophilic Archaea and Bacteria Predicted by Genomic Context Analysis," *Nucleic Acids Res.* 30:482-496 (2002).
Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biol. Direct* 1:7 (2006).
Mandal, et al., "Efficient Ablation of Genes in Human Hematopoietic Stem and Effector Cells Using CRISPR/CAS9," *Cell Stem Cell* 15:643-652 (2014).
Martin and Orkin, "Transcriptional Activation and DNA Binding by the Erythroid Factor GF-1/ NF-EL/ERYF 1," *Genes Div.* 4:1886-1898 (1990).
Maston, et al., "Transcriptional Regulatory Elements in the Human Genome," *Ann. Rev. Genome Hum. Genet.* 7:29-50 (2006).
May, et al., "DynamicAnalysisofGeneExpressionandGenome-Wide Transcription Factor Binding During Lineage Specification ofMultipotent Progenitors," Cell Stem Cell 13:1-15 (2013).
Miller, et al., "An Improved Zinc-Finger Nuclease Architecture for Highly Specific Genome Editing," *Nat. Biotechnol.* 25:778-785 (2007).
Miller, et al., "A Tale Nuclease Architecture for Efficient Genome Editing," *Nat. Biotechnol.* 1-8 (2011) doi:10.1038/nbt.1755.
Moscou, et al., "A Simple Cipher Governs DNA Recognition by TAL Effectors," *Science* 326:1501 (2009).
Olovnikov, et al., "Bacterial Argonaute Samples the Transcriptome to Identify Foreign DNA," *Mol. Cell.* 51:594 (2013).
Pabo, et al., "Design and Selection of Novel CYS2HIS2 Zinc Finger Proteins," *Ann. Rev. Biochem.* 70:313-340 (2001).
Paques, et al., "Meganucleases and DNA Double-Strand Break Induced Recombination: Persectives for Gene Therapy," *Current Gene Therapy* 7:49-66 (2007).
Perez, et al., "Establishment of HIV-1 Resistance in CD4+ T Cells by Genome Editing Using Zinc-Finger Nucleases," 26(7):808-816 (2008).
Perler, et al., "Protein Splicing Elements: Inteins and Exteins a Definition of Terms and Recommended Nomenclature," *Nucleic Acids Research* 22:1125-1127 (1994).
Peterson, et al., "Robust Suppression of ENV-SHIV Viremia in Macaca Nemestrina by 3-Drug Art Is Independent of Timing of Initiation During Chronic Infection," *J. Med. Primatol.* 42:237-246 (2013).
Sankaran, et al., "Human Fetal Hemoglobin Expression Is Regulated by the Developmental Stage-Specific Repressor BCL11A," *Science* 322:1839 (2008).
Schornack, et al., "Gene-For-Gene-Mediated Recognition of Nuclear-Targeted AVRBS3-Like Bacterial Effector Proteins," *J. Plant Physiol.* 163:256-272 (2006).
Segal, et al., "Custom DNA-Binding Proteins Come of Age: Polydactyl Zinc-Finger Proteins," *Curr. Opin. Biotechnol.* 12(6):632-637 (2001).
Sheng, et al., "Structure-Based Cleavage Mechanism of Thermus Thermophilus Argonaute DNA Guide Strand-Mediated DNA Target Cleavage," *PNAS USA* 11:652 (2014).
Swarts, et al., "Dna-Guided DNA Interference by a Prokaryotic Argonaute," *Nature* 507(7491):258-261 (2014).
Tebas, et al., "Gene Editing of CCR5 in Autologous CD4 T Cells of Persons Infected With HIV," *New Engl. J. Med.* 370(10):901 (2014).
Thein, et al., "Control of Fetal Hemoglobin: New Insights Emerging From Genomics and Clinical Implications," *Hum. Mol. Genet.* 18(R2):R216-R223 (2009).
Tijssen, et al., "Genome-Wide Analysis of Simultaneous GATA1/2, RUNX1, FLI1, and SCL Binding in Megakaryocytes Identifies Hematopoietic Regulators," *Developmental Cell* 20:597-609 (2011).
Tsai, et al., "Dimeric CRISPR RNA-Guided FOKI Nucleases for Highly Specific Genome Editing," *Nature Biotechnology* 32:569-576 (2014) doi: 10.1038/nbt.2908.
U.S. Appl. No. 60/118,669, filed Feb. 3, 1999.
Vogel, "Biochemistry. A Bacterial Seek-and-Destroy System for Foreign DNA," *Science* 344(6187):972-973 (2014) doi: 10.1126/science.1252962.
Yang, et al., "Purification, Cloning, and Characterization of the CEL I Nuclease," *Biochemistry* 39:3533-3541 (2000).

(56) References Cited

OTHER PUBLICATIONS

Yuan, et al., "Crystal Structure of a. Aeolicus Argonaute, a Site-Specific DNA-Guided Endoribonuclease, Provides Insights Into RISC-Mediated MRNA Cleavage," *Mol. Cell.* 19:405-419 (2005).

Bauer, "Supplementary Materials and Methods Supplementary Text, Figs. S1-S9, Tables S1-S6, References 39-55," 34 pages, www.ncbi.nlm.nih.gov/pmc/articles/PMC4018826/bin/NIHMS575314-supplement-Supplementary_Material.pdf (Retrieved on 201-03-06).

Reik, et al., "Targeted Gene Modification in Hematopoietic Stem Cells: A Potential Treatment or Thalassemia and Sickle Cell Anemia," Blood, American Society of Hematology, US, vol. 122, No. 21, p. 434 (Nov. 15, 2013).

Xu et al., "Identification of BC L11A Structure-Function Domains for Fetal Hemoglobin Silencing," Blood, American Society of Hematology, US, vol. 122, No. 21, p. 435 (Nov. 15, 2013).

* cited by examiner

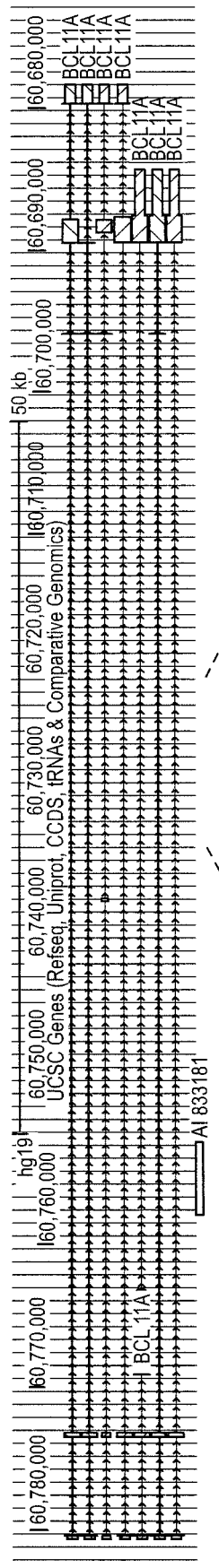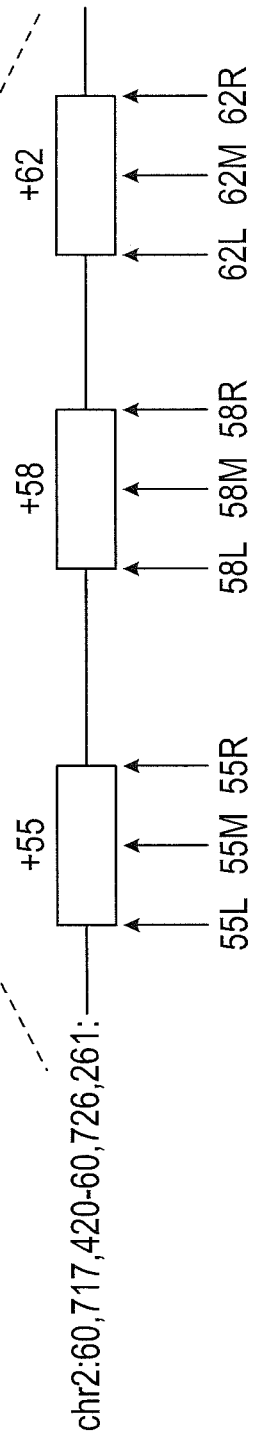
FIG. 2

| Lane | mRNA1 (SBS#) | mRNA2 (SBS#) | mRNA3 (SBS#) | mRNA4 (SBS#) | Deletion Size(bp) |
|---|---|---|---|---|---|
| | 55L | | 55R | | |
| 1 | 102783 | 102782 | - | - | |
| 2 | - | - | 102740 | 102741 | |
| 3 | 102783 | 102782 | 102740 | 102741 | 487 |
| 4 | GFP Transduction Control | | | | |
| | 62L | | 62R | | |
| 5 | 102795 | 102794 | - | - | |
| 6 | - | - | 102775 | 102774 | |
| 7 | 102795 | 102794 | 102775 | 102774 | 505 |
| 8 | GFP Transduction Control | | | | |
| | 58L | | 58R | | |
| 9 | 102750 | 102751 | 102756 | 102757 | 419 |
| 10 | GFP Transduction Control | | | | |
| 11 | 102750 | 102751 | 102756 | 102757 | |
| | 58M | | 58R | | |
| 12 | 102752 | 102753 | 102756 | 102757 | 219 |
| 13 | GFP Transduction Control | | | | |
| 14 | 102752 | 102753 | 102756 | 102757 | |

| Sample | TALEN Pair 1 (SBS#s) | | TALEN Pair 2 (SBS#s) | | Sample | TALEN Pair 1 (SBS#s) | | TALEN Pair 2 (SBS#s) | |
|---|---|---|---|---|---|---|---|---|---|
| 1 | 102831 | 102830 | | - | 15 | 102859 | 102858 | | - |
| 2 | 102833 | 102832 | | - | 16 | 102861 | 102860 | | - |
| 3 | 102835 | 102834 | | - | 17 | 102863 | 102862 | | - |
| 4 | 102837 | 102836 | | - | 18 | 102865 | 102864 | | - |
| 5 | 102839 | 102838 | | - | 19 | 102867 | 102866 | | - |
| 6 | 102841 | 102840 | | - | 20 | 102869 | 102868 | | - |
| 7 | 102843 | 102842 | | - | 21 | 102871 | 102870 | | - |
| 8 | 102845 | 102844 | | - | 22 | 102873 | 102872 | | - |
| 9 | 102847 | 102846 | | - | 23 | 102875 | 102874 | | - |
| 10 | 102849 | 102848 | | - | 24 | 102872 | 102873 | 102840 | 102841 |
| 11 | 102851 | 102850 | | - | 25 | 102860 | 102861 | 102840 | 102841 |
| 12 | 102853 | 102852 | | - | 26 | 102872 | 102873 | 102860 | 102861 |
| 13 | 102855 | 102854 | | - | 27 | GFP Transfection Control | | | |
| 14 | 102857 | 102856 | | - | | | | | |

FIG. 6
(Continued)

| Sample | ZFN Pair 1 (SBS#s) | | ZFN Pair 2 (SBS#s) | |
| --- | --- | --- | --- | --- |
| 1 | 45796 | 45795 | - | - |
| 2 | 45802 | 45800 | - | - |
| 3 | 45812 | 45811 | - | - |
| 4 | 45814 | 45813 | - | - |
| 5 | 45816 | 45815 | - | - |
| 6 | 45844 | 45843 | - | - |
| 7 | 45849 | 45848 | - | - |
| 8 | 45872 | 45871 | - | - |
| 9 | 45881 | 45880 | - | - |
| 10 | 45889 | 45888 | - | - |
| 11 | 45889 | 45888 | 45816 | 45815 |
| 12 | 45796 | 45795 | 45816 | 45915 |
| 13 | 45849 | 45795 | 45816 | 45815 |
| 14 | 45849 | 45848 | 45889 | 45888 |
| 15 | 45889 | 45888 | 45769 | 45795 |

| Sample | TALEN Pair (SBS#s) | | Sample | TALEN Pair (SBS#s) | |
|---|---|---|---|---|---|
| 1 | 102876 | 102877 | 12 | 102898 | 102899 |
| 2 | 102878 | 102879 | 13 | 102902 | 102903 |
| 3 | 102880 | 102881 | 14 | 102904 | 102905 |
| 4 | 102882 | 102883 | 15 | 102906 | 102907 |
| 5 | 102884 | 102885 | 16 | 102912 | 102913 |
| 6 | 102886 | 102887 | 17 | 102914 | 102915 |
| 7 | 102888 | 102889 | 18 | 102916 | 102917 |
| 8 | 102890 | 102891 | 19 | 102918 | 102919 |
| 9 | 102892 | 102893 | 20 | 102920 | 102921 |
| 10 | 102894 | 102895 | 21 | 102922 | 102923 |
| 11 | 102896 | 102897 | 22 | GFP Control | |

FIG. 9
(Continued)

+55 BCL11A Enhancer Sequence (SEQ ID No:1)

```
5'
caattctag gaagggaagt gggtatgggg cagcccattg ccttcctggt accaggatga
tgcaatgctt ggaggctgtg agctccccac cttctcaggg cacaccctgt gatcttgtgg
gaccctctg tccagcccag cctggtgtg catcttgtgt gcttggtcgg cactgatagg
ggtcgcggta gggagttgtc ggcacacact gctgcatgtc ctgtgagcgg tccccaaggc
tgtgccagc cttcagtgtc cagggcctct tctgacaggc cctgctggtt atcactgttg
gcattatctc cacgcaccac ttctgtgccc agggctgctg ggtcacctta aggagccaca
cacccgt 3'
```

FIG. 11A

+58 BCL11A Enhancer Sequence (SEQ ID No:2)

```
5' gagg tactgatgga ccttgggtgc tattcctgtg ataaggaagg cagctagaca
ggacttggga gttatctgta gtgagatggc tgaaaagcga tacagggctg gctctatgcc
ccaggtgtgc ataagtaaga gcagatagct gattccagtg caaagtccat acaggtaata
acataggcca gaaaagagat atggcatcta ctcttagaca taacacacca gggtcaatac
aactttgaag ctagtctagt gcaagctaac agttgctttt atcacacagct ccaggaaggg
tttggcctct gattagggtg ggggcgtggg tggggtagaa gaggactggc agacctctcc
atcggtggcc gtttgcccag ggggcctct ttcggaaggc tctcttggtg atggagaatt
ggattttatt tctcaatggg aatgaaataa tttgtatgcc atgccgtgtg gactcccaaa
attgtaaagg aggtgaagct tcccctgtct gcactctccc ctcctcataa ttgtccattt
ttcatctgtc gggctgtcc 3'
```

FIG. 11B

+62 BCL11A Enhancer Sequence (SEQ ID No:3)

```
5' cgtttttag aacttagctt tttgcattga ggatgcgcag gtggctgaga ctaacttctt
   tgcagatgac catggttgaa agtcagctat agagttgcac aaccacgtag ttgggcttca
   catagaag atgtgtcat tttttggtaa ctctgtcaga ctttaccaac ctggcgcaca
   gtctggttgg cacataaact tcacatttgc tcttctccag ggtgtggggt ggctgtttaa
   agagggtgga tattcatgct aatcttttgtg tagcataaca tgttactgca acttgctttt
   tttttttat ctgaaagttc aagtagatat cagaagggaa atgtttgtgg gtg 3'
```

FIG. 11C

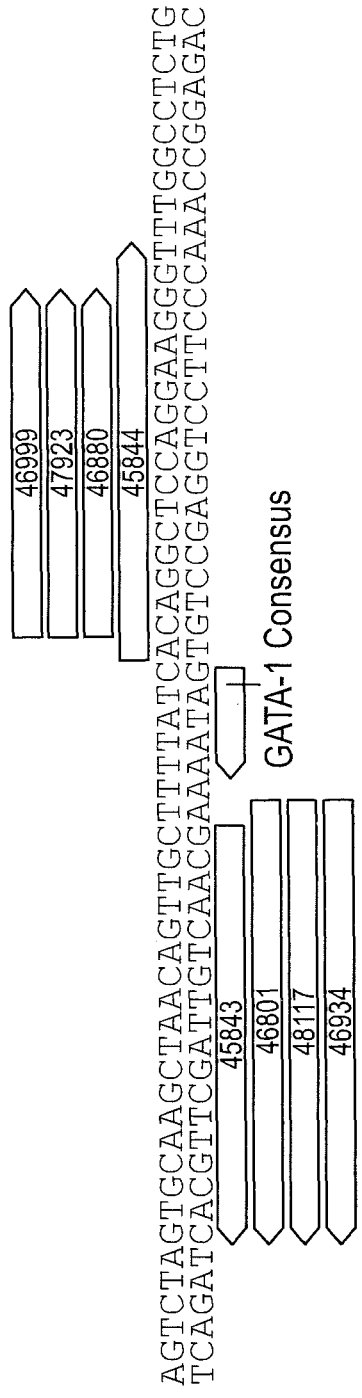

G  S  Q  L  V  K  S  E  L  E  E  K  (SEQ IN NO:256)
GGATCCCAGCTGGTGAAGAGCGAGCTGGAGGAGAAG (SEQ IN NO:257)

L7a

G  S  Q  L  V  K  S  K  S  E  A  A  A  R  E  L  E  E  K  (SEQ IN NO:258)
GGATCCCAGCTGGTGAAGAGCAAGAGCGAGGCCGCTGCCCGCGAGCTGGAGGAGAAG (SEQ IN NO:259)

L7c5

G  S  I  S  R  A  R  P  L  N  P  H  P  E  L  E  E  K  (SEQ IN NO:260)
GGATCCATCAGCAGAGCCAGACCACTGAACCCGCACCCGGAGCTGGAGGAGAAG (SEQ IN NO:261)

L8c4

G  S  Y  A  P  M  P  P  L  A  L  A  S  P  E  L  E  E  K  (SEQ IN NO:262)
GGATCCTACGCTCCAATGCCACCCCTGGCTCTGGCTTCCCCAGAGCTGGAGGAGAAG(SEQ IN NO:263)

FIG. 14

Linker name

```
L0  [+11]         LRGSQFVIPNRGVTKQLVKSELEEKKSEL
L0  [+9]          LRGS--VIPNRGVTKQLVKSELEEKKSEL
L0  [+7]          LRGS----PNRGVTKQLVKSELEEKKSEL
L0  [+5]          LRGS------RGVTKQLVKSELEEKKSEL
L0  [+3]          LRGS--------VTKQLVKSELEEKKSEL
L7a (+7)          LRGS----QLVKSKSEAAARELEEKKSEL
L8c4 (+7)         LRGS----YAPMPPLALASPELEEKKSEL
L7c5 (+6)         LRGS-----ISRARPLNPHPELEEKKSEL
L0                LRGS-----------QLVKSELEEKKSEL
L0  [-1]          LRGS-------------LVKSELEEKKSEL
L0  [-2]          LRGS--------------VKSELEEKKSEL
```

FIG. 17

NUCLEASE-MEDIATED REGULATION OF GENE EXPRESSION

CROSS-REFERENCE TO RELATED APPLICATIONS

The present application claims the benefit of U.S. Provisional Application No. 61/903,823, filed Nov. 13, 2013 and U.S. Provisional Application No. 62/042,075, filed Aug. 26, 2014, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Dec. 17, 2014, is named 83280112_SL.txt and is 58,663 bytes in size.

TECHNICAL FIELD

The present disclosure is in the field of genome engineering, particularly targeted modification of the genome of a hematopoietic cell.

BACKGROUND

When one considers that genome sequencing efforts have revealed that the human genome contains between 20,000 and 25,000 genes, but fewer than 2000 transcriptional regulators, it becomes clear that a number of factors must interact to control gene expression in all its various temporal, developmental and tissue specific manifestations. Expression of genes is controlled by a highly complex mixture of general and specific transcriptional regulators and expression can also be controlled by cis-acting DNA elements. These DNA elements comprise both local DNA elements such as the core promoter and its associated transcription factor binding sites as well as distal elements such as enhancers, silencers, insulators and locus control regions (LCRs) (see Maston et al (2006) *Ann Rev Genome Hum Genet* 7: 29-50).

Enhancer elements were first identified in the SV40 viral genome, and then found in the human immunoglobulin heavy chain locus. Now known to play regulatory roles in the expression of many genes, enhancers appear to mainly influence temporal and spatial patterns of gene expression. It has also been found that enhancers function in a manner that is not dependent upon distance from the core promoter of a gene, and is not dependent on any specific sequence orientation with respect to the promoter. Enhancers can be located several hundred kilobases upstream or downstream of a core promoter region, where they can be located in an intron sequence, or even beyond the 3' end of a gene.

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, e.g., U.S. Pat. Nos. 8,623,618; 8,034,598; 8,586,526; 6,534,261; 6,599,692; 6,503,717; 6,589,558; 7,067,317; 7,262,054; 7,888,121; 7,972,854; 7,914,796; 7,951,925; 8,110,379; 8,409,861; U.S. Patent Publications 20030232410; 20050208489; 20050026157; 20060063231; 20080159996; 201000218264; 20120017290; 20110265198; 20130137104; 20130122591; 20130177983; 20130177960 and 20150056705, the disclosures of which are incorporated by reference in their, entireties for all purposes. These methods often involve the use of engineered cleavage systems to induce a double strand break (DSB) or a nick in a target DNA sequence such that repair of the break by an error born process such as non-homologous end joining (NHEJ) or repair using a repair template (homology directed repair or HDR) can result in the knock out of a gene or the insertion of a sequence of interest (targeted integration). This technique can also be used to introduce site specific changes in the genome sequence through use of a donor oligonucleotide, including the introduction of specific deletions of genomic regions, or of specific point mutations or localized alterations (also known as gene correction). Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage. Further, targeted nucleases are being developed based on the Argonaute system (e.g., from *T. thermophilus*, known as 'TtAgo', see Swans et al (2014) *Nature* 507(7491): 258-261), which also may have the potential for uses in genome editing and gene therapy.

Red blood cells (RBCs), or erythrocytes, are the major cellular component of blood. In fact, RBCs account for one quarter of the cells in a human. Mature RBCs lack a nucleus and many other organelles in humans, and are full of hemoglobin, a metalloprotein that functions to carry oxygen to the tissues as well as carry carbon dioxide out of the tissues and back to the lungs for removal. This protein makes up approximately 97% of the dry weight of RBCs and it increases the oxygen carrying ability of blood by about seventy fold. Hemoglobin is a heterotetramer comprising two alpha ($\alpha$)-like globin chains and two beta ($\beta$)-like globin chains and 4 heme groups. In adults the $\alpha2\beta2$ tetramer is referred to as Hemoglobin A (HbA) or adult hemoglobin. Typically, the alpha and beta globin chains are synthesized in an approximate 1:1 ratio and this ratio seems to be critical in terms of hemoglobin and RBC stabilization. In a developing fetus, a different form of hemoglobin, fetal hemoglobin (HbF), is produced which has a higher binding affinity for oxygen than Hemoglobin A such that oxygen can be delivered to the baby's system via the mother's blood stream. Fetal hemoglobin also contains two $\alpha$ globin chains, but in place of the adult $\beta$-globin chains, it has two fetal gamma ($\gamma$)-globin chains (i.e., fetal hemoglobin is $\alpha2\gamma2$). At approximately 30 weeks of gestation, the synthesis of gamma globin in the fetus starts to drop while the production of beta globin increases. By approximately 10 months of age, the newborn's hemoglobin is nearly all $\alpha2\beta2$ although some HbF persists into adulthood (approximately 1-3% of total hemoglobin). The regulation of the switch from production of gamma- to beta-globin is quite complex, and primarily involves a down-regulation of gamma globin transcription with a simultaneous up-regulation of beta globin transcription.

Genetic defects in the sequences encoding the hemoglobin chains can be responsible for a number of diseases known as hemoglobinopathies, including sickle cell anemia and thalassemias. In the majority of patients with hemoglobinopathies, the genes encoding gamma globin remain present, but expression is relatively low due to normal gene repression occurring around parturition as described above.

It is estimated that 1 in 5000 people in the U.S. have sickle cell disease (SCD), mostly in people of sub-Saharan Africa descent. There appears to be a benefit for heterozygous carriers of the sickle cell mutation for protection against malaria, so this trait may have been positively selected over time, such that it is estimated that in sub-Saharan Africa, one third of the population has the sickle cell trait. Sickle cell disease is caused by a mutation in the β globin gene as a consequence of which valine is substituted for glutamic acid at amino acid #6 (a GAG to GTG at the DNA level), where the resultant hemoglobin is referred to as "hemoglobinS" or "HbS." Under lower oxygen conditions, a conformational shift in the deoxy form of HbS exposes a hydrophobic patch on the protein between the E and F helices. The hydrophobic residues of the valine at position 6 of the beta chain in hemoglobin are able to associate with the hydrophobic patch, causing HbS molecules to aggregate and form fibrous precipitates. These aggregates in turn cause the abnormality or 'sickling' of the RBCs, resulting in a loss of flexibility of the cells. The sickling RBCs are no longer able to squeeze into the capillary beds and can result in vaso-occlusive crisis in sickle cell patients. In addition, sickled RBCs are more fragile than normal RBCs, and tend towards hemolysis, eventually leading to anemia in the patient.

Treatment and management of sickle cell patients is a life-long proposition involving antibiotic treatment, pain management and transfusions during acute episodes. One approach is the use of hydroxyurea, which exerts its effects in part by increasing the production of gamma globin. Long term side effects of chronic hydroxyurea therapy are still unknown, however, and treatment gives unwanted side effects and can have variable efficacy from patient to patient. Despite an increase in the efficacy of sickle cell treatments, the life expectancy of patients is still only in the mid to late 50's and the associated morbidities of the disease have a profound impact on a patient's quality of life.

Thalassemias are also diseases relating to hemoglobin and typically involve a reduced expression of globin chains. This can occur through mutations in the regulatory regions of the genes or from a mutation in a globin coding sequence that results in reduced expression or reduced levels or functional globin protein. Alpha thalassemias are mainly associated with people of Western Africa and South Asian descent, and may confer malarial resistance. Beta thalassemia is mainly associated with people of Mediterranean descent, typically from Greece and the coastal areas of Turkey and Italy. Treatment of thalassemias usually involves blood transfusions and iron chelation therapy. Bone marrow transplants are also being used for treatment of people with severe thalassemias if an appropriate donor can be identified, but this procedure can have significant risks.

One approach that has been proposed for the treatment of both SCD and beta thalassemias is to increase the expression of gamma globin with the aim to have HbF functionally replace the aberrant adult hemoglobin. As mentioned above, treatment of SCD patients with hydroxyurea is thought to be successful in part due to its effect on increasing gamma globin expression. The first group of compounds discovered to affect gamma globin reactivation activity were cytotoxic drugs. The ability to cause de novo synthesis of gamma-globin by pharmacological manipulation was first shown using 5-azacytidine in experimental animals (DeSimone (1982) *Proc Nat'l Acad Sci USA* 79(14):4428-31). Subsequent studies confirmed the ability of 5-azacytidine to increase HbF in patients with β-thalassemia and sickle cell disease (Ley, et al., (1982) *N. Engl. J. Medicine,* 307: 1469-1475, and Ley, et al., (1983) *Blood* 62: 370-380). In addition, short chain fatty acids (e.g. butyrate and derivatives) have been shown in experimental systems to increase HbF (Constantoulakis et al., (1988) *Blood* 72(6):1961-1967). Also, there is a segment of the human population with a condition known as 'Hereditary Persistence of Fetal Hemoglobin' (HPFH) where elevated amounts of HbF persist in adulthood (10-40% in HPFH heterozygotes (see Thein et at (2009) *Hum. Mol. Genet* 18 (R2): R216-R223). This is a rare condition, but in the absence of any associated beta globin abnormalities, is not associated with any significant clinical manifestations, even when 100% of the individual's hemoglobin is HbF. When individuals that have a beta thalassemia also have co-incident HPFH, the expression of HbF can lessen the severity of the disease. Further, the severity of the natural course of sickle cell disease can vary significantly from patient to patient, and this variability, in part, can be traced to the fact that some individuals with milder disease express higher levels of HbF.

One approach to increase the expression of HbF involves identification of genes whose products play a role in the regulation of gamma globin expression. One such gene is BCL11A, first identified because of its role in lymphocyte development. BCL11A encodes a zinc finger protein that is thought to be involved in the developmental stage-specific regulation of gamma globin expression. BCL11A is expressed in adult erythroid precursor cells and down-regulation of its expression leads to an increase in gamma globin expression. In addition, it appears that the splicing of the BCL11A mRNA is developmentally regulated. In embryonic cells, it appears that the shorter BCL11A mRNA variants, known as BCL11A-S and BCL11A-XS are primary expressed, while in adult cells, the longer BCL11A-L and BCL11A-XL mRNA variants are predominantly expressed. See, Sankaran et at (2008) *Science* 322 p. 1839. The BCL11A protein appears to interact with the beta globin locus to alter its conformation and thus its expression at different developmental stages. Use of an inhibitory RNA targeted to the BCL11A gene has been proposed (see, e.g., U.S. Patent Publication 20110182867) but this technology has several potential drawbacks, namely that complete knock down may not be achieved, delivery of such RNAs may be problematic and the RNAs must be present continuously, requiring multiple treatments for life.

Targeting of BCL11A enhancer sequences may provide a mechanism for increasing HbF. For example, genome wide association studies have identified a set of genetic variations at BCL11A that are associated with increased HbF levels. These variations are a collection of SNPs found in non-coding regions of BCL11A that function as a stage-specific, lineage-restricted enhancer region. Further investigation revealed that this BCL11A enhancer is required in erythroid cells for BCL11A expression, but is not required for its expression in B cells (see Bauer et al, (2013) *Science* 343:253-257). The enhancer region was found within intron 2 of the BCL11A gene, and three areas of DNAseI hyper-sensitivity (often indicative of a chromatin state that is associated with regulatory potential) in intron 2 were identified. These three areas were identified as "+62", "+58" and "+55" in accordance with the distance in kilobases from the transcription start site of BCL11A. These enhancer regions are roughly 350 (+55); 550 (+58); and 350 (+62) nucleotides in length (Bauer 2013, ibid).

Thus, there remains a need for additional methods and compositions that can utilize these genome wide association studies for genome editing and the alteration of gene expression for example to treat hemoglobinopathies such as sickle cell disease and beta thalassemia.

SUMMARY

The present invention describes compositions and methods for use in gene therapy and genome engineering. Specifically, the methods and compositions described relate to inactivating (e.g., by completely or partially abolishing its expression) a gene, for example a gene that acts as regulator of one or more additional genes. In particular, the invention describes methods and compositions for interfering with enhancer function in a BCL11A gene to diminish or knock out its activity in specific cell lineages. Additionally, the invention provides methods and compositions for interfering with BCL11A enhancer functions wherein the enhancer sequences are not located within the BCL11A gene. The resulting down-regulation of the BCL11A gene in these circumstances in turn results in increased expression of gamma globin.

In some aspects, the invention comprises delivery of at least one nuclease (e.g., a nuclease that binds to a BCL11A enhancer sequence) to a human stem cell or precursor cell (HSC/PC) for the purpose of genome engineering. In certain embodiments, the nuclease recognizes a target sequence comprising at least 9 (e.g., 9, 10, 11, 12, 13, 14, 15, 16, 17, 18, 19, 20, 21 or even more) contiguous base pairs of SEQ ID NO:1, SEQ ID NO:2 or SEQ ID NO:3). Exemplary target sequences are shown in Tables 1, 2, 3, 4 and 6. In certain embodiments, the nuclease comprises a DNA-binding domain comprising A DNA-binding protein comprising a zinc finger protein comprising 4, 5 or 6 zinc finger domains comprising a recognition helix region, for example, the recognition helix regions in the order shown in a single row of Table 3 or Table 6. In other embodiments, the nuclease comprises a TALE protein comprising a plurality of TALE repeat units, each repeat unit comprising a hypervariable diresidue region (RVD), for example the RVDs of the TALE repeats units are shown in a single row of Table 1, Table 2 or Table 4. The nuclease(s) as described herein may further comprise a linker (e.g., between the DNA-binding domain and the cleavage domain), for example a linker as shown in FIGS. 14 and 17.

In some embodiments, the nuclease is delivered as a peptide, while in others it is delivered as a nucleic acid encoding the at least one nuclease. In some embodiments, more than one nuclease is used. In some preferred embodiments, the nucleic acid encoding the nuclease is an mRNA, and in some instances, the mRNA is protected. In some aspects, the mRNA may be chemically modified (See e.g. Kormann et al, (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication 2012-0195936). The nuclease may comprise a zinc finger nuclease (ZFN), a TALE-nuclease (TALEN) or a CRISPR/Cas nuclease system or a combination thereof. In a preferred embodiment, the nucleic acid encoding the nuclease(s) is delivered to the HSC/PC via electroporation. In some embodiments, the nuclease cleaves at or near the binding site of transcription factor. In some aspects, the transcription factor is GATA-1.

In some embodiments comprising a nuclease system that utilizes a nucleic acid guide (e.g. CRISPR/Cas; TtAgo), the cell can be contacted with the nucleic acid guide at the same time as it is contacted with the nuclease, prior to contact with the nuclease, or after contact with the nuclease. The cell can be contacted where the nuclease is provided as a polypeptide, a mRNA or an vector (including a viral vector) capable of expression of the gene encoding the nuclease. The guide nucleic acid maybe provided as an oligonucleotide (for TtAgo) or RNA (CRISPR/Cas). Further, guide RNA may be provided via an expression system for expression of the guide RNA within the cell. In some aspects, more than one guide RNA is provided (see Mandal et al (2014) *Cell Stem Cell* 15:643). In some embodiments, two guide RNAs are provided, while in others, more than two (e.g. three, four, five, six, seven, eight, nine, ten or more than ten) are provided. In some aspects, truncated guide RNAs are used to increase specificity (Fu et al (2014) *Nature Biotechnol* 32(3): 279). Also see U.S. Patent Publication No. 20150056705.

In one aspect, the invention comprises mutated Cas nucleases specific for a BCL11A enhancer. In some embodiments, these mutant Cas nucleases are Cas9 nucleases, and have altered functionality. In some embodiments, the Cas9 protein is mutated in the HNH domain, rendering it unable to cleave the DNA strand that is complementary to the guide RNA. In other embodiments, the Cas9 is mutated in the Rvu domain, making it incapable of cleaving the non-complimentary DNA strand. These mutations can result in the creation of Cas9 nickases. In some embodiments, two Cas nickases are used with two separate guide RNAs to target a DNA, which results in two nicks in the target DNA at a specified distance apart. In other embodiments, both the HNH and Rvu endonuclease domains are altered to render a Cas9 protein which is unable to cleave a target BCl11A enhancer DNA.

In another aspect, the methods and compositions of the invention comprise truncations of the Cas9 protein. In one embodiment, the Cas9 protein is truncated such that one or more of the Cas9 functional domains are removed. In one embodiment, the removal of part or one of the nuclease domains renders the Cas nuclease a nickase. In one embodiment, the Cas9 comprises only the domain responsible for interaction with the crRNA or sgRNA and the target DNA.

In still further aspects, the methods and compositions of the invention also comprise fusion proteins wherein the Cas9 protein, or truncation thereof, is fused to a functional domain. In some aspects, the functional domain is an activation or a repression domain. In other aspects, the functional domain is a nuclease domain. In some embodiments, the nuclease domain is a FokI endonuclease domain (e.g. Tsai (2014) *Nature Biotech* doi:10.1038/nbt.2908). In some embodiments, the FokI domain comprises mutations in the dimerization domain.

In other aspects, the invention comprises a cell or cell line in which an endogenous BCL11A enhancer sequence is modified, for example as compared to the wild-type sequence of the cell. The cell or cell lines may be heterozygous or homozygous for the modification. The modifications may comprise insertions, deletions and/or combinations thereof. In some preferred embodiments, the insertions, deletions and/or combinations thereof result in the destruction of a transcription factor binding site. In certain embodiments, the BCL11A enhancer sequence is modified by a nuclease (e.g., ZFN, TALEN, CRISPR/Cas system, Ttago system, etc.). In certain embodiments, the BCL11A enhancer is modified anywhere between exon 2 and exon 3. In other embodiments, the BCL11A enhancer is modified in the regions shown in SEQ ID NO:1, SEQ ID NO:2 or SEQ ID NO:3 (FIG. 11). In certain embodiments, the modification is at or near the nuclease(s) binding and/or cleavage site(s), for example, within 1-300 (or any value therebetween) base pairs upstream or downstream of the site(s) of cleavage, more preferably within 1-100 base pairs (or any value therebetween) of either side of the binding and/or cleavage site(s), even more preferably within 1 to 50 base pairs (or any value therebetween) on either side of the binding and/or cleavage site(s). In certain embodiments, the modification is at or near the "+58" region of the BCL11A enhancer, for example, at or near a nuclease binding site shown in any of SEQ ID NOs:4 to 80 and 276. In other embodiments, the modification is at or near the "+55" region of the BCL11A enhancer, for example, at or near a nuclease site shown in any of SEQ ID NOs:143 to 184 and 232-251. In still further embodiments, the modification occurs at other BCL11A enhancer sequences. Any cell or cell line may be modified, for example a stem cell (hematopoietic stem cell). Partially or fully differentiated cells descended from the modified stem cells as described herein are also provided (e.g., RBCs or RBC precursor cells). Any of the modified cells or cell lines disclosed herein may show increased expression of gamma globin. Compositions such as pharmaceutical compositions comprising the genetically modified cells as described herein are also provided.

In other aspects, the invention comprises delivery of a donor nucleic acid to a target cell. The donor may be delivered prior to, after, or along with the nucleic acid encoding the nuclease(s). The donor nucleic acid may comprise an exogenous sequence (transgene) to be integrated into the genome of the cell, for example, an endogenous locus. In some embodiments, the donor may comprise a full length gene or fragment thereof flanked by regions of homology with the targeted cleavage site. In some embodiments, the donor lacks homologous regions and is integrated into a target locus through homology independent mechanism (i.e. NHEJ). The donor may comprise any nucleic acid sequence, for example a nucleic acid that, when used as a substrate for homology-directed repair of the nuclease-induced double-strand break, leads to a donor-specified deletion to be generated at the endogenous chromosomal locus (e.g., BCL11A enhancer region) or, alternatively (or in addition to), novel allelic forms of (e.g., point mutations that ablate a transcription factor binding site) the endogenous locus to be created. In some aspects, the donor nucleic acid is an oligonucleotide wherein integration leads to a gene correction event, or a targeted deletion.

In other aspects, the nuclease and/or donor is(are) delivered by viral and/or non-viral gene transfer methods. In preferred embodiments, the donor is delivered to the cell via an adeno-associated virus (AAV). In some instances, the AAV comprises LTRs that are of a heterologous serotype in comparison with the capsid serotype.

In some aspects, the methods and compositions of the invention comprise one or more nucleases (e.g., ZFNs and/or TALENs) targeted to specific regions in the BCL11A enhancer region. In some embodiments, the one or more pairs of nucleases target sequences that result in the modification of the enhancer region by deletion of it in its entirety, while in other embodiments, subsections of the enhancer are deleted. In some embodiments, the deletion comprises one or more of the +55, +58 and/or +62 DNAseI hypersensitivity regions of the enhancer region. In other embodiments, a subset (less than all) of the hypersensitive regions is deleted. In some embodiments, only the +55, only the +58 or only the +62 region is deleted. In other embodiments, two of the regions are deleted (e.g., +55 and +58; +58 and +62; or +55 and +62).

In some aspects, deletions comprising regions within the DNAseI hypersensitive regions of the enhancer are made. These deletions can comprise from about 1 nucleotide to about 551 nucleotides. Thus, the deletions can comprise, 1, 5, 10, 15, 20, 25, 30, 40, 50, 100, 150, 200, 250, 300, 350, 400, 450, 500, 550 nucleotides, or any value therebetween. In some embodiments, the deletions comprise binding regions for one or more transcription factors. In some preferred embodiments, the deletions comprise a GATA-1 binding site, or the binding site for GATA-1 in combination with other factors.

Some aspects of the invention relate to engineered (non-natural) DNA binding proteins that bind to the BCL11A enhancer sequence(s) but do not cleave it. In some embodiments, the Cas9 nuclease domain in a CRISPR/Cas system can be specifically engineered to lose DNA cleavage activity ("dCAS"), and fused to a functional domain capable of modulating gene expression (see Perez-Pimera (2013) *Nat Method* 10(10):973-976) to create a CRISPR/dCas-TF. In some instances, the engineered DNA binding domains block interaction of the transcription factors active in enhancer activity from binding to their cognate enhancer sequences.

In some embodiments, the DNA binding domains are fused to a functional domain. Some aspects include fusion of the DNA binding domains with domains capable of regulating the expression of a gene. In some embodiments, the fusion proteins comprise a DNA binding domain (zinc finger, TALE, CRISPR/dCas, TtaGo or other DNA binding domains that can be engineered for binding specificity) fused to a gene expression modulatory domain where the modulator represses gene expression.

In some embodiments, the HSC/PC cells are contacted with the nucleases and/or DNA binding proteins of the invention. In some embodiments, the nucleases and/or DNA binding proteins are delivered as nucleic acids and in other embodiments, they are delivered as proteins. In some embodiments, the nucleic acids are mRNAs encoding the nucleases and/or DNA binding proteins, and in further embodiments, the mRNAs may be protected. In some embodiments, the mRNA may be chemically modified, may comprise an ARCA cap and/or may comprise a mixture of unmodified and modified nucleotides.

In some aspects, the HSC/PC are contacted with the nucleases and/or DNA binding proteins of the inventions ex vivo, following apheresis of the HSC/PC from a subject, or purification from harvested bone marrow. In some embodiments, the nucleases cause modifications within the BCL11A enhancer regions. In further embodiments, the HSC/PC containing the BCL11A enhancer region modifications are introduced back into the subject. In some instances, the HSC/PC containing the BCL11A enhancer region modifications are expanded prior to introduction. In other aspects, the genetically modified HSC/PC are given to the subject in a bone marrow transplant wherein the HSC/PC engraft, differentiate and mature in vivo. In some embodiments, the HSC/PC are isolated from the subject following G-CSF- and/or plerixafor-induced mobilization, and in others, the cells are isolated from human bone marrow or human umbilical cords. In some aspects, the subject is treated to a mild myeloablative procedure prior to introduction of the graft comprising the modified HSC/PC, while in other aspects, the subject is treated with a vigorous myeloablative conditioning regimen. In some embodiments, the methods and compositions of the invention are used to treat or prevent a hemoglobinopathy. In some aspects, the hemoglobinopathy is a beta thalassemia, while in other aspects, the hemoglobinopathy is sickle cell disease.

In some embodiments, the HSC/PC are further contacted with a donor molecule. In some embodiments, the donor molecule is delivered by a viral vector. The donor molecule may comprise one or more sequences encoding a functional polypeptide (e.g., a cDNA or fragment thereof), with or without a promoter. Additional sequences (coding or non-coding sequences) may be included when a donor molecule is used for inactivation, including but not limited to, sequences encoding a 2A peptide, SA site, IRES, etc.

In one aspect, the methods and compositions of the invention comprise methods for contacting the HSC/PC in vivo. The nucleases and/or DNA binding proteins are delivered to HSC/PC in situ by methods known in the art. In some embodiments, the nucleases and/or DNA binding proteins of the invention comprise a viral particle that is administered to the subject in need, while in others, the nucleases and/or DNA binding proteins comprise a nanoparticle (e.g. liposome). In some embodiments, the viral particles and/or nanoparticles are delivered to the organ (e.g. bone marrow) wherein the HSC/PC reside.

In another aspect, described herein are methods of integrating a donor nucleic acid into the genome of a cell via homology-independent mechanisms. The methods comprise creating a double-stranded break (DSB) in the genome of a cell and cleaving the donor molecule using a nuclease, such that the donor nucleic acid is integrated at the site of the DSB. In certain embodiments, the donor nucleic acid is integrated via non-homology dependent methods (e.g., NHEJ). As noted above, upon in vivo cleavage the donor sequences can be integrated in a targeted manner into the genome of a cell at the location of a DSB. The donor sequence can include one or more of the same target sites for one or more of the nucleases used to create the DSB. Thus, the donor sequence may be cleaved by one or more of the same nucleases used to cleave the endogenous gene into which integration is desired. In certain embodiments, the donor sequence includes different nuclease target sites from the nucleases used to induce the DSB. DSBs in the genome of the target cell may be created by any mechanism. In certain embodiments, the DSB is created by one or more zinc-finger nucleases (ZFNs), fusion proteins comprising a zinc finger binding domain, which is engineered to bind a sequence within the region of interest, and a cleavage domain or a cleavage half-domain. In other embodiments, the DSB is created by one or more TALE DNA-binding domains (naturally occurring or non-naturally occurring) fused to a nuclease domain (TALEN). In yet further embodiments, the DSB is created using a CRISPR/Cas nuclease system where an engineered single guide RNA or its functional equivalent is used to guide the nuclease to a targeted site in a genome.

In one aspect, the donor may encode a regulatory protein of interest (e.g. ZFP TFs, TALE TFs or a CRISPR/Cas TF) that binds to and/or modulates expression of a gene of interest. In one embodiment, the regulatory proteins bind to a DNA sequence and prevent binding of other regulatory factors. In another embodiment, the binding of a the regulatory protein may modulate (i.e. induce or repress) expression of a target DNA.

In some embodiments, the transgenic HSC/PC cell and/or animal includes a transgene that encodes a human gene. In some instances, the transgenic animal comprises a knock out at the endogenous locus corresponding to exogenous transgene, thereby allowing the development of an in vivo system where the human protein may be studied in isolation. Such transgenic models may be used for screening purposes to identify small molecules or large biomolecules or other entities which may interact with or modify the human protein of interest. In some aspects, the transgene is integrated into the selected locus (e.g., safe-harbor) into a stem cell (e.g., an embryonic stem cell, an induced pluripotent stem cell, a hematopoietic stem cell, etc.) or animal embryo obtained by any of the methods described herein, and then the embryo is implanted such that a live animal is born. The animal is then raised to sexual maturity and allowed to produce offspring wherein at least some of the offspring comprise edited endogenous gene sequence or the integrated transgene.

In another aspect, provided herein is a method of altering gene expression (e.g., BCL11a and/or a globin gene) in a cell, the method comprising: introducing, into the cell, one or more nucleases as described herein, under conditions such that the one or more proteins are expressed and expression of the gene is altered. In certain embodiments, expression of a globin gene (e.g., gamma globin or beta globin) is altered (e.g., increased). Any of the methods described herein may further comprise integrating a donor sequence (e.g., transgene or fragment thereof under the control of an exogenous or endogenous promoter) into the genome of the cell, for example integrating a donor at or near the site of nuclease cleavage in the BCL11a gene. The donor sequence is introduced to the cell using a viral vector, as an oligonucleotide and/or on a plasmid. The cell in which gene expression is altered may be, for example, a red blood cell (RBC) precursor cell and/or a hematopoietic stem cell (e.g., CD34+ cell).

In other embodiments, provided herein is a method of producing a genetically modified cell comprising a genomic modification within an endogenous BCL11a enhancer sequence, the method comprising the steps of: a) contacting a cell with a polynucleotide (e.g. DNA or mRNA) encoding a zinc finger nuclease comprising 4, 5, or 6 zinc finger domains in which each of the zinc finger domains comprises a recognition helix region in the order shown in a single row of Table 3 or Table 6; b) subjecting the cell to conditions conducive to expressing the zinc finger protein from the polynucleotide; and c) modifying the endogenous BCL11A enhancer sequence with the expressed zinc finger protein sufficient to produce the genetically modified cell. In certain embodiments, the cells are stimulated with at least one cytokine (e.g., prior to step (a)). The polynucleotide may be contacted with the cell using any suitable method, including but not limited, via transfection, using a non-viral vector, using a viral vector, by chemical means or by exposure to an electric field (e.g., electroporation).

Also provided is a method of treating a patient in need of an increase in globin gene expression, the method comprising administering to the patient the pharmaceutical preparation as described herein in an amount sufficient to increase the globin gene expression in the patient. In certain embodiments, the patient is known to have, is suspected of having, or is at risk of developing a thalassemia or sickle cell disease.

A kit, comprising the nucleic acids, proteins and/or cells of the invention, is also provided. The kit may comprise nucleic acids encoding the nucleases, (e.g. RNA molecules or ZFN, TALEN or CRISPR/Cas system encoding genes contained in a suitable expression vector), or aliquots of the nuclease proteins, donor molecules, suitable stemness modifiers, cells, buffers, and/or instructions (e.g., for performing the methods of the invention) and the like.

The invention therefore includes, but is not limited to the following embodiments:

1. A genetically modified cell comprising a genomic modification made by a nuclease, wherein the genomic modification is within an endogenous BCL11a enhancer sequence, and further wherein the genomic modification is selected from the group consisting of insertions, deletions and combinations thereof.

2. The genetically modified cell of embodiment 1, wherein the genomic modification is within one or more of the sequences shown in SEQ ID NO:1, 2 or 3.

3. The genetically modified cell of embodiment 2, wherein the genomic modification is within at least 9 contiguous base pairs of SEQ ID NO:1, 2 or 3.

4. The genetically modified cell of embodiment 2, wherein the genomic modification is within the +55 BCL11A enhancer sequence (SEQ ID NO:1).

5. The genetically modified cell of embodiment 4, wherein the genomic modification is at or near any of the sequences shown as SEQ ID Nos. 143 to 184 and 232-251.

6. The genetically modified cell of embodiment 2, wherein the genomic modification is within the +58 BCL11A enhancer sequence (SEQ ID NO:2).

7. The genetically modified cell of embodiment 6, wherein the genomic modification is at or near any of the sequences shown as SEQ ID Nos. 4 to 80 and 276.

8. The genetically modified cell of embodiment 2, wherein the genomic modification is within the +62 BCL11A enhancer sequence (SEQ ID NO:3)

9. The genetically modified cell of any of embodiments 1 to 8, wherein the cell is a stem cell.

10. The genetically modified cell of embodiment 9, wherein the stem cell is a hematopoietic stem cell.

11. The genetically modified cell of embodiment 10, wherein the hematopoietic stem cell is a CD34+ cell.

12. A genetically modified differentiated cell descended from the stem cell of any of embodiments 1 to 11.

13. The genetically modified cell of embodiment 12, wherein the cell is a red blood cell (RBC).

14. The genetically modified cell of any of embodiments 1 to 13, wherein the nuclease comprises at least one zinc finger nuclease (ZFN) or TALEN.

15. The genetically modified cell of any of embodiments 1 to 14, wherein the nuclease is introduced into the cell as a polynucleotide.

16. The genetically modified cell of any of embodiments 1 to 15, wherein the insertion comprises integration of a donor polynucleotide encoding a transgene.

17. The genetically modified cell of any of embodiments 14 to 16, wherein the nuclease comprises a zinc finger nuclease, the zinc finger nuclease comprising 4, 5, or 6 zinc finger domains comprising a recognition helix and further wherein the zinc finger proteins comprise the recognition helix regions in the order shown in a single row of Table 3 or Table 6.

18. The genetically modified cell of any of embodiments 14 to 16, wherein the nuclease comprises a TALEN, the TALEN comprising a plurality of TALE repeat units, each repeat unit comprising a hypervariable diresidue region (RVD), wherein the RVDs of the TALE repeats units are shown in a single row of Table 1, Table 2 or Table 4.

19. A pharmaceutical composition comprising the genetically modified cell of any of embodiments 1 to 18.

20. A DNA-binding protein comprising a zinc finger protein or a TALE-effector protein (TALE), wherein
  (i) the zinc finger protein comprises 4, 5 or 6 zinc finger domains comprising a recognition helix region, wherein the zinc finger proteins comprise the recognition helix regions in the order shown in a single row of Table 3 or Table 6; and
  (ii) the TALE protein comprising a plurality of TALE repeat units, each repeat unit comprising a hypervariable diresidue region (RVD), wherein the RVDs of the TALE repeats units are shown in a single row of Table 1, Table 2 or Table 4.

21. A fusion protein comprising a zinc finger protein or TALE protein of embodiment 20 and a wild-type or engineered cleavage domain or cleavage half-domain.

22. A polynucleotide encoding one or more proteins of embodiment 20 or embodiment 21.

23. An isolated cell comprising one or more proteins according to embodiment 20 or embodiment 21.

24. An isolated cell comprising one or more polynucleotides according to embodiment 22.

25. The cell of embodiment 23 or embodiment 24, wherein the cell is a hematopoietic stem cell.

26. A kit comprising at least one of: i) a polynucleotide encoding the protein according to embodiment 20 or embodiment 21 or ii) a protein according to embodiment 20 or embodiment 21.

27. A method of altering globin gene expression in a cell, the method comprising:
  introducing, into the cell, one or more polynucleotides according to embodiment 22, under conditions such that the one or more proteins are expressed and expression of the globin gene is altered.

28. The method of embodiment 27, wherein expression of the globin gene is increased.

29. The method of embodiment 27 or embodiment 28, wherein the globin gene is a gamma globin or beta globin gene.

30. The method of any of embodiments 27 to 29, further comprising integrating a donor sequence into the genome of the cell.

31. The method of embodiment 30, wherein the donor sequence is introduced to the cell using a viral vector, as an oligonucleotide or on a plasmid.

32. The method of any of embodiments 27 to 31, wherein the cell is selected from the group consisting of a red blood cell (RBC) precursor cell and a hematopoietic stem cell.

33. The method of any of embodiments 30 to 32, wherein the donor sequence comprises a transgene under the control of an endogenous or exogenous promoter.

34. A method of producing a genetically modified cell comprising a genomic modification within an endogenous BCL11a enhancer sequence, the method comprising the steps of:
  a) contacting a cell with a polynucleotide encoding a fusion protein comprising a zinc finger nuclease comprising 4, 5, or 6 zinc finger domains in which each of the zinc finger domains comprises a recognition helix region in the order shown in a single row of Table 3 or Table 6,
  b) subjecting the cell to conditions conducive to expressing the fusion protein from the polynucleotide; and
  c) modifying the endogenous BCL11A enhancer sequence with the expressed fusion protein sufficient to produce the genetically modified cell.

35. The method of embodiment 34, wherein the method further comprises stimulating the cells with at least one cytokine.

36. The method of embodiment 34 or embodiment 35, wherein the method further comprises the step of delivering the polynucleotide inside the cell.

37. The method of embodiment 36, wherein the delivery step comprises use of at least one of a non-viral delivery system, a viral delivery system, and a delivery vehicle.

38. The method of any of embodiments 34 to 37, wherein the delivery step further comprises subjecting the cells to an electric field.

39. A kit for performing the method of any of embodiments 34 to 37, the kit comprising:

a) at least one polynucleotide encoding a fusion protein comprising a zinc finger nuclease comprising 4, 5, or 6 zinc finger domains in which each of the zinc finger domains comprises a recognition helix region in the order shown in a single row of Table 3 or Table 6,
b) at least one polynucleotide encoding a TALE protein comprising a plurality of TALE repeat units, each repeat unit comprising a hypervariable diresidue region (RVD), wherein the RVDs of the TALE repeats units are shown in a single row of Table 1, Table 2 or Table 4; and optionally,
c) directions for using the kit.

40. A method of treating a patient in need of an increase in globin gene expression, the method comprising administering to the patient the pharmaceutical preparation of embodiment 19 in an amount sufficient to increase the globin gene expression in the patient.

41. The method of embodiment 40, wherein the patient is known to have, is suspected of having, or is at risk of developing a globinopathy.

42. The method of embodiment 41, wherein the globinopathy is a thalassemia or sickle cell disease.

43. The method of embodiment 42, wherein the thalassemia is β-thalassemia.

These and other aspects will be readily apparent to the skilled artisan in light of disclosure as a whole.

BRIEF DESCRIPTION OF THE DRAWINGS

FIG. 2 depicts the genomic region that encodes the various Bcl11a isoforms (University of California Santa Cruz genome browser, coordinates listed in the hg19 assembly of the human genome), the enhancer region in the BCL11A intron 2 (coordinates listed in the hg19 assembly of the human genome), and defines the three subregions of the enhancer region as represented by DNAse I hypersensitive sites (listed in kb by approximate distance from the transcription start site): +55, +58 and +62. Nuclease target locations within the three subregions are indicated as follows: nucleases were designed to cleave on the left end of each subregion (the 'L' sites), in the middle of each (the 'M' sites) and on the right end (the 'R' sites). Cleavage of the locus in vivo with a pair of nucleases results in a deletion of the intervening region in a significant fraction of the cells.

FIGS. 11A to 11C display the DNA sequence of the three DNAse I hypersensitive sites within the BCL11A enhancer sequence. Because their identification was performed by probing regions of accessible chromatin in cells (see Bauer et al, (2013) ibid), the exact boundaries of the regions are not known and approximate boundaries are shown. FIG. 11A shows the sequence of the +55 region (SEQ ID NO:1), FIG. 11B shows the sequence of the +58 region (SEQ ID NO:2) and FIG. 11C shows the sequence of the +62 region (SEQ ID NO:3).

FIGS. 12A to 12C demonstrate that ZFN-driven cleavage in cells closer to the core of the GATA-1 consensus elevates fetal globin levels to an even greater extent than cleavage closer to the 3' end of the motif. FIG. 12A displays a diagram depicting the binding sites of the Bcl11A-specific ZFN pairs in relation to the GATA-1 consensus sequence (FIG. 12A) and depicts a DNA sequence within the +58 region comprising the GATA-1 consensus sequence (SEQ ID NO:255). Bars above and below the DNA sequence indicate the binding sites of the ZFNs. FIG. 12B shows the relative expression of gamma globin and beta globin as measured by mRNA expression following of human HSPCs with mRNA encoding the indicated ZFNs (see FIG. 12A), followed by in vitro erythropoiesis and measurement of levels of fetal globin (see, FIG. 4). The ratio observed when a GFP expressing mRNA was transfected into the CD34+ cells was 0.97. FIG. 12C represents in "pie chart" form the allelic forms of the BCL11A enhancer (specifically, the region cleaved by the ZFNs shown in FIG. 12A) found in human HSPCs following electroporation with the indicated ZFNs. While comparable levels of unmodified (wild-type) chromatids are observed in the two samples, the sample treated with ZFNs that cut closer to the GATA-1 motif contain a greater number of chromatids that eliminate the GATA-1 consensus (e.g., the "−15" allele, which represents a deletion of 15 base pairs). The data demonstrates that cleavage by the two ZFN pairs that are closer to the center of the GATA-1 consensus sequence (pairs 46801/46880 and 46923/46999) is associated with increased gamma globin expression.

FIG. 14 depicts the amino acid and DNA sequences for four linkers (L0 (SEQ ID NO:256 and 257), L7a (SEQ ID NO:258 and 259), L7c5 (SEQ ID NO:260 and 261) and L8c5 (SEQ ID NO:262 and 263) used in the ZFP designs. Sequences with a solid underline indicate the carboxy terminal region of the ZFP DNA binding domain, while sequences indicated with the dashed underline indicate the amino terminal region of the Fok I nuclease domain. Sequences in bold indicate the novel sequences added to the standard L0 linker.

FIG. 15A is a graph depicting the percent human cells in the mouse periphery following transplantation of human CD34+ cells that had been edited with two different sets of ZFN 4 weeks post-transplant. FIG. 15B depicts the level of indels detected in those human cells. Each symbol represents data obtained from an individual mouse.

FIG. 16A shows the level of indel activity in pan-myeloid cells, identified by the presence of the CD33 marker. FIG. 16B shows the activity in CD19+ B cells. FIG. 16C shows the activity in glyA+ or erythroid cells, while FIG. 16D shows the activity in stem cells. Each symbol represents data obtained from an individual mouse.

FIG. 17 shows a series of linker sequences (SEQ ID NOS 265-275, respectively, in order of appearance). These linkers can serve to link the zinc finger DNA binding domain to the Fok1 nuclease domain.

DETAILED DESCRIPTION

Figure 1:
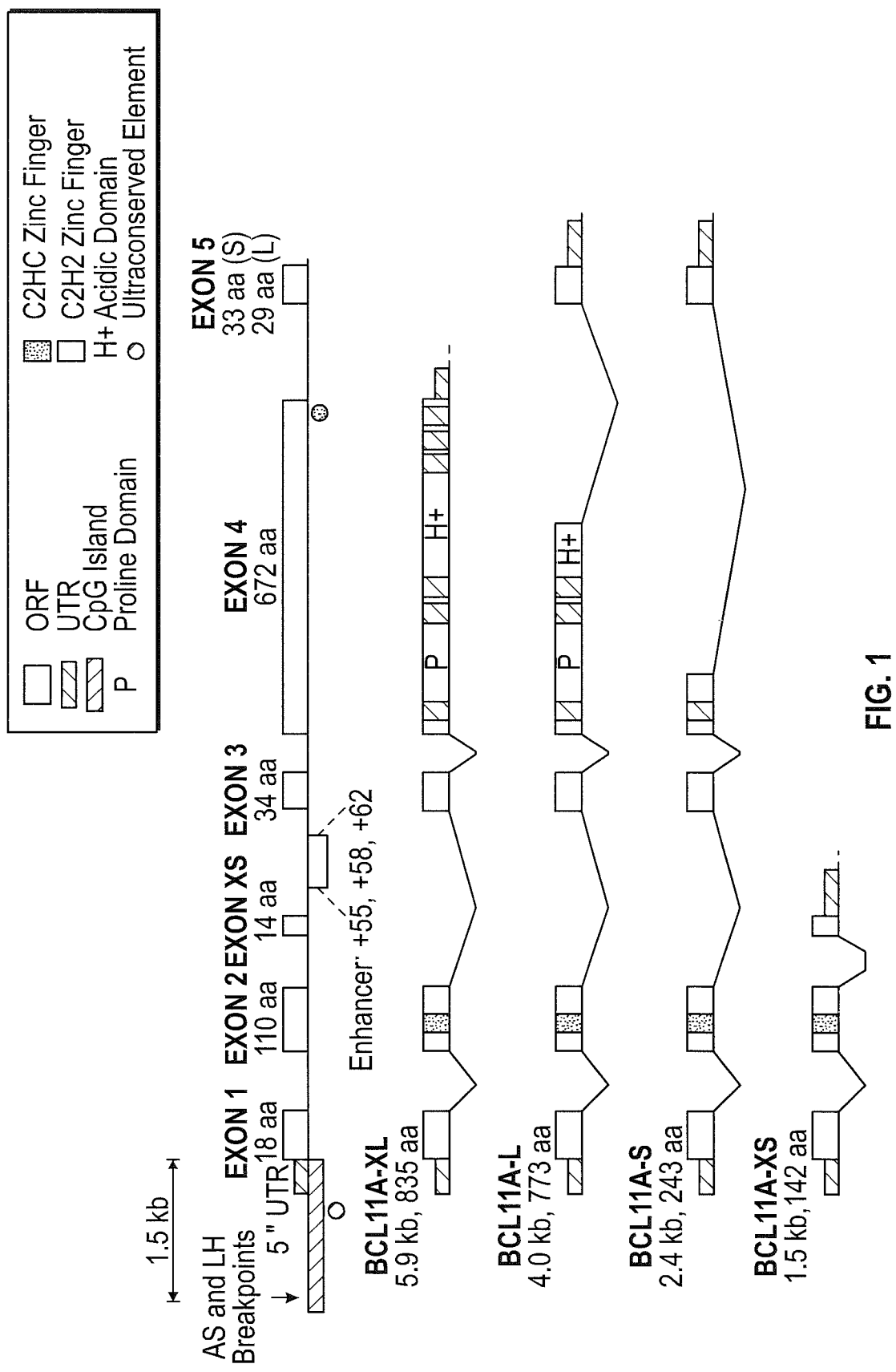
FIG. 1 depicts a diagram of the BCL11A coding region, indicating the position of the introns and of the enhancer regions. The derivations of the differing splicing products are also indicated (see Liu et al. (2006) *Molecular Cancer* 5:18).

Disclosed herein are compositions and methods for genome engineering for the modulation of BCL11A and/or gamma globin expression and for the treatment and/or prevention of hemoglobinopathies. In particular, nuclease-mediated (i.e. ZFN, TALEN or CRISPR/Cas or TtAgo system) targeted deletion of specific sites in a BCL11A enhancer region is efficiently achieved in HSC/PC and results in a change in relative gamma globin expression during subsequent erythropoiesis. This modulation of BCL11A and gamma globin expression is particularly useful for treatment of hemoglobinopathies (e.g., beta thalassemias, sickle cell disease) wherein there is insufficient beta globin expression or expression of a mutated form of beta-globin. Using the methods and compositions of the invention, the complications and disease related sequelae caused by the aberrant beta globin can be overcome by alteration of the expression of gamma globin in erythrocyte precursor cells.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P.M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ M$^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; 6,534,261 and 8,585,526; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; 8,586,526; WO 95/19431; WO 96/06166; WO 98/53057; WO 98/54311; WO 00/27878; WO 01/60970 WO 01/88197, WO 02/099084.

"TtAgo" is a prokaryotic Argonaute protein thought to be involved in gene silencing. TtAgo is derived from the bacteria *Thermus thermophilus*. See, e.g., Swarts et al, ibid, G. Sheng et al., (2013) *Proc. Natl. Acad. Sci. U.S.A.* 111, 652). A "TtAgo system" is all the components required including, for example, guide DNAs for cleavage by a TtAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break (DSB) in the target sequence (e.g., cellular chromatin) at a predetermined site. The DSB may result in deletions and/or insertions by homology-directed repair or by non-homology-directed repair mechanisms. Deletions may include any number of base pairs. Similarly, insertions may include any number of base pairs including, for example, integration of a "donor" polynucleotide, optionally having homology to the nucleotide sequence in the region of the break. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins or TALEN can be used for additional double-stranded cleavage of additional target sites within the cell.

Any of the methods described herein can be used for insertion of a donor of any size and/or partial or complete inactivation of one or more target sequences in a cell by targeted integration of donor sequence that disrupts expression of the gene(s) of interest. Cell lines with partially or completely inactivated genes are also provided.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528, 20080131962 and 20110201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS™), *Agrobacterium*-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE or CRISPR/Cas system as described herein. Thus, gene inactivation may be partial or complete.

A "protected" mRNA is one in which the mRNA has been altered in some manner to increase the stability or translation of the mRNA. Examples of protections include the use of replacement of up to 25% of the cytodine and uridine residues with 2-thiouridine (s2U) and 5-methylcytidine (m5C). The resulting mRNA exhibits less immunogenicity and more stability as compared with its unmodified counterpart. (see Karikó et al. ((2012), *Molecular Therapy*, Vol.

16, No. 11, pages 1833-1844). Other changes include the addition of a so-called ARCA cap, which increases the translationability of the in vitro produced mRNA (see U.S. Pat. No. 7,074,596).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE or Cas DNA-binding domain is fused to an activation domain, the ZFP, TALE or Cas DNA-binding domain and the activation domain are in operative linkage if, in the fusion polypeptide, the ZFP, TALE of Cas DNA-binding domain portion is able to bind its target site and/or its binding site, while the activation domain is able to upregulate gene expression. When a fusion polypeptide in which a ZFP, TALE or Cas DNA-binding domain is fused to a cleavage domain, the ZFP, TALE or Cas DNA-binding domain and the cleavage domain are in operative linkage if, in the fusion polypeptide, the ZFP, TALE or Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions.

Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the or stem cells of the invention can be administered. Subjects of the present invention include those that have been exposed to one or more chemical toxins, including, for example, a nerve toxin.

"Stemness" refers to the relative ability of any cell to act in a stem cell-like manner, i.e., the degree of toti-, pluri-, or oligopotentcy and expanded or indefinite self-renewal that any particular stem cell may have.

Nucleases

Described herein are compositions, particularly nucleases, that are useful for in vivo cleavage of a donor molecule carrying a transgene and nucleases for cleavage of the genome of a cell such that the transgene is integrated into the genome in a targeted manner. In certain embodiments, one or more of the nucleases are naturally occurring. In other embodiments, one or more of the nucleases are non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains).

A. DNA-Binding Domains

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG (SEQ ID NO: 287) family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI,I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene*

82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue.

In certain embodiments, the methods and compositions described herein make use of a nuclease that comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue. In addition, the DNA-binding specificity of homing endonucleases and meganucleases can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus Xanthomonas are known to cause many diseases in important crop plants. Pathogenicity of Xanthomonas depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et at (2007) Science 318:648-651). These proteins contain a DNA binding domain and a transcriptional activation domain. One of the most well characterized TAL-effectors is AvrBs3 from Xanthomonas campestgris pv. Vesicatoria (see Bonas et at (1989) Mol Gen Genet 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et at (2006) J Plant Physiol 163(3): 256-272). In addition, in the phytopathogenic bacteria Ralstonia solanacearum two genes, designated brg11 and hpx17 have been found that are homologous to the AvrBs3 family of Xanthomonas in the R. solanacearum biovar 1 strain GMI1000 and in the biovar 4 strain RS1000 (See Heuer et at (2007) Appl and Envir Micro 73(13): 4379-4384). These genes are 98.9% identical in nucleotide sequence to each other but differ by a deletion of 1,575 base pairs in the repeat domain of hpx17. However, both gene products have less than 40% sequence identity with AvrBs3 family proteins of Xanthomonas. See, e.g., U.S. Pat. No. 8,586,526, incorporated by reference in its entirety herein.

Specificity of these TAL effectors depends on the sequences found in the tandem repeats. The repeated sequence comprises approximately 102 base pairs (bp) and the repeats are typically 91-100% homologous with each other (Bonas et al, ibid). Polymorphism of the repeats is usually located at positions 12 and 13 and there appears to be a one-to-one correspondence between the identity of the hypervariable diresidues (RVD) at positions 12 and 13 with the identity of the contiguous nucleotides in the TAL-effector's target sequence (see Moscou and Bogdanove, (2009) Science 326:1501 and Boch et at (2009) Science 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target). See, e.g., U.S. Pat. No. 8,586,526; Christian et at ((2010)<Genetics epub 10.1534/genetics. 110.120717). In certain embodiments, TALE domain comprises an N-cap and/or C-cap as described in U.S. Pat. No. 8,586,526.

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

Nearly any linker (spacer) may be used between one or more of the components of the DNA-binding domain (e.g., zinc fingers), between one or more DNA binding domains and/or between the DNA-binding domain and the functional domain (e.g. nuclease). Non-limiting examples of suitable linker sequences include U.S. Pat. Nos. 8,772,453; 7,888, 121; 6,479,626; 6,903,185; and 7,153,949; U.S. Publication Nos. 20090305419 and 20150064789. Thus, the proteins described herein may include any combination of suitable linkers between the individual DNA-binding components and/or between the DNA-binding domain and the functional domain of the compositions described herein.

The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov, et al. (2013) *Mol. Cell* 51, 594; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37 degrees Celsius. Ago-RNA-mediated DNA cleavage could be used to affect a panopoly of outcomes including gene knock-out, targeted gene addition, gene correction, targeted gene deletion using techniques standard in the art for exploitation of DNA breaks.

Thus, the nuclease comprises a DNA-binding domain in that specifically binds to a target site in any gene into which it is desired to insert a donor (transgene).

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Nat'l Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014275. Likewise, TALE DNA-binding domains have been fused to nuclease domains to create TALENs. See, e.g., U.S. Publication No. 20110301073.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in See, e.g., U.S. Pat. Nos. 7,914,796; 8,034,598 and 8,623,618, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively. See, e.g., U.S. Pat. Nos. 7,914,796; 8,034,598 and 8,623,618. In other embodiments, the engineered cleavage half domain comprises the "Sharkey" and/or "Sharkey"' mutations (see Guo et al, (2010) *J. Mol. Biol.* 400(1):96-107).

Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see, e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164.

Nuclease expression constructs can be readily designed using methods known in the art. See, e.g., United States Patent Publications 20030232410; 20050208489; 20050026157; 20050064474; 20060188987; 20060063231; and International Publication WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek ibid and Cong, ibid).

Target Sites

As described in detail above, DNA domains can be engineered to bind to any sequence of choice. An engineered DNA-binding domain can have a novel binding specificity, compared to a naturally-occurring DNA-binding domain. In certain embodiments, the DNA-binding domains bind to a sequence within a BCL11A enhancer sequence, for example a target site (typically 9, 10, 11, 12, 13, 14, 15, 16, 17, 18, 19, 20, 21 or even more base pairs) is between exon 2 and exon 3 of BCL11A, including DNA-binding domains that bind to a sequence within a DNAseI hypersensitive site in the BCL11A enhancer sequence (e.g., +55, +58, +62; see FIG. 11). Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Publication No. 20110301073.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) and/or fusions of DNA-binding domain(s) and functional domain(s) may be linked, together using any suitable linker sequences, including for example, linkers of 5 or more amino acids. U.S. Pat. Nos. 8,772,453; 7,888,121 (e.g., "ZC" Linker); 6,479,626; 6,903,185; and 7,153,949; U.S.

Publication Nos. 20090305419 and 20150064789. The proteins described herein may include any combination of suitable linkers between the individual DNA-binding domains of the protein. See, also, U.S. Pat. No. 8,586,526.

Donors

In certain embodiments, the present disclosure relates to nuclease-mediated targeted integration of an exogenous sequence into the genome of a cell using the BCL11A enhancer region-binding molecules described herein. As noted above, insertion of an exogenous sequence (also called a "donor sequence" or "donor" or "transgene"), for example for deletion of a specified region and/or correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest or can be integrated via non-homology directed repair mechanisms. Additionally, donor sequences can comprise a vector molecule containing sequences that are not homologous to the region of interest in cellular chromatin. A donor molecule can contain several, discontinuous regions of homology to cellular chromatin, and, for example, lead to a deletion of a Bcl11a enhancer region (or a fragment thereof) when used as a substrate for repair of a DBS induced by one of the nucleases described here. Further, for targeted insertion of sequences not normally present in a region of interest, said sequences can be present in a donor nucleic acid molecule and flanked by regions of homology to sequence in the region of interest.

Polynucleotides for insertion can also be referred to as "exogenous" polynucleotides, "donor" polynucleotides or molecules or "transgenes." The donor polynucleotide can be DNA or RNA, single-stranded and/or double-stranded and can be introduced into a cell in linear or circular form. See, e.g., U.S. Patent Publication Nos. 20100047805 and 20110207221. The donor sequence(s) are preferably contained within a DNA MC, which may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. If introduced in double-stranded form, the donor may include one or more nuclease target sites, for example, nuclease target sites flanking the transgene to be integrated into the cell's genome. See, e.g., U.S. Patent Publication No. 20130326645.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

In certain embodiments, the double-stranded donor includes sequences (e.g., coding sequences, also referred to as transgenes) greater than 1 kb in length, for example between 2 and 200 kb, between 2 and 10 kb (or any value therebetween). The double-stranded donor also includes at least one nuclease target site, for example. In certain embodiments, the donor includes at least 2 target sites, for example for a pair of ZFNs or TALENs. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor is generally inserted so that its expression is driven by the endogenous promoter at the integration site, namely the promoter that drives expression of the endogenous gene into which the donor is inserted (e.g., globin, AAVS1, etc.). However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. In other embodiments, the transgene (e.g., with or without globin encoding sequences) is integrated into any endogenous locus, for example a safe-harbor locus. See, e.g., US patent publications 20080299580; 20080159996 and 201000218264.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The double-stranded donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the exogenous sequence (transgene) comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

For example, the exogenous sequence may comprise a sequence encoding a polypeptide that is lacking or nonfunctional in the subject having a genetic disease, including but not limited to any of the following genetic diseases: achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasiaossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted integration include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Additional gene sequences that can be inserted may include, for example, wild-type genes to replace mutated sequences. For example, a wild-type Factor IX gene sequence may be inserted into the genome of a stem cell in which the endogenous copy of the gene is mutated. The wild-type copy may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Delivery

The nucleases, polynucleotides encoding these nucleases, donor polynucleotides and compositions comprising the proteins and/or polynucleotides described herein may be delivered in vivo or ex vivo by any suitable means into any cell type.

Suitable cells include eukaryotic (e.g., animal) and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodopterafugiperda* (Sf), or fungal cells such as *Saccharomyces, Pichia* and *Schizosaccharomyces*. In certain embodiments, the cell line is a CHO, MDCK or HEK293 cell line. Suitable cells also include stem cells such as, by way of example, embryonic stem cells, induced pluripotent stem cells, hematopoietic stem cells, neuronal stem cells and mesenchymal stem cells.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the ZFN(s), TALEN(s) or CRIPSR/Cas systems. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113;

6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors (DNA MC(s)). When multiple vectors are used, each vector may comprise a sequence encoding one or multiple nucleases and/or donor constructs. Conventional viral and non-viral based gene transfer methods can be used to introduce nucleic acids encoding nucleases and/or donor constructs in cells (e.g., mammalian cells) and target tissues. Non-viral vector delivery systems include DNA or RNA plasmids, DNA MCs, naked nucleic acid, and nucleic acid complexed with a delivery vehicle such as a liposome or poloxamer. Suitable non-viral vectors include nanotaxis vectors, including vectors commercially available from InCellArt (France). Viral vector delivery systems include DNA and RNA viruses, which have either episomal or integrated genomes after delivery to the cell. For a review of in vivo delivery of engineered DNA-binding proteins and fusion proteins comprising these binding proteins, see, e.g., Rebar (2004) *Expert Opinion Invest. Drugs* 13(7):829-839; Rossi et al. (2007) *Nature Biotech.* 25(12):1444-1454 as well as general gene delivery references such as Anderson, *Science* 256:808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et at (2009) *Nature Biotechnology* 27(7):643).

The use of RNA or DNA viral based systems for the delivery of nucleic acids encoding engineered ZFPs, TALEs and/or CRISPR/Cas systems take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV2, AAV3, AAV4, AAV5, AAV6, AAV7, AAV8, AAV9 and AAVrh.10 and any novel AAV serotype can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides (e.g. nuclease-encoding and/or double-stranded donors) described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/0117617.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

It will be apparent that the nuclease-encoding sequences and donor constructs can be delivered using the same or different systems. For example, the nucleases and donors can be carried by the same DNA MC. Alternatively, a donor polynucleotide can be carried by a MC, while the one or more nucleases can be carried by a standard plasmid or AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Thus, the instant disclosure includes in vivo or ex vivo treatment of diseases and conditions that are amenable to insertion of a transgenes encoding a therapeutic protein. The compositions are administered to a human patient in an amount effective to obtain the desired concentration of the therapeutic polypeptide in the serum or the target organ or cells. Administration can be by any means in which the polynucleotides are delivered to the desired target cells. For example, both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree. Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al., (1994) *Nature Genetics,* 6:335-341.

The effective amount of nuclease(s) and donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.,* 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Cells

Also described herein are cells and/or cell lines in which an endogenous BCL11A enhancer sequence is modified. The modification may be, for example, as compared to the wild-type sequence of the cell. The cell or cell lines may be heterozygous or homozygous for the modification. The modifications to the BCL11A sequence may comprise insertions, deletions and/or combinations thereof.

The BCL11A enhancer sequence may be modified by a nuclease (e.g., ZFN, TALEN, CRISPR/Cas system, Ttago system, etc.), for example a nuclease as described herein. In certain embodiments, the BCL11A enhancer is modified anywhere between exon 2 and exon 3. In other embodiments, the BCL11A enhancer is modified in the regions shown in SEQ ID NO:1, SEQ ID NO:2 or SEQ ID NO:3 (FIG. 11). The modification is preferably at or near the nuclease(s) binding and/or cleavage site(s), for example, within 1-300 (or any value therebetween) base pairs upstream or downstream of the site(s) of cleavage, more preferably within 1-100 base pairs (or any value therebetween) of either side of the binding and/or cleavage site(s), even more preferably within 1 to 50 base pairs (or any value therebetween) on either side of the binding and/or cleavage site(s). In certain embodiments, the modification is at or near the "+58" region of the BCL11A enhancer, for example, at or near a nuclease binding site shown in any of SEQ ID NOs:4 to 80 and 276. In other embodiments, the modification is at or near the "+55" region of the BCL11A enhancer, for example, at or near a nuclease site shown in any of SEQ ID NOs:143 to 184 and 232-251.

Any cell or cell line may be modified, for example a stem cell, for example an embryonic stem cell, an induced pluripotent stem cell, a hematopoietic stem cell, a neuronal stem cell and a mesenchymal stem cell. Other non-limiting examples of cells as described herein include T-cells (e.g., CD4+, CD3+, CD8+, etc.); dendritic cells; B-cells. A descendent of a stem cell, including a partially or fully differentiated cell, is also provided (e.g., a RBC or RBC precursor cell). Non-limiting examples other cell lines including a modified BCL11A sequence include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces.*

The cells as described herein are useful in treating and/or preventing a disorder, for example, by ex vivo therapies. The nuclease-modified cells can be expanded and then reintroduced into the patient using standard techniques. See, e.g., Tebas et at (2014) *New Eng J Med* 370(10):901. In the case of stem cells, after infusion into the subject, in vivo differentiation of these precursors into cells expressing the functional transgene also occurs. Pharmaceutical compositions comprising the cells as described herein are also provided. In addition, the cells may be cryopreserved prior to administration to a patient.

Any of the modified cells or cell lines disclosed herein may show increased expression of gamma globin. Compositions such as pharmaceutical compositions comprising the genetically modified cells as described herein are also provided Applications The methods and compositions disclosed herein are for modifying expression of protein, or correcting an aberrant gene sequence that encodes a protein expressed in a genetic disease, such as a sickle cell disease or a thalassemia. Thus, the methods and compositions provide for the treatment and/or prevention of such genetic diseases. Genome editing, for example of stem cells, can be used to correct an aberrant gene, insert a wild type gene, or change the expression of an endogenous gene. By way of non-limiting example, a wild type gene, e.g. encoding at least one globin (e.g., α and/or β globin), may be inserted into a cell (e.g., into an endogenous BCL11a enhancer sequence using one or more nucleases as described herein) to provide the globin proteins deficient and/or lacking in the cell and thereby treat a genetic disease, e.g., a hemoglobinopathy, caused by faulty globin expression. Alternatively or in addition, genomic editing with or without administration of the appropriate donor, can correct the faulty endogenous gene, e.g., correcting the point mutation in α- or β-hemoglobin, to restore expression of the gene and/or treat a genetic disease, e.g. sickle cell disease and/or knock out or alteration (overexpression or repression) of any direct or indirect globin regulatory gene (e.g. inactivation of the γ globin-regulating gene BCL11A or the BCL11A-regulator KLF1). Specifically, the methods and compositions of the invention have use in the treatment or prevention of hemoglobinopathies.

The nucleases of the invention are targeted to the BCL11A enhancer region, known to be required for the expression of BCL11A, and hence the down regulation of gamma globin expression. Modification of this enhancer region may result in erythrocytes with increased gamma globin expression, and thus may be helpful for the treatment or prevention of sickle cell disease or beta thalassemia.

The following Examples relate to exemplary embodiments of the present disclosure in which the nuclease comprises a zinc finger nuclease (ZFN) or TALEN. It will be appreciated that this is for purposes of exemplification only and that other nucleases can be used, for example TtAgo and CRISPR/Cas systems, homing endonucleases (meganucleases) with engineered DNA-binding domains and/or fusions of naturally occurring of engineered homing endonucleases (meganucleases) DNA-binding domains and heterologous cleavage domains and/or fusions of meganucleases and TALE proteins.

EXAMPLES

Example 1

Assembly of Zinc Finger Nucleases and TALEN Nucleases

ZFNs were assembled against the human BCL11A gene and were tested by CEL1 assays as described in Miller et all. (2007) *Nat. Biotechnol.* 25:778-785. TALENs were assembled as described in Miller et al (2011) *Nature Biotechnology* 29 (2): 143-151. Additionally, see co-owned U.S. Patent Publication No. 20140093913 and U.S. Pat. No. 8,586,526. The TALENs were assembled with the +63 architecture.

Example 2

Introduction of Deletions in the +55, +58 and +62 BCL11A Enhancer Regions

To test which regions of the BCL11A intron 2 (FIG. 1) enhancer region were required for repression of gamma globin in during erythropoiesis, a series of TALENs were made to target sections of these regions (FIG. 2). The TALEN pairs are shown below in Table 1. Nucleotides in the target site that are contacted by the nuclease are indicated in uppercase letters; non-contacted nucleotides indicated in lowercase.

TABLE 1

TALENs targeted to the BCL11A enhancer region

| Sample | SBS # | target 5'->3' | # of RVDs | SEQ ID NO: | N->C RVD Sequence |
|---|---|---|---|---|---|
| 55R | 102740 | ctACATAGAGGCCCTTCCTgc | 17 | 276 | NI-HD-NI-NG-NI-NN-NI-NN-NN-HD-HD-HD-NG-NG-HD-HD-NG |
|  | 102741 | gtGGAGGGGATAACTGGGTca | 17 | 4 | NN-NN-NI-NN-NN-NN-NN-NI-NG-NI-NI-HD-NG-NN-NN-NN-NG |
| 55M | 102736 | ttGTGTGCTTGGTCGGCACtg | 17 | 5 | NN-NG-NN-NG-NN-HD-NG-NG-NN-NN-NG-HD-NN-NN-HD-NI-HD |
|  | 102737 | gtGCCGACAACTCCCTACCgc | 17 | 6 | NN-HD-HD-NN-NI-HD-NI-NI-HD-NG-HD-HD-HD-NG-NI-HD-HD |
| 58R | 102756 | gtGCCGACAACTCCCTACCgc | 17 | 6 | HD-NG-NG-NN-NN-NG-NN-NI-NG-NN-NN-NI-NN-NI-NI-NG-NG |
|  | 102757 | atTATTTCATTCCCATTGAga | 17 | 7 | NG-NI-NG-NG-NG-HD-NI-NG-NG-HD-HD-HD-NI-NG-NG-NN-NI |
| 58M | 102752 | atAGGCCAGAAAAGAGATAtg | 17 | 8 | NI-NN-NN-HD-HD-NI-NN-NI-NI-NI-NI-NN-NI-NN-NI-NG-NI |
|  | 102753 | ctGGTGTGTTATGTCTAAGag | 17 | 9 | NN-NN-NG-NN-NG-NN-NG-NG-NI-NG-NN-NG-HD-NG-NI-NI-NK |
| 58L | 102750 | ctAGTTTATAGGGGGTTCTac | 17 | 10 | NI-NN-NG-NG-NG-NI-NG-NI-NN-NN-NN-NN-NN-NG-NG-HD-NG |
|  | 102751 | atAGCACCCAAGGTCCATCag | 17 | 11 | NI-NN-HD-NI-HD-HD-HD-NI-NI-NN-NN-NG-HD-HD-NI-NG-HD |
| 62R | 102775 | atTCAACAAATAGCATATAaa | 17 | 12 | NG-HD-NI-NI-HD-NI-NI-NI-NG-NI-NN-HD-NI-NG-NI-NG-NI |
|  | 102774 | ctTCCCTTTTAGGAAGGTAaa | 17 | 13 | NG-HD-HD-HD-NG-NG-NG-NG-NI-NN-NN-NI-NI-NN-NN-NG-NI |

TABLE 1-continued

TALENs targeted to the BCL11A enhancer region

| Sample | SBS # | target 5'->3' | # of RVDs | SEQ ID NO: | N->C RVD Sequence |
|---|---|---|---|---|---|
| 62L | 102795 | atGCCAGAGGGCAGCAAACat | 17 | 14 | NN-HD-HD-NI-NN-NI-NN-NN-NN-HD-NI-NN-HD-NI-NI-NI-HD |
|  | 102794 | ctTAATAGCTGAAGGGGGCca | 17 | 15 | NG-NI-NI-NG-NI-NN-HD-NG-NN-NI-NI-NN-NN-NN-NN-NN-HD |

Human K562 cells were cultured in DMEM supplemented with 10% FBS and 200,000 cells were transfected with 800 ng of plasmid DNA encoding the TALENs by Amaxa Nucleofector® following the manufacturer's instructions. The Cel-I assay (Surveyor™, Transgenomics) as described in Perez et al. (2008) *Nat. Biotechnol.* 26: 808-816 and Guschin et al. (2010) *Methods Mol Biol.* 649:247-56), was used to detect TALEN-induced modifications of the target gene. In this assay, PCR-amplification of the target site was followed by quantification of insertions and/or deletions (indels) using the mismatch detecting enzyme Cel-I (Yang et al. (2000) *Biochemistry* 39: 3533-3541) which provided a lower-limit estimate of DSB frequency. Deep sequencing on the Illumina platform ("miSEQ") was used according to the manufacturer's instructions to measure editing efficiency as well as nature of editing-generated alleles. To detect deletions following cell treatment with more than one nuclease pair, a PCR-based assay was used in which bulk genomic DNA is amplified with primers that flank the region to be deleted, and a gel is used to separate the PCR product derived from the wild-type allele and the one derived from the deletion-bearing allele. All designs shown in Table 1 were active.

Three days following transfection of the TALEN expression vector at standard conditions (37° C.) genomic DNA was isolated from K562 cells using the DNeasy kit (Qiagen) or QuickExtract (Epicentre) and subject to PCR amplification.

The results from the Cel-I assay demonstrated that the TALENs were capable of inducing cleavage at their respective target sites.

To test the effect on relative gamma globin expression, the mRNAs encoding the TALEN pairs were introduced into CD34+ cells (obtained from healthy donor volunteers) by BTX nucleofection according to manufacturer's instructions. The cells were then differentiated into erythrocytes. Briefly, CD34+ cells were purified using Ficoll-Paque (GE Healthcare) and CD34+ microbeads (MiltenyiBiotec) according to the manufacturers' instructions. CD34+ cells were cultured in Iscove's MDM with BIT 95000 (StemCell Technologies) in the presence of growth factors. Cells were differentiated toward the erythroid lineage using a 3 step liquid culture model. During the first 6 days (first phase), CD34+ cells were expanded with SCF (100 ng/ml), Flt3-L (100 ng/ml), and IL-3 (20 ng/ml). Expanded cells were then committed and differentiated toward the erythroid lineage (second phase) with Epo (2 U/ml) and SCF (50 ng/ml). See, Giarratana et al. (2011) *Blood* 118(19):5071-9.

Figure 3:
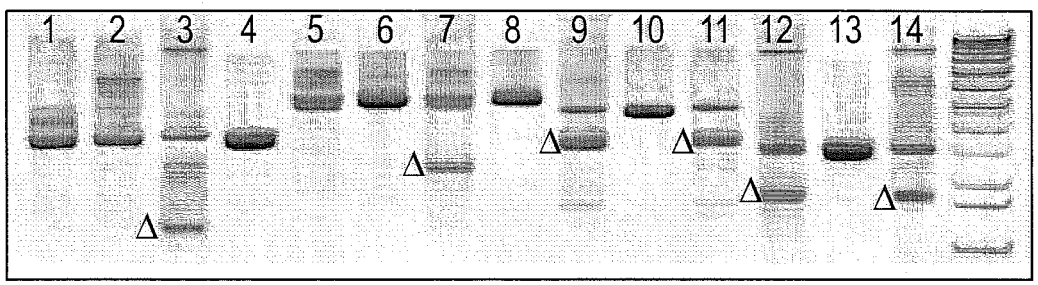
FIG. 3 depicts the results of in-cell cleavage by the TALEN pair sets (indicated in the table in the upper panel of the figure) in the BCL11A enhancer region as gauged by a PCR-based assay for deletion of various regions of the enhancer. Pairs of TALENs used were designed to create deletions in human HSPCs either within the +55 region ("55L-R"), within the +62 region ("62L-R), or within the +58 region ("58L-R", "58M-R"). The gel shows PCR products produced by isolating genomic DNA from human HSPCs transfected with expression constructs encoding the indicated TALENs and amplifying the region surrounding the target region. These data demonstrate the generation of deletions (band indicated by the symbol Δ) in the targeted region following cleavage by the TALEN pair sets indicated.
Figure 4:
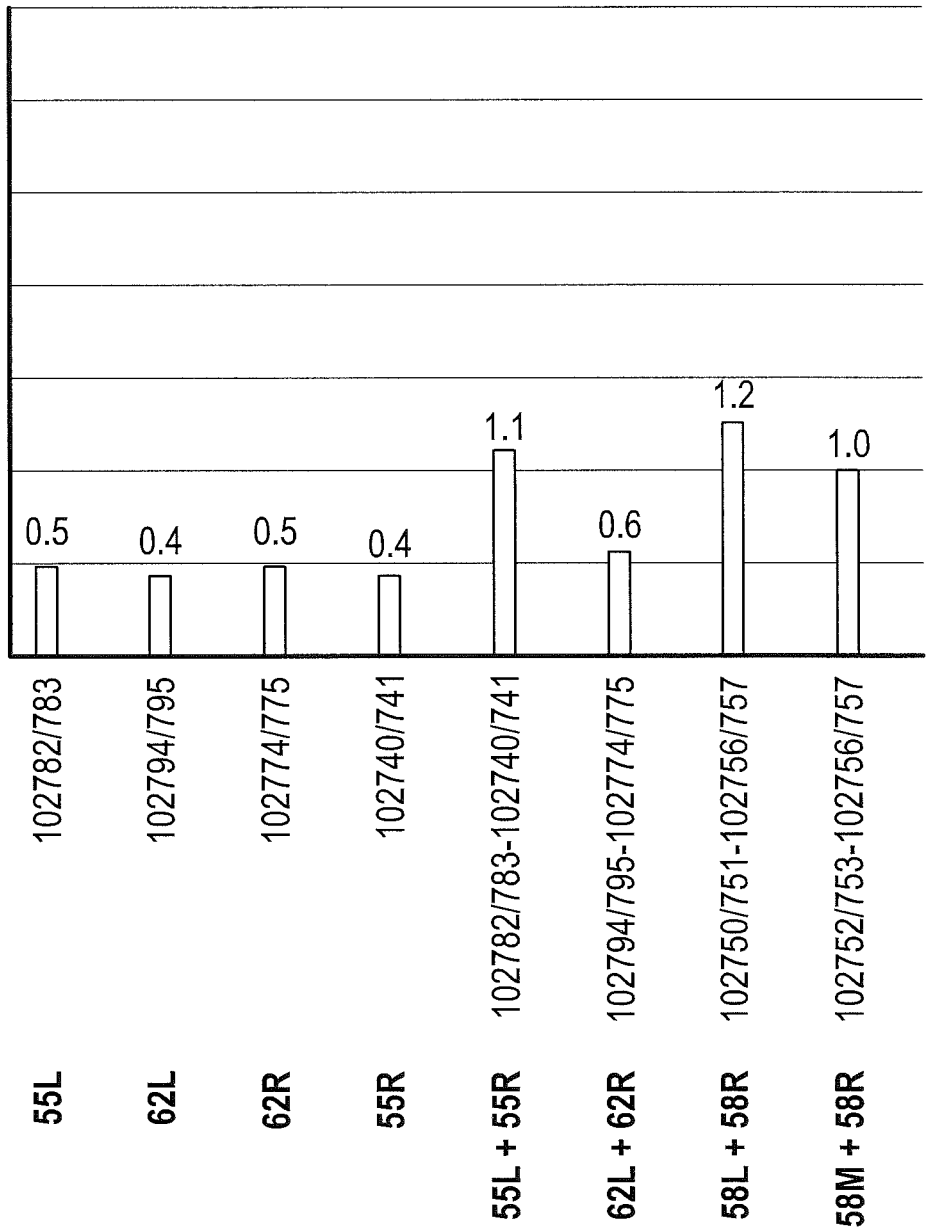
FIG. 4 is a graph showing results from a real-time RT-qPCR ("Taqman®") analysis designed to detect a change in expression of fetal gamma-globin mRNA following targeted editing of the BCL11A enhancer. Following electroporation of CD34 cells from healthy human volunteers with mRNAs encoding the designated nucleases (see FIG. 3), erythrocytes were generated in vitro, after which total RNA was harvested. The relative levels of alpha globin and gamma globin mRNA for each sample were determined in an RT-PCR Taqman® analysis, and the relative ratio of gamma globin mRNA/alpha globin mRNA was plotted. Thus, increasing gamma globin expression in the nuclease-treated samples leads to an increase in the normalized gamma/alpha ratio compared to the controls. The Figure displays the results from treating CD34 cells with single TALEN pairs and for the TALEN pair sets described in FIGS. 2 and 3. The level of gamma/alpha is increased for the 58L-R and 58M-R pair sets. Note that the ratio in the GFP transfection control was 3.4 in this experiment.
Figure 5:
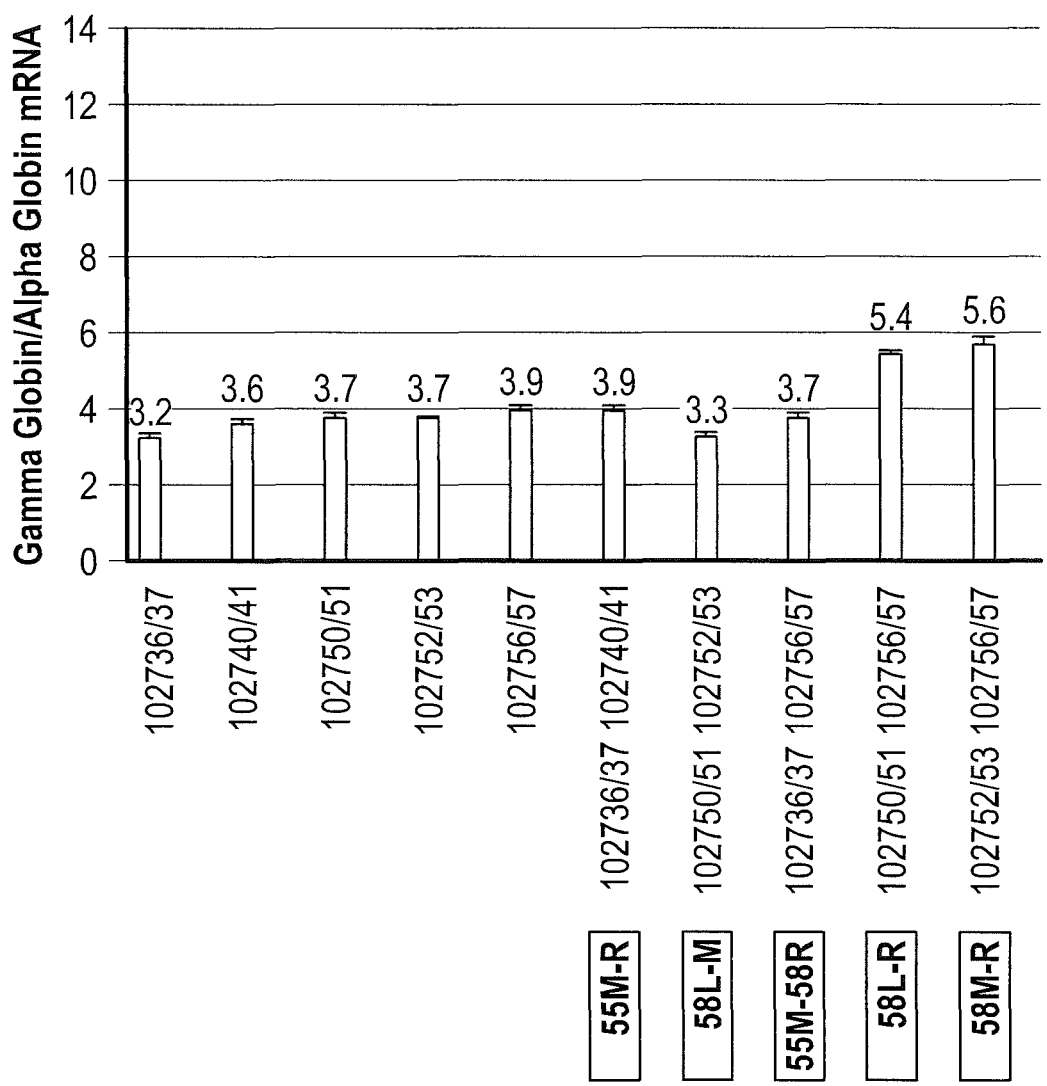
FIG. 5 is a graph showing results from a real-time RT-qPCR ("Taqman®") analysis designed to detect a change in expression of fetal gamma-globin mRNA following targeted editing of the BCL11A enhancer. Following electroporation of CD34 cells from healthy human volunteers with mRNAs encoding the designated nucleases (see FIG. 3), erythrocytes were generated in vitro, after which total RNA was harvested. The relative levels of beta globin and gamma globin mRNA for each sample were determined in an RT-PCR Taqman® analysis, and the relative ratio of gamma globin mRNA/beta globin mRNA was plotted. The results demonstrate that while the specific single TALEN pairs used in these experiments were not able to induce a change in gamma globin expression, creation of deletions by use of the pair sets caused an increase in relative gamma expression, corrected by adult beta globin expression in this instance. In particular, deletion of the DNA sequenced encompassed by the +55 or of the +58 DNAse I hypersensitive elevated gamma globin, while such elevation following a deletion of the sequence encompassed by the +62 DNAse I hypersensitive site was not detected in this experiment. Note that the ratio in the GFP transfection control was 0.5 in this experiment.

To analyze relative gamma globin expression, the ratios of mRNAs encoding gamma globin and beta globin following TALEN treatment were determined at 14 days following TALEN introduction by Taqman® analysis. The analysis was done by standard Taqman® analysis, following the protocol and using gene specific assays supplied by the manufacturer (Applied Biosystems) and the primer sets supplied. The relative levels of gamma globin were normalized by the level of alpha or beta globin expression where the ratio was compared to the alpha/beta or gamma/beta ratio in untreated cells. The results (FIGS. 3, 4 and 5) demonstrated that deletions of regions within the +58 and +55 BCL11A DNAseI hypersensitive site resulted in an increase in the relative levels of gamma globin expression in these experiments.

Example 3

TALEN "Walk Across" the +58 DNAse I Hypersensitive Site in BCL11A

To further define the area required for enhancer activity in the +58 region, a series of TALENs were made to create a series of DSBs and deletions across this stretch of DNA. The TALENs used in this experiment are shown below in Table 2.

TABLE 2

TALENs used in the +58 enhancer walk

| Sample | SBS # | target 5'->3' | # of RVDs | SEQ ID NO: | N->C RVD Sequence |
|---|---|---|---|---|---|
| 1 | 102830 | gtGTGCATAAGTAAGAGCAga | 17 | 16 | NN-NG-NN-HD-NI-NG-NI-NI-NN-NG-NI-NI-NN-NI-NN-HD-NI |
|  | 102831 | ctGTATGGACTTTGCACTGga | 17 | 17 | NN-NG-NI-NG-NN-NN-NI-HD-NG-NG-NG-NN-HD-NI-HD-NG-NK |
| 2 | 102832 | gtAAGAGCAGATAGCTGATtc | 17 | 18 | NI-NI-NN-NI-NN-HD-NI-NN-NI-NG-NI-NN-HD-NG-NN-NI-NG |
|  | 102833 | atGTTATTACCTGTATGGAct | 17 | 19 | NN-NG-NG-NI-NG-NG-NI-HD-HD-NG-NN-NG-NI-NG-NN-NN-NI |

TABLE 2-continued

TALENs used in the +58 enhancer walk

| Sample | SBS # | target 5'->3' | # of RVDs | SEQ ID NO: | N->C RVD Sequence |
|---|---|---|---|---|---|
| 3 | 102834 | atAGCTGATTCCAGTGCAAag | 17 | 20 | NI-NN-HD-NG-NN-NI-NG-NG-HD-HD-NI-NN-NG-NN-HD-NI-NI |
|  | 102835 | ttTTCTGGCCTATGTTATTac | 17 | 21 | NG-NG-HD-NG-NN-NN-HD-HD-NG-NI-NG-NN-NG-NI-NG-NG |
| 4 | 102836 | gtGCAAAGTCCATACAGGTaa | 17 | 22 | NN-HD-NI-NI-NI-NN-NG-HD-HD-NI-NG-NI-HD-NI-NN-NN-NG |
|  | 102837 | atGCCATATCTCTTTTCTGgc | 17 | 23 | NN-HD-HD-NI-NG-NI-NG-HD-NG-HD-NG-NG-NG-NG-HD-NG-NK |
| 5 | 102838 | atACAGGTAATAACATAGGcc | 17 | 24 | NI-HD-NI-NN-NN-NG-NI-NI-NG-NI-NI-HD-NI-NG-NI-NN-NK |
|  | 102839 | ctAAGAGTAGATGCCATATct | 17 | 25 | NI-NI-NN-NI-NN-NG-NI-NN-NI-NG-NN-HD-HD-NI-NG-NI-NG |
| 6 | 102840 | atAACATAGGCCAGAAAAGag | 17 | 26 | NI-NI-HD-NI-NG-NI-NN-NN-HD-HD-NI-NI-NI-NI-NI-NK |
|  | 102841 | gtGTTATGTCTAAGAGTAGat | 17 | 27 | NN-NG-NG-NI-NG-NN-NG-HD-NG-NI-NI-NN-NI-NN-NG-NI-NK |
| 7 | 102842 | ctCTTAGACATAACACACCag | 17 | 28 | HD-NG-NG-NI-NN-NI-HD-NI-NG-NI-NI-HD-NI-HD-NI-HD-HD |
|  | 102843 | ctAGACTAGCTTCAAAGTTgt | 17 | 29 | NI-NN-NI-HD-NG-NI-NN-HD-NG-NG-HD-NI-NI-NI-NN-NG-NG |
| 8 | 102844 | atAACACACCAGGGTCAATac | 17 | 30 | NI-NI-HD-NI-HD-NI-HD-HD-NI-NN-NN-NN-NG-HD-NI-NI-NG |
|  | 102845 | gtTAGCTTGCACTAGACTAgc | 17 | 31 | NG-NI-NN-HD-NG-NG-NN-HD-NI-HD-NI-NN-NI-HD-NG-NI |
| 9 | 102846 | gtCAATACAACTTTGAAGCta | 17 | 32 | HD-NI-NI-NG-NI-HD-NI-NI-HD-NG-NG-NG-NN-NI-NI-NN-HD |
|  | 102847 | atAAAAGCAACTGTTAGCtt | 17 | 33 | NI-NI-NI-NI-NN-HD-NI-NI-HD-NG-NN-NG-NG-NI-NN-HD |
| 10 | 102848 | ttGAAGCTAGTCTAGTGCAag | 17 | 34 | NN-NI-NI-NN-HD-NG-NI-NN-NG-HD-NG-NI-NN-NG-NN-HD-NI |
|  | 102849 | ctGGAGCCTGTGATAAAAGca | 17 | 35 | NN-NN-NI-NN-HD-HD-NG-NN-NN-NN-NI-NG-NI-NI-NI-NI-NK |
| 11 | 102850 | ctAGTCTAGTGCAAGCTAac | 17 | 36 | NI-NN-NG-HD-NG-NI-NN-NG-NN-HD-NI-NI-NN-HD-NG-NI |
|  | 102851 | ctTCCTGGAGCCTGTGATAaa | 17 | 37 | NG-HD-HD-NG-NN-NN-HD-HD-NG-NN-NG-NN-NI-NG-NI |
| 12 | 102852 | gtGCAAGCTAACAGTTGCTtt | 17 | 38 | NN-HD-NI-NI-NN-HD-NG-NI-NI-HD-NI-NN-NG-NG-NN-HD-NG |
|  | 102853 | atCAGAGGCCAAACCCTTCct | 17 | 39 | HD-NI-NN-NI-NN-NN-HD-HD-NI-NI-NI-HD-HD-HD-NG-NG-HD |
| 13 | 102854 | ctAACAGTTGCTTTTATCAca | 17 | 40 | NI-NI-HD-NI-NN-NG-NG-NN-HD-NG-NG-NG-NG-NI-NG-HD-NI |
|  | 102855 | ctAATCAGAGGCCAAACCCtt | 17 | 41 | NI-NI-NG-HD-NI-NN-NI-NN-NN-HD-HD-NI-NI-NI-HD-HD |
| 14 | 102856 | atCACAGGCTCCAGGAAGGgt | 17 | 42 | HD-NI-HD-NI-NN-NN-HD-NG-HD-HD-NI-NN-NN-NI-NI-NN-NK |

TABLE 2-continued

TALENs used in the +58 enhancer walk

| Sample | SBS # | target 5'->3' | # of RVDs | SEQ ID NO: | N->C RVD Sequence |
|---|---|---|---|---|---|
| | 102857 | ctACCCCACCCACGCCCCCac | 17 | 43 | NI-HD-HD-HD-HD-NI-HD-HD-HD-NI-HD-NN-HD-HD-HD-HD-HD |
| 15 | 102858 | ctCCAGGAAGGGTTTGGCCtc | 17 | 44 | HD-HD-NI-NN-NN-NI-NI-NN-NN-NN-NG-NG-NG-NN-NN-HD-HD |
| | 102859 | ctACCCCACCCACGCCCCCac | 17 | 45 | NI-HD-HD-HD-HD-NI-HD-HD-HD-NI-HD-NN-HD-HD-HD-HD-HD |
| 16 | 102860 | ttGGCCTCTGATTAGGGTGgg | 17 | 46 | NN-NN-HD-HD-NG-HD-NG-NN-NI-NG-NG-NI-NN-NN-NN-NG-NK |
| | 102861 | ctGCCAGTCCTCTTCTACCcc | 17 | 47 | NN-HD-HD-NI-NN-NG-HD-HD-NG-HD-NG-HD-NG-NI-HD-HD |
| 17 | 102862 | atTAGGGTGGGGCGTGGGtg | 17 | 48 | NG-NI-NN-NN-NN-NG-NN-NN-NN-NN-NN-HD-NN-NG-NN-NN-NK |
| | 102863 | atGGAGAGGTCTGCCAGTCct | 17 | 49 | NN-NN-NI-NN-NI-NN-NN-NG-HD-NG-NN-HD-HD-NI-NN-NG-HD |
| 18 | 102864 | gtGGGGTAGAAGAGGACTGgc | 17 | 50 | NN-NN-NN-NN-NG-NI-NN-NI-NI-NN-NI-NN-NN-NI-HD-NG-NK |
| | 102865 | ctGGGCAAACGGCCACCGAtg | 17 | 51 | NN-NN-NN-HD-NI-NI-NI-HD-NN-NN-HD-HD-NI-HD-HD-NN-NI |
| 19 | 102866 | ctGGCAGACCTCTCCATCGgt | 17 | 52 | NN-NN-HD-NI-NN-NI-HD-HD-NG-HD-NG-HD-HD-NI-NG-HD-NK |
| | 102867 | ctTCCGAAAGAGGCCCCCCtg | 17 | 53 | NG-HD-HD-NN-NI-NI-NI-NN-NI-NN-NN-HD-HD-HD-HD-HD-HD |
| 20 | 102868 | atCGGTGGCCGTTTGCCCag | 16 | 54 | HD-NN-NN-NG-NN-NN-HD-HD-NN-NG-NG-NG-HD |
| | 102869 | atCACCAAGAGAGCCTTCCga | 17 | 55 | HD-NI-HD-HD-NI-NI-NN-NI-NN-NI-NN-HD-HD-NG-NG-HD-HD |
| 21 | 102870 | gtTTGCCCAGGGGGGCCTCtt | 17 | 56 | NG-NG-NN-HD-HD-HD-NI-NN-NN-NN-NN-NN-NN-HD-HD-NG-HD |
| | 102871 | atTCTCCATCACCAAGAGAgc | 17 | 57 | NG-HD-NG-HD-HD-NI-NG-HD-NI-HD-HD-NI-NI-NN-NI-NN-NI |
| 22 | 102872 | ttGCCCAGGGGGGCCTCTTtc | 17 | 58 | NN-HD-HD-HD-NI-NN-NN-NN-NN-NN-NN-HD-HD-NG-HD-NG-NG |
| | 102873 | atAAAATCCAATTCTCCATca | 17 | 59 | NI-NI-NI-NI-NG-HD-HD-NI-NI-NG-NG-NG-HD-HD-NI-NG |
| 23 | 102874 | ctTTCGGAAGGCTCTCTTGgt | 17 | 60 | NG-NG-HD-NN-NN-NI-NI-NN-NN-HD-NG-HD-NG-HD-NG-NG-NK |
| | 102875 | atTGAGAAATAAAATCCAAtt | 17 | 61 | NG-NN-NI-NN-NI-NI-NI-NG-NI-NI-NI-NI-NG-HD-HD-NI-NI |
| 58R | 102756 | ctCTTGGTGATGGAGAATTgg | 17 | 62 | HD-NG-NG-NN-NN-NG-NN-NI-NG-NN-NN-NI-NN-NI-NI-NG-NG |
| | 102757 | atTATTTCATTCCCATTGAga | 17 | 7 | NG-NI-NG-NG-NG-HD-NI-NG-NG-HD-HD-HD-NI-NG-NG-NN-NI |

TABLE 2-continued

TALENs used in the +58 enhancer walk

| Sample | SBS # | target 5'->3' | # of RVDs | SEQ ID NO: | N->C RVD Sequence |
|---|---|---|---|---|---|
| 58M | 102752 | atAGGCCAGAAAAGAGATAtg | 17 | 8 | NI-NN-NN-HD-HD-NI-NN-NI-NI-NI-NI-NN-NI-NN-NI-NG-NI |
|  | 102753 | ctGGTGTGTTATGTCTAAGag | 17 | 9 | NN-NN-NG-NN-NG-NN-NG-NG-NI-NG-NN-NG-HD-NG-NI-NI-NK |
| 58L | 102750 | ctAGTTTATAGGGGGTTCTac | 17 | 10 | NI-NN-NG-NG-NG-NI-NG-NI-NN-NN-NN-NN-NN-NG-NG-HD-NG |
|  | 102751 | atAGCACCCAAGGTCCATCag | 17 | 11 | NI-NN-HD-NI-HD-HD-HD-NI-NI-NN-NN-NG-HD-HD-NI-NG-HD |

Figure 6:
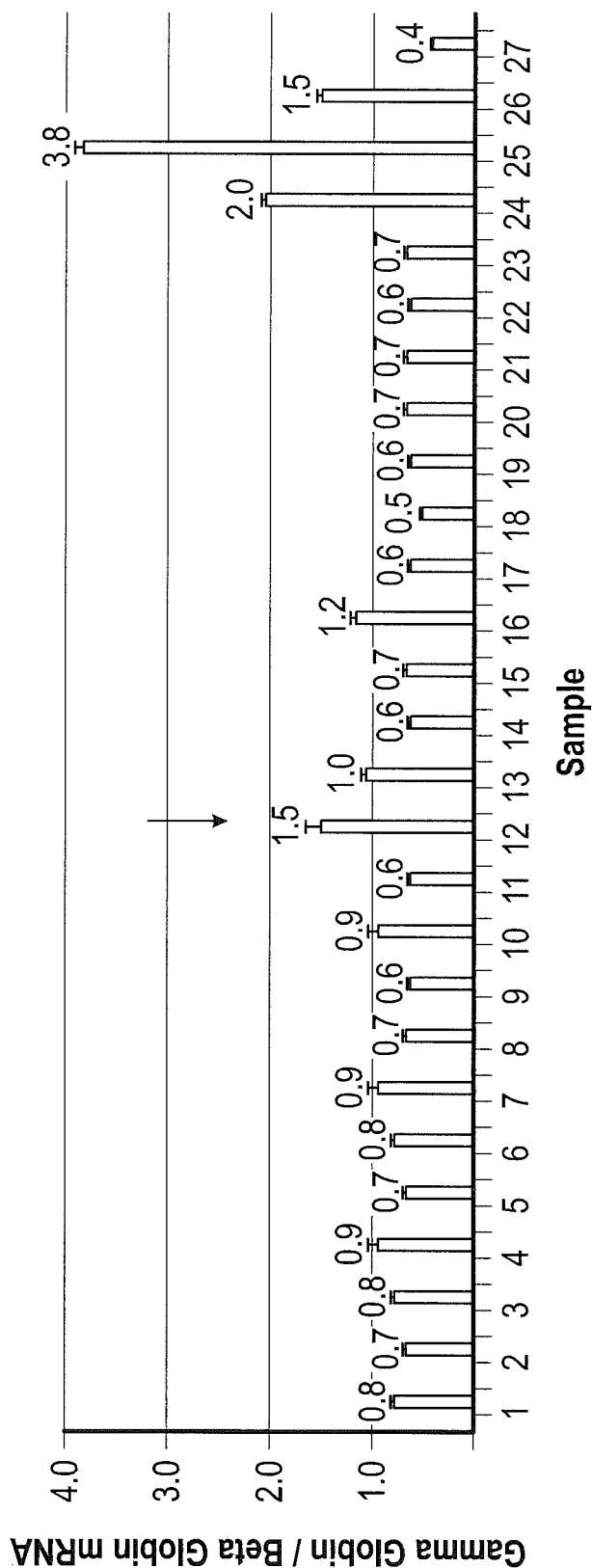
FIG. 6 shows the results from a Taqman® analysis for fetal globin levels as described in FIG. 4. In this set of experiments, the levels of beta globin and gamma globin mRNA were measured, and thus the data depicted is the ratio of gamma to beta and compared to the same gamma/beta ratio in control treated cells. A series of single TALEN pairs were used to "walk across" the +58 region of the BCL11A enhancer. In contrast to the earlier experiments where a deletion of 400-900 base pairs was required to see an increase in gamma expression, the results depicted in this experiment demonstrated a single site (indicated by an arrow) that when cleaved caused that relative increase. Results from the deletion pairs are included in this graph for comparison. See FIG. 7 for location of cleavage sites of the TALEN pairs across the region of interest.
Figure 7:
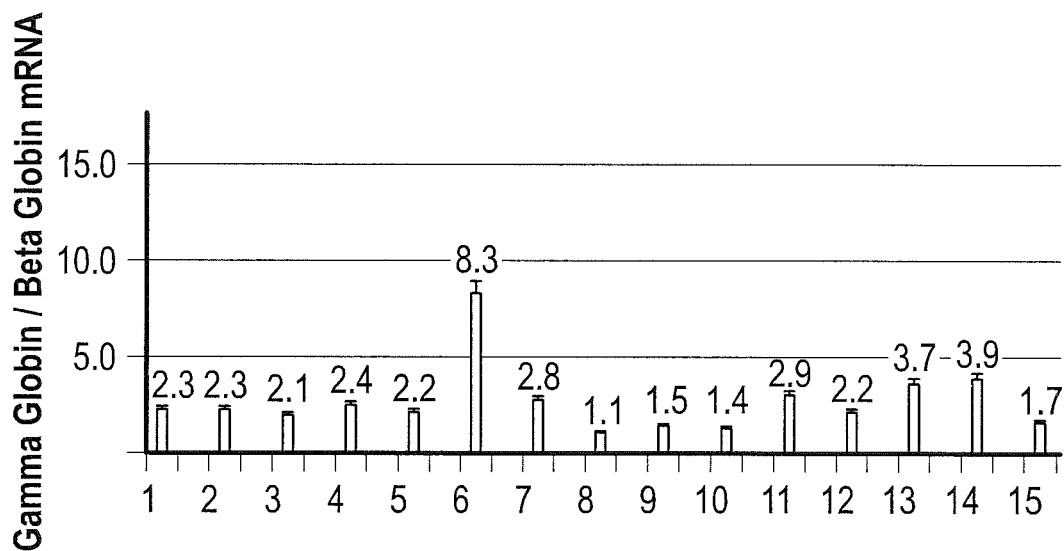
FIG. 7 shows the results from a Taqman® analysis as described in FIG. 4 using ZFN pairs targeted to the +58 enhancer region. The levels of beta globin and gamma globin were characterized and used to express the ratio of gamma to beta-globin compared to the same ratio in control treated cells. The data demonstrates that ZFN-driven disruption of the same region identified in the TALEN screen (FIG. 6 and see FIG. 8 below)) resulted in increased gamma globin expression. Note that the ratio in the GFP transfection control was 2.6 in this experiment.
Figure 8:
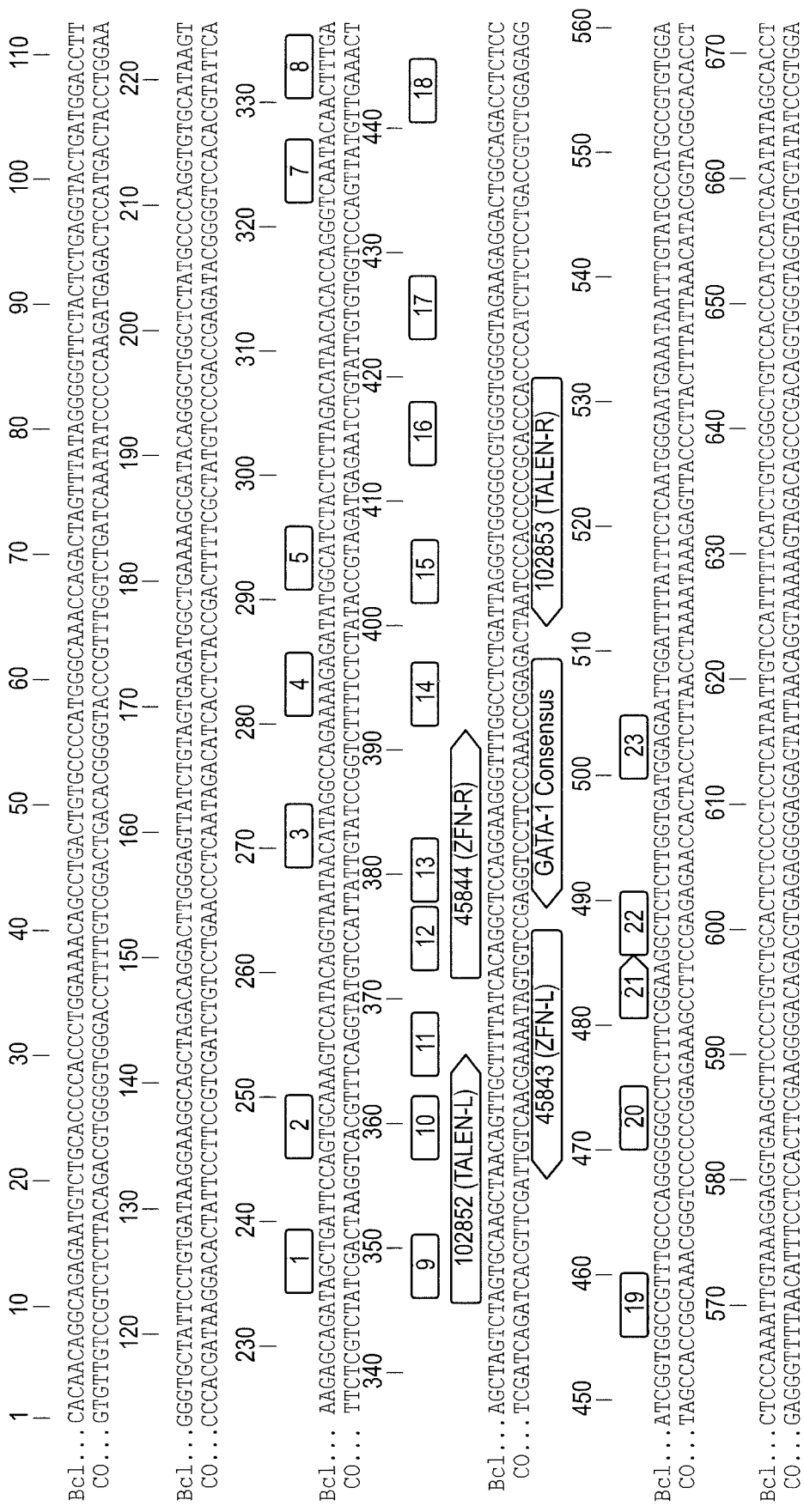
FIG. 8 shows a representation of the binding sites of the +58 enhancer region specific TALENs (102852 and 102853) and ZFNs (45843 and 45844), use of which in human HSPCs increases the relative expression of gamma globin following in vitro erythropoiesis. The sequence shown is the double stranded form of the DNA sequence encompassing the +58 region of the BCL11A enhancer (SEQ ID NO: 264), and the numbering system relates to the +58 itself. Also indicated in the figure is the location of a match to the binding site of the GATA-1-transcription factor (sequence of locus, gtGATAAag, consensus GATA-1 site—swGA-TAAvv). Additionally, the cleavage sites of the TALEN pairs used in the +58 "walk" are indicated where the numbers correspond to the samples used in the data sets presented in FIG. 6.

In this table, 'Sample' refers to the samples shown in FIG. 6. The results demonstrate that the TALEN pair 102853/102852 (indicated by the arrow in the figure) was able to increase relative gamma expression. Further, large deletions introduced by some pair sets of the TALENs (Sample 24: pair from Sample 22+pair from Sample 6; Sample 25: pair from Sample 16+pair from Sample 6; Sample 26: pair from Sample 22+pair from Sample 16) were also able to increase relative gamma expression. The TALENs were engineered in this study to probe throughout the +58 region (see FIG. 8 depicting the enhancer sequence and the TALEN cleavage sites). All designs shown in Table 2 were active.

Example 4

ZFNs Targeted to the +58 Enhancer Region of BCL11A

In parallel to the TALEN pairs described in Example 3, ZFN pairs were made to target the +58 region. The ZFNs used are shown below in Table 3. The nucleases are identified by their "SBS" number, a unique numeric identifier for each protein.

TABLE 3

ZFN pairs specific for +58 BCL11A enhancer region

| SBS # (target site, 5'-3') | Design | | | | | |
|---|---|---|---|---|---|---|
|  | F1 | F2 | F3 | F4 | F5 | F6 |
| 45796 atGGCTGAAA AGCGATACAG ggctggct (SEQ ID NO: 63) | RSDNLSE (SEQ ID NO: 81) | TRSPLRN (SEQ ID NO: 82) | RSDDLTR (SEQ ID NO: 83) | QKSNLSS (SEQ ID NO: 84) | QSAHRKN (SEQ ID NO: 85) | DSSHRTR (SEQ ID NO: 86) |
| 45795 tcACTACAGA TAACTCCcaa gtcctgtc (SEQ ID NO:64) | DSSDRKK (SEQ ID NO: 87) | DRSNRTT (SEQ ID NO: 88) | TNSNRKR (SEQ ID NO: 89) | QSGDLTR (SEQ ID NO: 90) | LKDTLRR (SEQ ID NO: 91) | N/A |
| 45802 caTAAGTAAG AGCAGATAGC tgattcca (SEQ ID NO: 65) | GYCCLRD (SEQ ID NO: 92) | TSGNLTR (SEQ ID NO: 93) | QSGDLTR (SEQ ID NO: 90) | QRTHLKA (SEQ ID NO: 94) | QSGALAR (SEQ ID NO: 95) | QSANRTK (SEQ ID NO: 96) |
| 45800 caCCTGGGGC AtAGAGCCag ccctgtat (SEQ ID NO: 66) | DSSDRKK (SEQ ID NO: 87) | QNAHRKT (SEQ ID NO: 97) | QSGDLTR (SEQ ID NO: 90) | RSDHLSR (SEQ ID NO: 98) | QQWDRKQ (SEQ ID NO: 99) | N/A |

TABLE 3-continued

ZFN pairs specific for +58 BCL11A enhancer region

| SBS # (target site, 5'-3') | Design | | | | | |
|---|---|---|---|---|---|---|
| | F1 | F2 | F3 | F4 | F5 | F6 |
| 45812 tcCATACAGG TAATaACATA Ggccagaa (SEQ ID NO: 67) | RSDYLSK (SEQ ID NO: 100) | TSSVRTT (SEQ ID NO: 101) | TNQNLTV (SEQ ID NO: 102) | TSGHLSR (SEQ ID NO: 103) | RSADLTR (SEQ ID NO: 104) | TNQNRIT (SEQ ID NO: 105) |
| 45813 acTTTGCACT GGAAtcagct atctgctc (SEQ ID NO: 68) | QSGALAR (SEQ ID NO: 95) | RLDWLPM (SEQ ID NO: 106) | QSGDLTR (SEQ ID NO: 90) | HKWVLRQ (SEQ ID NO: 107) | N/A | N/A |
| 45816 aaGTAAGAGC AGATAGCtga ttccagtg (SEQ ID NO: 69) | GYCCLRD (SEQ ID NO: 92) | TSGNLTR (SEQ ID NO: 93) | QSGDLTR (SEQ ID NO: 90) | QRTHLKA (SEQ ID NO: 94) | QSGALAR (SEQ ID NO: 95) | N/A |
| 45815 caCACCTGGG GCATAGAGCC agccctgt (SEQ ID NO: 70) | DSSDRKK (SEQ ID NO: 87) | QNAHRKT (SEQ ID NO: 97) | LKQNLDA (SEQ ID NO: 108) | RSAHLSR (SEQ ID NO: 109) | RSDVLST (SEQ ID NO: 110) | DTRNLRA (SEQ ID NO: 111) |
| 45844 tcACAGGCTC CAGGAAGGGT ttggcctc (SEQ ID NO: 71) | LRHHLTR (SEQ ID NO: 112) | RRDNLHS (SEQ ID NO: 113) | RSDHLSN (SEQ ID NO: 114) | DSRSRIN (SEQ ID NO: 115) | DRSHLTR (SEQ ID NO: 116) | QSGTRKT (SEQ ID NO: 117) |
| 45843 aaGCAACTGT TAGCTTGCAC tagactag (SEQ ID NO: 72) | DQSNLRA (SEQ ID NO: 118) | RPYTLRL (SEQ ID NO: 119) | TGYNLTN (SEQ ID NO: 120) | TSGSLTR (SEQ ID NO: 121) | QHQVLVR (SEQ ID NO: 122) | QNATRTK (SEQ ID NO: 123) |
| 45849 caCAGGCTCC AGGAAGGGTT tggcctct (SEQ ID NO: 73) | TSGSLSR (SEQ ID NO: 124) | RSDHLTQ (SEQ ID NO: 125) | QSGHLAR (SEQ ID NO: 126) | QKGTLGE (SEQ ID NO: 127) | QSSDLSR (SEQ ID NO: 128) | RRDNLHS (SEQ ID NO: 113) |
| 45848 aaAGCAACtG TTAGCTTGCA Ctagacta (SEQ ID NO: 74) | DQSNLRA (SEQ ID NO: 118) | RPYTLRL (SEQ ID NO: 119) | TGYNLTN (SEQ ID NO: 120) | TSGSLTR (SEQ ID NO: 121) | DQSNLRA (SEQ ID NO: 118) | AQCCLFH (SEQ ID NO: 129) |
| 45872 gtGGGGGCGT GGGTGGGGTA gaagagga (SEQ ID NO: 75) | QSGALAR (SEQ ID NO: 95) | RSDHLSR (SEQ ID NO: 98) | TSGHLSR (SEQ ID NO: 103) | RSDALAR (SEQ ID NO: 130) | DRSHLTR (SEQ ID NO: 116) | RSDHLSR (SEQ ID NO: 98) |
| 45871 ctAATCAGAG GCCAaaccct tcctggag (SEQ ID NO: 76) | QSNDLSN (SEQ ID NO: 131) | RSHHLKA (SEQ ID NO: 132) | RSDNLSE (SEQ ID NO: 81) | TSSNRKT (SEQ ID NO: 133) | N/A | N/A |

TABLE 3-continued

ZFN pairs specific for +58 BCL11A enhancer region

| SBS # (target site, 5'-3') | Design | | | | | |
|---|---|---|---|---|---|---|
| | F1 | F2 | F3 | F4 | F5 | F6 |
| 45881 tgGCCGTTtG CCCAGGGGGG Cctctttc (SEQ ID NO: 77) | DRSHLTR (SEQ ID NO: 116) | RSDHLSR (SEQ ID NO: 98) | RSDNLSE (SEQ ID NO: 81) | ASKTRKN (SEQ ID NO: 134) | TSGSLSR (SEQ ID NO: 124) | QWKSRAR (SEQ ID NO: 135) |
| 45880 cgATGGAGaG GTCTGCCAGT Cctcttct (SEQ ID NO: 78) | DRSALSR (SEQ ID NO: 136) | QSGDLTR (SEQ ID NO: 90) | RSDVLSE (SEQ ID NO: 137) | TSGHLSR (SEQ ID NO: 103) | RSANLAR (SEQ ID NO: 138) | RSDALTQ (SEQ ID NO: 139) |
| 45889 ttGCCCAGGG GGGCctctttt cggaaggc (SEQ ID NO: 79) | DRSHLTR (SEQ ID NO: 116) | RSDHLSR (SEQ ID NO: 98) | RSDNLSE (SEQ ID NO: 81) | ASKTRKN (SEQ ID NO: 134) | N/A | N/A |
| 45888 ccACCGATGG AGAGGTCtgc cagtcctc (SEQ ID NO: 80) | DRSALSR (SEQ ID NO: 136) | RSDNLTR (SEQ ID NO: 140) | QSGHLSR (SEQ ID NO: 141) | TSGNLTR (SEQ ID NO: 93) | DLTTLRK (SEQ ID NO: 142) | N/A |
| 48117 aaAGCAActG TTAGCTTGCA Ctagacta (SEQ ID NO: 74) | DQSNLRA (SEQ ID NO: 118) | RPYTLRL (SEQ ID NO: 119) | SGYNLEN (SEQ ID NO: 253) | TSGSLTR (SEQ ID NO: 121) | DQSNLRA (SEQ ID NO: 118) | AQCCLFH (SEQ ID NO: 129) |
| 48037 aaAGCAActG TTAGCTTGCA Ctagacta (SEQ ID NO: 74) | DQSNLRA (SEQ ID NO: 118) | RPYTLRL (SEQ ID NO: 119) | SGYNLEN (SEQ ID NO: 253) | TSGSLTR (SEQ ID NO: 121) | DQSNLRA (SEQ ID NO: 118) | AQCCLFH (SEQ ID NO: 129) |

These ZFNs were used to cleave the BCL11A+58 enhancer region in CD34 cells and transfected cells were analyzed for relative gamma expression after erythrocyte differentiation. One ZFN pair, 45844/45843 was identified that caused an increase in relative gamma expression as compared to cells treated with a GFP transduction control, or cells treated with other ZFNs. FIG. 8 shows that the site targeted by this ZFN pair partially overlap that targeted by the most active TALEN pair described in Example 3. Closer inspection of the sequence that is cleaved reveals that it contains a "GATA-1" consensus site (A/T GATA A/G), known to be one of the sequences bound by the GATA1 and related transcription factors. See, e.g., Martin and Orkin (1990) *Genes Dev* 4:1886-1898; Fujiwara et al. (2009) *Molecular Cell* 36:667-681; Tijssen et al. (2011) *Developmental Cell* 20:597-609; May et al. (2013) *Cell Stem Cell* 13:1-15. All designs shown in Table 3 were active.

A region comprising the cleavage site was amplified by PCR, and following amplification, the PCR product was sequenced via MiSeq high throughput sequencing analysis according to manufacturer's instructions (Ilumina) for both the ZFN 45843/45844 and TALEN 102852/102853 pairs. The 5 most common genotypes are shown below in Tables 5a and 5b, show cleavage at or near the nuclease target sites and reveal a nuclease-mediated loss of the GATA-1 consensus sequence (in box) in both instances (Table 5a shows SEQ ID NOS 277-281 from top to bottom; Table 5b shows SEQ ID NOS 282-286 from top to bottom). The TALEN pair cleaves slightly downstream of the consensus sequence, potentially resulting in a lesser incidence of the knock out of this sequence.

TABLE 5a

MiSeq analysis of deletion region for ZFN 45843/45844 pair

| Count | Seq-Length | LengthVs-Amplicon | | % overall | Alignment |
|---|---|---|---|---|---|
| 18669 | 123 | NA | 0 | 53.565 | ACACACCAGGGTCAATACAACTTTGAAGCTAGTCTAGTG CAAGCTAACAGTTGCTTTTATCACAGGCTCCAGGAAGG |
| 2187 | 108 | shorter | -15 | 6.275 | ACACACCAGGGTCAATACAACTTTGAAGCTAGTCTAGTG AAAGCTAACAG---------------GCTCAAGGAAGG |
| 1415 | 110 | shorter | -13 | 4.060 | ACACACCAGGGTCAATACAACTTTGAAGCTAGTCTAGTG CAAGCTAACAGTTGCT-------------CCAGGAAGG |
| 1374 | 122 | shorter | -1 | 3.942 | ACACACCAGGGTCAATACAACTTTGAAGCTAGTCTAGTG CAAGCTAACAGTTGCTTT-ATCACAGGCTCCGGGAAGG |
| 818 | 118 | shorter | -5 | 2.347 | ACACACCAGGGTCAATACAACTTTGGAGCTAGTCTAGTG CAAGCTAACAGTTGCC-----CACAGGCTCCAGGAAGG |

TABLE 5b

MiSeq analysis of deletion region for TALEN 102852/102853 pair

| Count | Seq-Lengh | LengthVs-Amplicon | | % overall | Alignment |
|---|---|---|---|---|---|
| 19238 | 123 | NA | 0 | 68.511 | ACACACCAGGGTCAATACAACTTTGAAGCTAGTCTAGT GCAAGCTAACAGTTGCTTTTATCACAGCTCCAGGAAGG |
| 1265 | 115 | shorter | -8 | 4.505 | ACACACCAGGGTCAATACAACTTTGAAGCTAGTCTAGTGC AAGCTACCAGTTGCTTTTATC--------CAGGAAGG |
| 893 | 110 | shorter | -13 | 3.180 | ACACACCAGGGTCAATACAACTTTGAAGCTAGTCTAGTGC AAGCTACCAGTTGCT-------------CCAGGAAGG |
| 524 | 121 | shorter | -2 | 1.866 | ACACACCAGGGTCAATACAACTTTGAAGCTAGTCTAGTGC AAGCTAACAGTTGCTTTCATCA--GGCTCCAGGAAGG |
| 449 | 122 | shorter | -1 | 1.599 | ACACACCAGGGTCAATACAACTTTGAAGCTAGTCTAGTGC AAGCTAACAGTTGCTTTTGTC-CAGGCTCCAGGAAGG |

Example 5

TALEN Walk Across the +55 DNAseI Hypersensitive Site in the BCL11A Enhancer Region To further refine the area required for enhancer activity in the +55 region, a series of TALEN pairs were made to create a series of mutations across this stretch of DNA. The TALEN pairs made in this experiment are shown below in Table 4.

TABLE 4

TALEN pairs that recognize the +55 BCL11A enhancer region

| Sample | SBS # | target 5'->3' | # of RVDs | SEQ ID NO: | N->C RVD Sequence |
|---|---|---|---|---|---|
| 1 | 102876 | atAATGAATGTCCCAGGCCaa | 17 | 143 | NI-NI-NG-NN-NI-NI-NG-NN-NG-HD-HD-HD-NI-NN-NN-HD-HD |
|  | 102877 | ctGCCCCATACCCACTTCcc | 16 | 144 | NN-HD-HD-HD-HD-NI-NG-NI-HD-HD-HD-NI-HD-NG-NG-HD |

TABLE 4-continued

TALEN pairs that recognize the +55 BCL11A enhancer region

| Sample | SBS # | target 5'->3' | # of RVDs | SEQ ID NO: | N->C RVD Sequence |
|---|---|---|---|---|---|
| 2 | 102878 | atTCTAGGAAGGGAAGTGGgt | 17 | 145 | NG-HD-NG-NI-NN-NN-NI-NI-NN-NN-NN-NI-NI-NN-NG-NN-NK |
|  | 102879 | gtACCAGGAAGGCAATGGGct | 17 | 146 | NI-HD-HD-NI-NN-NN-NI-NI-NN-NN-HD-NI-NI-NG-NN-NN-NK |
| 3 | 102880 | gtGGGTATGGGGCAGCCCAtt | 17 | 147 | NN-NN-NN-NG-NI-NG-NN-NN-NN-NN-HD-NI-NN-HD-HD-HD-NI |
|  | 102881 | atTGCATCATCCTGGTACca | 16 | 148 | NG-NN-HD-NI-NG-HD-NI-NG-HD-HD-NG-NN-HD |
| 4 | 102882 | ctTCCTGGTACCAGGATGAtg | 17 | 149 | NG-HD-HD-NG-NN-NN-NG-NI-HD-HD-NI-NN-NN-NI-NG-NN-NI |
|  | 102883 | gtGGGGAGCTCACAGCCTCca | 17 | 150 | NN-NN-NN-NN-NI-NN-HD-NG-HD-NI-HD-NI-NN-HD-HD-NG-HD |
| 5 | 102884 | atGATGCAATGCTTGGAGGct | 17 | 151 | NN-NI-NG-NN-HD-NI-NI-NG-NN-HD-NG-NG-NN-NN-NI-NN-NK |
|  | 102885 | gtGTGCCCTGAGAAGGTGGgg | 17 | 152 | NN-NG-NN-HD-HD-NG-NN-NI-NN-NI-NI-NN-NN-NG-NN-NK |
| 6 | 102886 | atGCTTGGAGGCTGTGAGCtc | 17 | 153 | NN-HD-NG-NG-NN-NN-NI-NN-NN-HD-NG-NN-NG-NN-NI-NN-HD |
|  | 102887 | atCACAGGGTGTGCCCTGAga | 17 | 154 | HD-NI-HD-NI-NN-NN-NN-NG-NN-NG-NN-HD-HD-HD-NG-NN-NI |
| 7 | 102888 | ctCCCCACCTTCTCAGGGCac | 17 | 155 | HD-HD-HD-HD-NI-HD-HD-NG-NG-HD-NG-HD-NI-NN-NN-NN-HD |
|  | 102889 | ctGGACAGAGGGGTCCCACaa | 17 | 156 | NN-NN-NI-HD-NI-NN-NI-NN-NN-NN-NN-NG-HD-HD-HD-NI-HD |
| 8 | 102890 | ctTCTCAGGGCACACCCTGtg | 17 | 157 | NG-HD-NG-HD-NI-NN-NN-NN-HD-NI-HD-NI-HD-HD-HD-NG-NK |
|  | 102891 | ctGGGCTGGACAGAGGGGTcc | 17 | 158 | NN-NN-NN-NN-HD-NG-NN-NN-NI-HD-NI-NN-NI-NN-NN-NN-NG |
| 9 | 102892 | ctGTGATCTTGTGGGACCcc | 16 | 159 | NN-NG-NN-NI-NG-HD-NG-NG-NN-NG-NN-NN-NN-NI-HD-HD |
|  | 102893 | atGCACACCCAGGCTGGGct | 16 | 160 | NN-HD-NI-HD-NI-HD-HD-HD-NI-NN-NN-HD-NG-NN-NN-NK |
| 10 | 102894 | ctTGTGGGACCCCTCTGTCca | 17 | 161 | NG-NN-NG-NN-NN-NN-NI-HD-HD-HD-HD-NG-HD-NG-NN-NG-HD |

TABLE 4 -continued

TALEN pairs that recognize the +55 BCL11A enhancer region

| Sample | SBS # | target 5'->3' | # of RVDs | SEQ ID NO: | N->C RVD Sequence |
|---|---|---|---|---|---|
|  | 102895 | gtGCCGACCAAGCACACAAga | 17 | 162 | NN-HD-HD-NN-NI-HD-HD-NI-NI-NN-HD-NI-HD-NI-HD-NI-NI |
| 11 | 102896 | ctGTCCAGCCCAGCCTGGGtg | 17 | 163 | NN-NG-HD-HD-NI-NN-HD-HD-HD-NI-NN-HD-HD-NG-NN-NN-NK |
|  | 102897 | atCAGTGCCGACCAAGCACac | 17 | 164 | HD-NI-NN-NG-NN-HD-HD-NN-NI-HD-HD-NI-NI-NN-HD-NI-HD |
| 12 | 102898 | ctGGGTGTGCATCTTGTGTgc | 17 | 165 | NN-NN-NN-NG-NN-NN-NN-HD-NI-NG-HD-NG-NG-NN-NG-NN-NG |
|  | 102899 | ctACCGCGACCCCTATCAGtg | 17 | 166 | NI-HD-HD-NN-HD-NN-NI-HD-HD-HD-HD-NG-NI-NG-HD-NI-NK |
| 13 | 102902 | gtAGGGAGTTGTCGGCACAca | 17 | 167 | NI-NN-NN-NN-NI-NN-NG-NG-NN-NG-HD-NN-NN-HD-NI-HD-NI |
|  | 102903 | ttGGGGACCGCTCACAGGAca | 17 | 168 | NN-NN-NN-NN-NI-HD-HD-NN-HD-NG-HD-NI-HD-NI-NN-NN-NI |
| 14 | 102904 | ctGCTGCATGTCCTGTGAgc | 16 | 169 | NN-HD-NG-NN-HD-NI-NG-NN-NG-HD-HD-NG-NN-NG-NN-NI |
|  | 102905 | ctGAAGGCTGGGCACAGCCtt | 17 | 170 | NN-NI-NI-NN-NN-HD-NG-NN-NN-NN-HD-NI-HD-NI-NN-HD-HD |
| 15 | 102906 | gtCCCCAAGGCTGTGCCCAgc | 17 | 171 | HD-HD-HD-HD-NI-NI-NN-NN-HD-NG-NN-NG-NN-HD-HD-HD-NI |
|  | 102907 | ctGTCAGAAGAGGCCCTGGac | 17 | 172 | NN-NG-HD-NI-NN-NI-NI-NN-NI-NN-NN-HD-HD-HD-NG-NN-NK |
| 16 | 102912 | ttCTGACAGGCCCTGCTGGtt | 17 | 173 | HD-NG-NN-NI-HD-NI-NN-NN-HD-HD-HD-NG-NN-HD-NG-NN-NK |
|  | 102913 | gtGGTGCGTGGAGATAATGcc | 17 | 174 | NN-NN-NG-NN-HD-NN-NG-NN-NN-NI-NN-NI-NG-NI-NI-NG-NK |
| 17 | 102914 | ctGCTGGTTATCACTGTTGgc | 17 | 175 | NN-HD-NG-NN-NN-NG-NG-NI-NG-HD-NI-HD-NG-NN-NG-NG-NK |
|  | 102915 | ctGGGCACAGAAGTGGTGCgt | 17 | 176 | NN-NN-NN-HD-NI-HD-NI-NN-NI-NI-NN-NG-NN-NN-NG-NN-HD |
| 18 | 102916 | ttGGCATTATCTCCACGCAcc | 17 | 177 | NN-NN-HD-NI-NG-NG-NI-NG-HD-NG-HD-HD-NI-HD-NN-HD-NI |
|  | 102917 | gtGACCCAGCAGCCCTGGGca | 17 | 178 | NN-NI-HD-HD-HD-NI-NN-HD-NI-NN-HD-HD-HD-NG-NN-NN-NK |
| 19 | 102918 | atCTCCACGCACCACTTCTgt | 17 | 179 | HD-NG-HD-HD-NI-HD-NN-HD-NI-HD-HD-NI-HD-NG-NG-HD-NG |

TABLE 4-continued

TALEN pairs that recognize the +55 BCL11A enhancer region

| Sample | SBS # | target 5'->3' | # of RVDs | SEQ ID NO: | N->C RVD Sequence |
|---|---|---|---|---|---|
|  | 102919 | ctCCTTAAGGTGACCCAGCag | 17 | 180 | HD-HD-NG-NG-NI-NI-NN-NN-NG-NN-NI-HD-HD-HD-NI-NN-HD |
| 20 | 102920 | gtGCCCAGGGCTGCTGGGTca | 17 | 181 | NN-HD-HD-HD-NI-NN-NN-NN-HD-NG-NN-HD-NG-NN-NN-NN-NG |
|  | 102921 | ctATGTAGACGGGTGTGTGgc | 17 | 182 | NI-NG-NN-NG-NI-NN-NI-HD-NN-NN-NN-NG-NN-NN-NG-NK |
| 21 | 102922 | gtCACCTTAAGGAGCCACAca | 17 | 183 | HD-NI-HD-HD-NG-NG-NI-NI-NN-NN-NI-NN-HD-HD-NI-HD-NI |
|  | 102923 | gtCAGACCCCAAGCAGGAAgg | 17 | 184 | HD-NI-NN-NI-HD-HD-HD-HD-NI-NI-NN-HD-NI-NN-NN-NI-NI |

Figure 9:
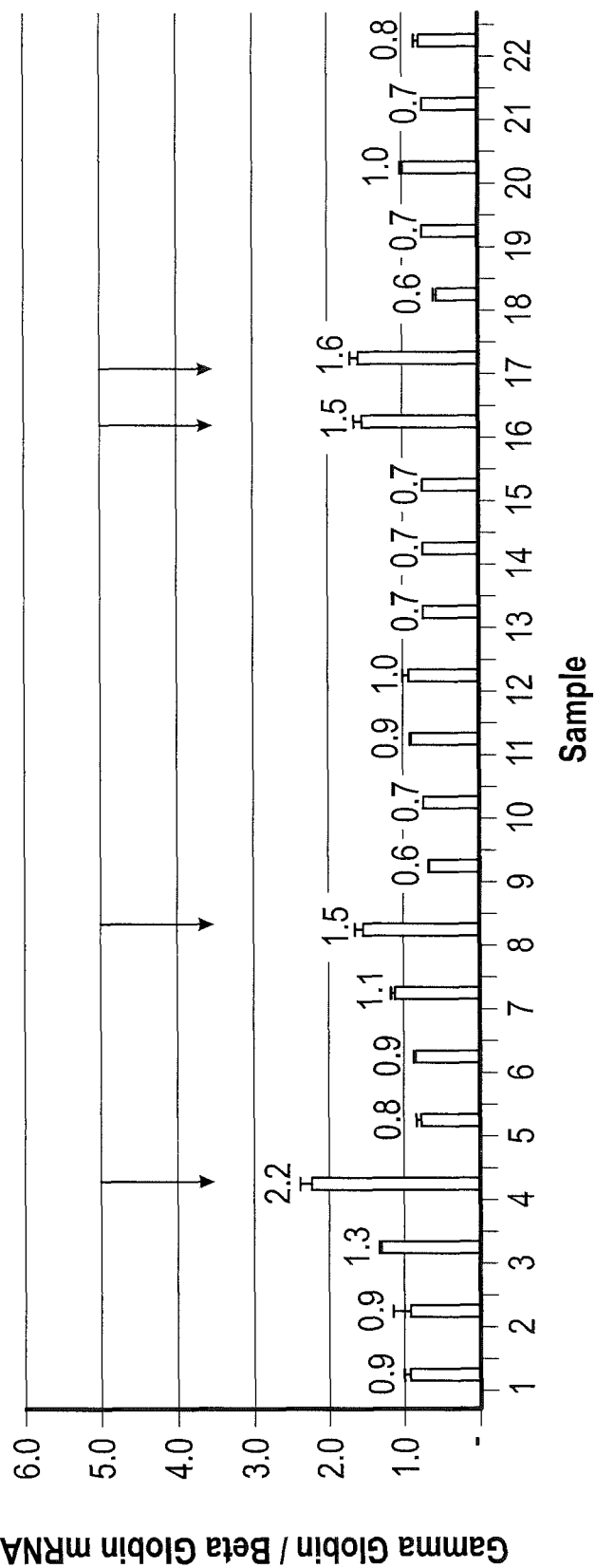
FIG. 9 shows the results from a Taqman® analysis as described in FIG. 4 where a series of TALENs were made to target the +55 region of the BCL11A enhancer. In this set of experiments, the levels of beta globin and gamma globin were characterized, and thus the data depicted is the ratio of gamma to beta and compared to the same ratio in control treated cells (which, in this experiment, was 0.8). The data confirm that mutations generated at specific positions within the +55 region can increase relative gamma globin expression (see arrows).
Figure 10:
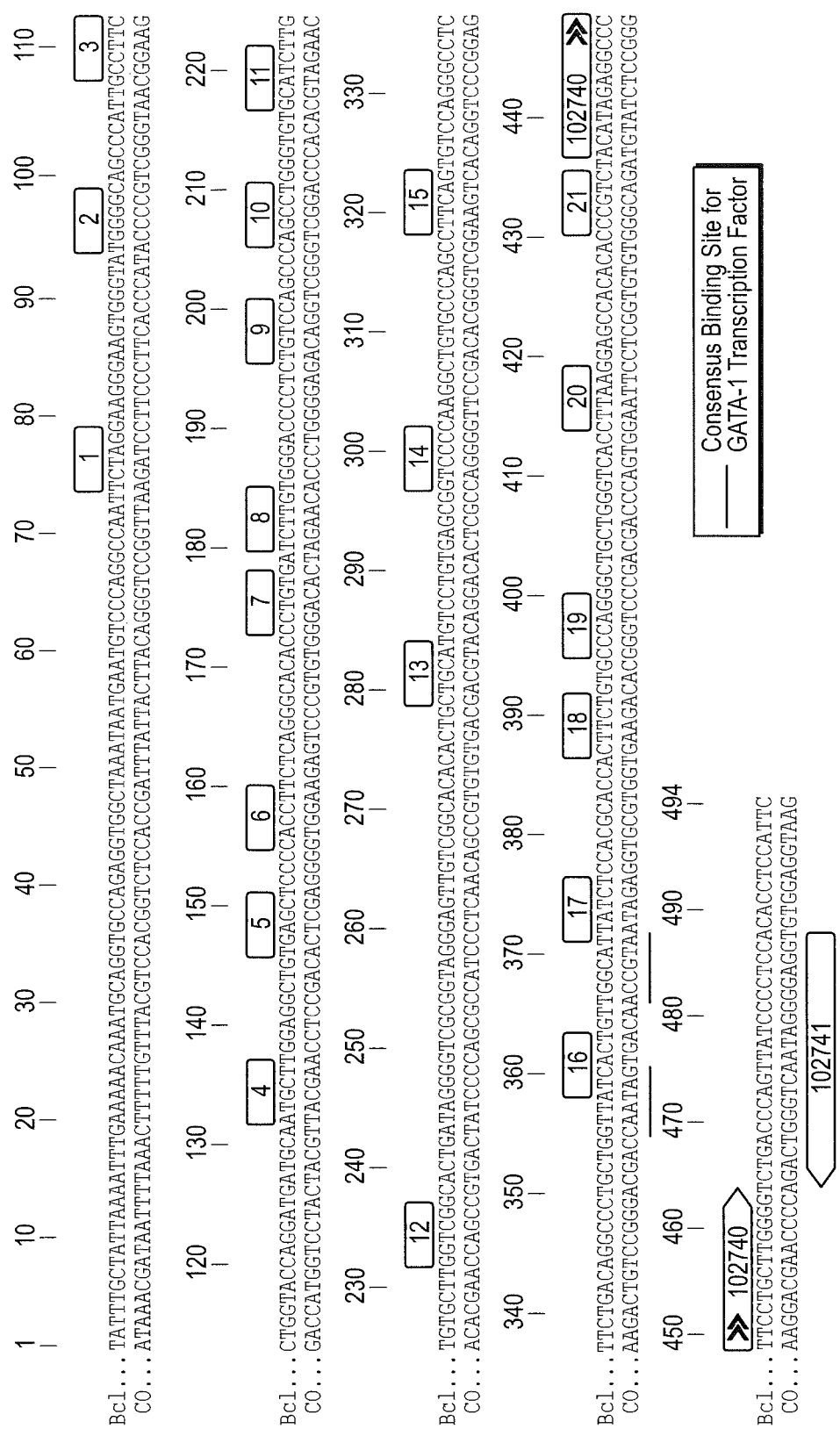
FIG. 10 is a representation of the cleavage sites of the +55 enhancer region specific TALENs as shown in FIG. 9. The sequence shown is the double stranded form of the DNA sequence encompassing the +55 region of the BCL11A enhancer (SEQ ID NO:254). The numbers that highlight short regions of nucleotides indicate the likely cleavage sites induced by the TALEN samples listed in FIG. 10. Also indicated in FIG. 10 are two matches to the consensus binding site for the GATA-1 transcription factor.

The TALENs were introduced into CD34+ cells as described above and the cells were induced to differentiate into erythroid cells as described above. Taqman® analysis was performed as described and several sites identified that caused an increase in relative gamma expression (FIG. 9). The cleavage sites are displayed in FIG. 10. All designs shown in Table 4 were active. Interestingly, one of the TALEN pairs which drove an increase in gamma globin mRNAs cleaves at another GATA-1 consensus sequence (cleavage site 17 on FIG. 10).

Example 6

ZFNs Directed to the +55 DNAse I Hypersensitive Site in BCL11A

Similar to Example 4, a set of ZFNs were made to probe the +55 DNAse I hypersensitive region. The ZFNs are shown below in Table 6.

TABLE 6

+55 enhancer region specific ZFNs: designs and targets

| SBS # (target site, 5'-3') | Design | | | | | |
|---|---|---|---|---|---|---|
|  | F1 | F2 | F3 | F4 | F5 | F6 |
| 46156 (tgGCCTGGG ACATTCATTA Tttagccac; SEQ ID NO: 232) | TSSNRKT (SEQ ID NO: 133) | AACNRNA (SEQ ID NO: 185) | WKCQLPI (SEQ ID NO: 186) | DRSNLTR (SEQ ID NO: 187) | RSDHLSQ (SEQ ID NO: 188) | DSSTRKK (SEQ ID NO: 189) |
| 46158 (tcTAGGAAG GGAAGTGGGT Atggggcag; SEQ ID NO: 233) | QSGALAR (SEQ ID NO: 95) | RKYYLAK (SEQ ID NO: 190) | RSDNLSV (SEQ ID NO: 191) | RSAHLSR (SEQ ID NO: 109) | QSGNLAR (SEQ ID NO: 192) | ARWSLGK (SEQ ID NO: 193) |
| 46163 (taGAATTGG CCTGGGACAT Tcattattt; SEQ ID NO: 234) | WKCQLPI (SEQ ID NO: 186) | DRSNLTR (SEQ ID NO: 187) | RSDHLSQ (SEQ ID NO: 188) | DSSTRKK (SEQ ID NO: 189) | RPYTLRL (SEQ ID NO: 119) | QSGNLAR (SEQ ID NO: 192) |
| 46164 (gaAGGGAAG TGGGTATGGG Gcagcccat; SEQ ID NO: 235) | RSAHLSR (SEQ ID NO: 109) | RSDALTQ (SEQ ID NO: 139) | TSGHLSR (SEQ ID NO: 103) | RSDALAR (SEQ ID NO: 130) | QSGNLAR (SEQ ID NO: 192) | RQEHRVA (SEQ ID NO: 194) |

TABLE 6-continued

+55 enhancer region specific ZFNs: designs and targets

| SBS # (target site, 5'-3') | Design | | | | | |
|---|---|---|---|---|---|---|
| | F1 | F2 | F3 | F4 | F5 | F6 |
| 46180 (tcATCCTGg TACCAGGAAG GCaatgggc; SEQ ID NO: 236) | DRSHLTR (SEQ ID NO: 116) | QSGNLAR (SEQ ID NO: 192) | RSDSLSA (SEQ ID NO: 195) | DNSNRIK (SEQ ID NO: 196) | RSDVLSE (SEQ ID NO: 137) | SPSSRRT (SEQ ID NO: 197) |
| 46181 (gcAATGCTt GGAGGCTGTG AGctcccca; SEQ ID NO: 237) | RSDNLAR (SEQ ID NO: 198) | WQSSLIV (SEQ ID NO: 199) | DRSHLTR (SEQ ID NO: 116) | QSGHLSR (SEQ ID NO: 141) | QSSDLSR (SEQ ID NO: 128) | LKWNLRT (SEQ ID NO: 200) |
| 46188 (ccTGAGAAG GTGGGGAGCT Cacagcctc; SEQ ID NO: 238) | PCRYRLD (SEQ ID NO: 201) | RSANLTR (SEQ ID NO: 202) | RSDHLSR (SEQ ID NO: 98) | TSGHLSR (SEQ ID NO: 103) | QSGNLAR (SEQ ID NO: 192) | QKPWRTP (SEQ ID NO: 203) |
| 46189 (acACCCTGt GATCTTGTGG GAcccctct; SEQ ID NO: 239) | QSSHLTR (SEQ ID NO: 204) | RSDALAR (SEQ ID NO: 130) | YRSSLKE (SEQ ID NO: 205) | TSGNLTR (SEQ ID NO: 93) | RSDTLSA (SEQ ID NO: 206) | DKSTRTK (SEQ ID NO: 207) |
| 46208 (ggGCTGGAc AGAGGGGTCc cacaagatc; SEQ ID NO: 240) | DRSALAR (SEQ ID NO: 208) | RSDHLSR (SEQ ID NO: 98) | QGAHLGA (SEQ ID NO: 209) | QSSHLTR (SEQ ID NO: 204) | QSSDLTR (SEQ ID NO: 210) | N/A |
| 46209 (gcCTGGGTG TGCATCTTGT Gtgcttggt; SEQ ID NO: 241) | RSDSLLR (SEQ ID NO: 211) | SASARWW (SEQ ID NO: 212) | TQSNLRM (SEQ ID NO: 213) | RNASRTR (SEQ ID NO: 214) | DRSHLTR (SEQ ID NO: 116) | RLDWLPM (SEQ ID NO: 106) |
| 46216 (caGGCTGGG CTGGAcAGAG GGgtcccac; SEQ ID NO: 242) | RSDHLSR (SEQ ID NO: 98) | QGAHLGA (SEQ ID NO: 209) | QSSHLTR (SEQ ID NO: 204) | QSSDLTR (SEQ ID NO: 210) | RSDHLSQ (SEQ ID NO: 188) | DSSHRTR (SEQ ID NO: 86) |
| 46217 (gtGTGCATC TTGTGtGCTT GGtcggcac; SEQ ID NO: 243) | RSDHLSQ (SEQ ID NO: 188) | RRSDLKR (SEQ ID NO: 215) | RSDSLLR (SEQ ID NO: 211) | SASARWW (SEQ ID NO: 212) | TQSNLRM (SEQ ID NO: 213) | RNASRTR (SEQ ID NO: 214) |
| 46226 (gtGCCGACC AAGCACACAA Gatgcacac; SEQ ID NO: 244) | RSDNLST (SEQ ID NO: 216) | DNSNRIN (SEQ ID NO: 217) | QSGDLTR (SEQ ID NO: 90) | QSGNLHV (SEQ ID NO: 218) | DRSDLSR (SEQ ID NO: 219) | DSSTRRR (SEQ ID NO: 220) |
| 46228 (atAGGGGTc GCGGTAGGGA GTtgtcggc; SEQ ID NO: 245) | LKQNLDA (SEQ ID NO: 108) | RSAHLSR (SEQ ID NO: 109) | QSGALAR (SEQ ID NO: 95) | RSDDLTR (SEQ ID NO: 83) | LKQNLDA (SEQ ID NO: 108) | RSHHLKA (SEQ ID NO: 132) |

TABLE 6-continued

+55 enhancer region specific ZFNs: designs and targets

| SBS # (target site, 5'-3') | Design | | | | | |
|---|---|---|---|---|---|---|
| | F1 | F2 | F3 | F4 | F5 | F6 |
| 46229 (ccTATCAGt GCCGACCAAG CAcacaaga; SEQ ID NO: 246) | QSGDLTR (SEQ ID NO: 90) | QSGNLHV (SEQ ID NO: 218) | DRSDLSR (SEQ ID NO: 219) | DSSTRRR (SEQ ID NO: 220) | RSDNLSE (SEQ ID NO: 81) | TSSNRKT (SEQ ID NO: 133) |
| 46230 (tcGCGGTAg GGAGTTGTCG GCacacact; SEQ ID NO: 247) | DRSHLSR (SEQ ID NO: 221) | DRSALAR (SEQ ID NO: 208) | TSGSLSR (SEQ ID NO: 124) | QAGHLAK (SEQ ID NO: 222) | QSGALAR (SEQ ID NO: 95) | RSDDLTR (SEQ ID NO: 83) |
| 46240 (ctCACAGGa CATGCAGCAG TGtgtgccg; SEQ ID NO: 248) | RSDSLSV (SEQ ID NO: 223) | QSGDLTR (SEQ ID NO: 90) | QSGDLTR (SEQ ID NO: 90) | TSHNRNA (SEQ ID NO: 224) | RSDHLSQ (SEQ ID NO: 188) | DNSNRIN (SEQ ID NO: 217) |
| 46241 (tcCCCAAGG CTGTGCCCag ccttcagtg; SEQ ID NO: 249) | DRSNLSS (SEQ ID NO: 225) | RSHSLLR (SEQ ID NO: 226) | QSSDLSR (SEQ ID NO: 128) | RSDNLSV (SEQ ID NO: 191) | DNRDRIK (SEQ ID NO: 227) | N/A |
| 46246 (gtGTGGCTc CTTAAGGTGA CCcagcagc; SEQ ID NO: 250) | ASKTRTN (SEQ ID NO: 228) | RNASRTR (SEQ ID NO: 214) | RSDNLSV (SEQ ID NO: 191) | YSSTRNS (SEQ ID NO: 229) | QSSDLSR (SEQ ID NO: 128) | RSDALAR (SEQ ID NO: 130) |
| 46247 (ccGTCTACA TAGAGgccct tcctgcttg; SEQ ID NO: 251) | RSDNLAR (SEQ ID NO: 198) | QSTPRNT (SEQ ID NO: 230) | WPDYLPT (SEQ ID NO: 231) | DRSALAR (SEQ ID NO: 208) | N/A | N/A |

The +55 region specific ZFNs were tested for cleavage activity using the Cel-I assay and found to be active in K562 cells. All designs shown in Table 6 were active and the ZFN-induced gene modification, described as % NHEJ (non-homologous end joining) found for each pair is listed below in Table 7.

TABLE 7

Cleavage activity of BCL11A + 55 enhancer region specific ZFN in K562 cells

| ZFN 1 (SBS#) | ZFN 2 (SBS#) | % NHEJ |
|---|---|---|
| 46158 | 46156 | 30.36 |
| 46164 | 46163 | 21.90 |
| 46181 | 46180 | 15.21 |
| 46189 | 46188 | 12.76 |
| 46209 | 46208 | 27.96 |
| 46217 | 46216 | 16.63 |
| 46228 | 46226 | 37.79 |
| 46230 | 46229 | 37.23 |
| 46241 | 46240 | 24.97 |
| 46247 | 46246 | 17.30 |
| GFP Transduction control | | 0.00 |

The CD34+ cells were transfected with the ZFN pairs as described for Example 4, and then differentiated into erythrocytes as above. The ZFNs shown in 6 bound to and modified the BCL11A+55 enhancer region.

Example 7

Increasing Activity of +58 Specific ZFN Pairs

The ZFNs targeting the +58 region were further refined by shifting the target sequences, altering finger identity and using alternate linkers between the zinc finger DNA binding domain and the FokI cleavage domains.

ZFN pairs were made to target a sequence very close to the cleavage site of the 45843/45844 ZFN pair. The pairs are shown below in Table 8, and the location of their binding sites are shown in FIG. 12A.

TABLE 8

| SBS # (target site, 5'-3') | Design | | | | | | linker |
|---|---|---|---|---|---|---|---|
| | F1 | F2 | F3 | F4 | F5 | F6 | |
| 46880 caCAGGCTC CAGGAAGGg tttggcctct (SEQ ID NO: 73) | RSDHLTQ (SEQ ID NO: 125) | QSGHLAR (SEQ ID NO: 126) | QKGTLGE (SEQ ID NO: 127) | QSSDLSR (SEQ ID NO: 128) | RRDNLHS (SEQ ID NO: 113) | N/A | L7a |
| 47923 caCAGGCTC CAGGAAGGg tttggcctct (SEQ ID NO: 73) | RSDHLTQ (SEQ ID NO: 125) | QSGHLAR (SEQ ID NO: 126) | QKGTLGE (SEQ ID NO: 127) | QSSDLSR (SEQ ID NO: 128) | RRDNLHS (SEQ ID NO: 113) | N/A | L0 |
| 50679 caCAGGCTC CAGGAAGGg tttggcctct (SEQ ID NO: 73) | RSDHLTQ (SEQ ID NO: 125) | QSGHLAR (SEQ ID NO: 126) | QKGTLGE (SEQ ID NO: 127) | QSSDLSR (SEQ ID NO: 128) | RRDNLHS (SEQ ID NO: 113) | N/A | L0[-1] |
| 50680 caCAGGCTC CAGGAAGGg tttggcctct (SEQ ID NO: 73) | RSDHLTQ (SEQ ID NO: 125) | QSGHLAR (SEQ ID NO: 126) | QKGTLGE (SEQ ID NO: 127) | QSSDLSR (SEQ ID NO: 128) | RRDNLHS (SEQ ID NO: 113) | N/A | L0[-2] |
| 46923 aaGCAACTG TTAGCttGC ACTAgactag (SEQ ID NO: 72) | QKGTLGE (SEQ ID NO: 127) | QSGSLTR (SEQ ID NO: 252) | TGYNLTN (SEQ ID NO: 120) | TSGSLTR (SEQ ID NO: 121) | QHQVLVR (SEQ ID NO: 122) | QNATRTK (SEQ ID NO: 123) | L7e4 |
| 46999 caCAGGCTC CAGGAAGGg tttggcctct (SEQ ID NO: 73) | RSDHLTQ (SEQ ID NO: 125) | QSGHLAR (SEQ ID NO: 126) | QKGTLGE (SEQ ID NO: 127) | QSSDLSR (SEQ ID NO: 128) | RRDNLHS (SEQ ID NO: 113) | N/A | L7c5 |
| 45844 tcACAGGCT CCAGGAAGG GTttggcctc (SEQ ID NO: 71) | LRHHLTR (SEQ ID NO: 112) | RRDNLHS (SEQ ID NO: 113) | RSDHLSN (SEQ ID NO: 114) | DSRSRIN (SEQ ID NO: 115) | DRSHLTR (SEQ ID NO: 116) | QSGTRKT (SEQ ID NO: 117) | L7a |
| 47021 tcACAGGCT CCAGGAAGG GTttggcctc (SEQ ID NO: 71) | LRHHLTR (SEQ ID NO: 112) | RRDNLHS (SEQ ID NO: 113) | RSDHLSN (SEQ ID NO: 114) | DSRSRIN (SEQ ID NO: 115) | DRSHLTR (SEQ ID NO: 116) | QSGTRKT (SEQ ID NO: 117) | L7c5 |
| 45843 aaGCAACTG TTAGCTTGC ACtagactag (SEQ ID NO: 72) | DQSNLRA (SEQ ID NO: 118) | RPYTLRL (SEQ ID NO: 119) | TGYNLTN (SEQ ID NO: 120) | TSGSLTR (SEQ ID NO: 121) | QHQVLVR (SEQ ID NO: 122) | QNATRTK (SEQ ID NO: 123) | L7a |

TABLE 8-continued

ZFNs targeting the +58 enhancer region

| SBS # (target site, 5'-3') | Design | | | | | | linker |
|---|---|---|---|---|---|---|---|
| | F1 | F2 | F3 | F4 | F5 | F6 | |
| 46801 aaAGCAACt GTTAGCTTG CACtagacta (SEQ ID NO: 74) | DQSNLRA (SEQ ID NO: 118) | RPYTLRL (SEQ ID NO: 119) | SGYNLEN (SEQ ID NO: 253) | TSGSLTR (SEQ ID NO: 121) | DQSNLRA (SEQ ID NO: 118) | AQCCLFH (SEQ ID NO: 129) | L7a |
| 46786 aaAGCAACt GTTAGCTTG CACtagacta (SEQ ID NO: 74) | DQSNLRA (SEQ ID NO: 118) | RPYTLRL (SEQ ID NO: 119) | SGYNLEN (SEQ ID NO: 253) | TSGSLTR (SEQ ID NO: 121) | DQSNLRA (SEQ ID NO: 118) | AQCCLFH (SEQ ID NO: 129) | L0 |
| 46934 aaAGCAACt GTTAGCTTG CACtagacta (SEQ ID NO: 74) | DQSNLRA (SEQ ID NO: 118) | RPYTLRL (SEQ ID NO: 119) | SGYNLEN (SEQ ID NO: 253) | TSGSLTR (SEQ ID NO: 121) | DQSNLRA (SEQ ID NO: 118) | AQCCLFH (SEQ ID NO: 129) | L7c5 |
| 46816 aaAGCAACt GTTAGCTTG CACtagacta (SEQ ID NO: 74) | DQSNLRA (SEQ ID NO: 118) | RPYTLRL (SEQ ID NO: 119) | SGYNLEN (SEQ ID NO: 253) | TSGSLTR (SEQ ID NO: 121) | DQSNLRA (SEQ ID NO: 118) | AQCCLFH (SEQ ID NO: 129) | L8c4 |
| 50670 aaAGCAACt GTTAGCTTG CACtagacta (SEQ ID NO: 74) | DQSNLRA (SEQ ID NO: 118) | RPYTLRL (SEQ ID NO: 119) | SGYNLEN (SEQ ID NO: 253) | TSGSLTR (SEQ ID NO: 121) | DQSNLRA (SEQ ID NO: 118) | AQCCLFH (SEQ ID NO: 129) | L0[+9] |
| 50671 aaAGCAACt GTTAGCTTG CACtagacta (SEQ ID NO: 74) | DQSNLRA (SEQ ID NO: 118) | RPYTLRL (SEQ ID NO: 119) | SGYNLEN (SEQ ID NO: 253) | TSGSLTR (SEQ ID NO: 121) | DQSNLRA (SEQ ID NO: 118) | AQCCLFH (SEQ ID NO: 129) | L0[+7] |
| 50672 aaAGCAACt GTTAGCTTG CACtagacta (SEQ ID NO: 74) | DQSNLRA (SEQ ID NO: 118) | RPYTLRL (SEQ ID NO: 119) | SGYNLEN (SEQ ID NO: 253) | TSGSLTR (SEQ ID NO: 121) | DQSNLRA (SEQ ID NO: 118) | AQCCLFH (SEQ ID NO: 129) | L0[+5] |
| 48117 aaAGCAACt GTTAGCTTG CACtagacta (SEQ ID NO: 74) | DQSNLRA (SEQ ID NO: 118) | RPYTLRL (SEQ ID NO: 119) | SGYNLEN (SEQ ID NO: 253) | TSGSLTR (SEQ ID NO: 121) | DQSNLRA (SEQ ID NO: 118) | AQCCLFH (SEQ ID NO: 129) | L7c5 |
| 50674 aaAGCAACt GTTAGCTTG CACtagacta (SEQ ID NO: 74) | DQSNLRA (SEQ ID NO: 118) | RPYTLRL (SEQ ID NO: 119) | SGYNLEN (SEQ ID NO: 253) | TSGSLTR (SEQ ID NO: 121) | DQSNLRA (SEQ ID NO: 118) | AQCCLFH (SEQ ID NO: 129) | L0 [+11] |
| 50676 aaAGCAACt GTTAGCTTG CACtagacta (SEQ ID NO: 74) | DQSNLRA (SEQ ID NO: 118) | RPYTLRL (SEQ ID NO: 119) | SGYNLEN (SEQ ID NO: 253) | TSGSLTR (SEQ ID NO: 121) | DQSNLRA (SEQ ID NO: 118) | AQCCLFH (SEQ ID NO: 129) | L0[+7] |

TABLE 8-continued

ZFNs targeting the +58 enhancer region

| SBS # (target site, 5'-3') | Design | | | | | | |
|---|---|---|---|---|---|---|---|
| | F1 | F2 | F3 | F4 | F5 | F6 | linker |
| 48037 aaAGCAACt GTTAGCTTG CACtagacta (SEQ ID NO: 74) | DQSNLRA (SEQ ID NO: 118) | RPYTLRL (SEQ ID NO: 119) | SGYNLEN (SEQ ID NO: 253) | TSGSLTR (SEQ ID NO: 121) | DQSNLRA (SEQ ID NO: 118) | AQCCLFH (SEQ ID NO: 129) | L7a |

Figure 12B:
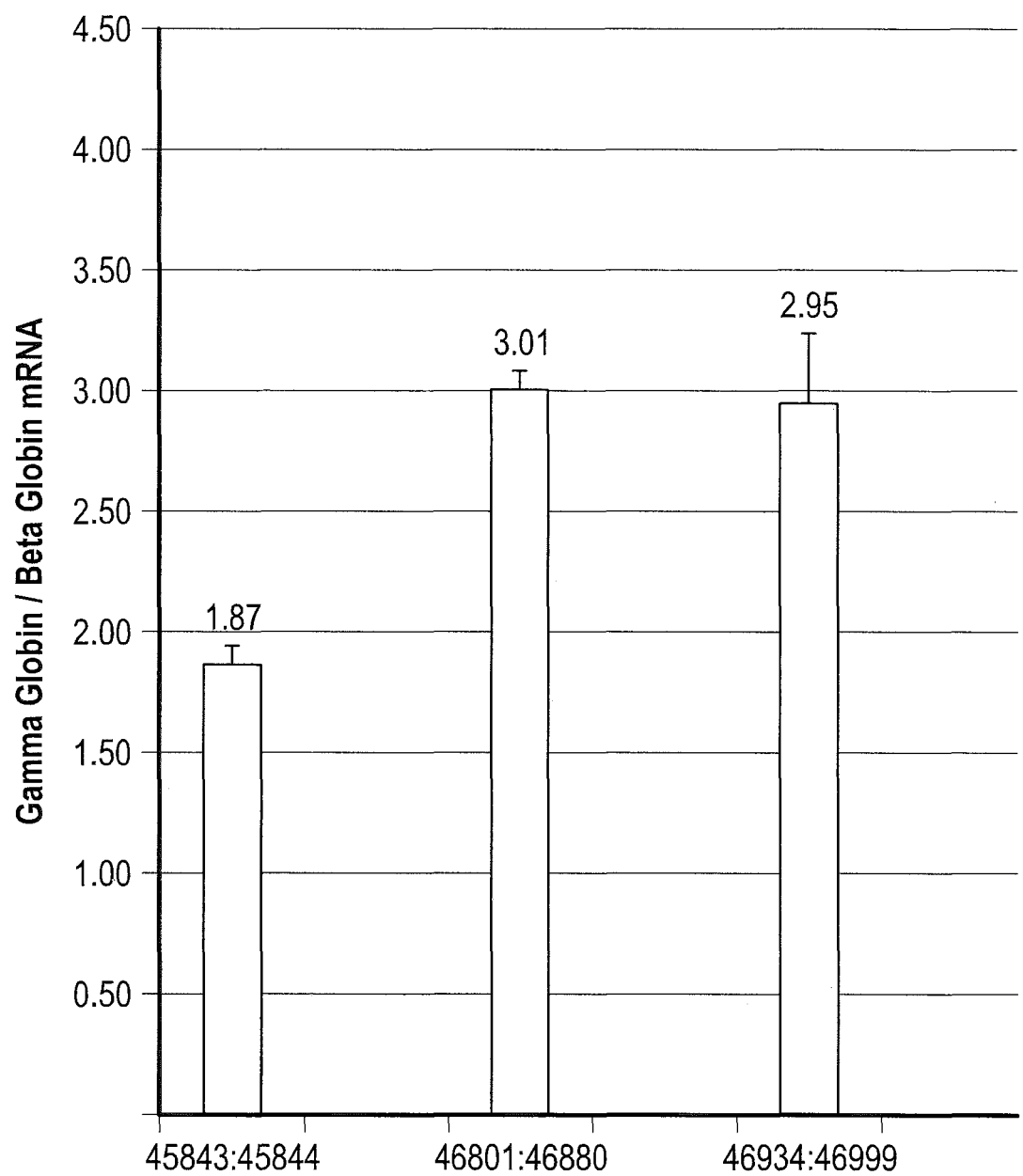
Figure 12C:
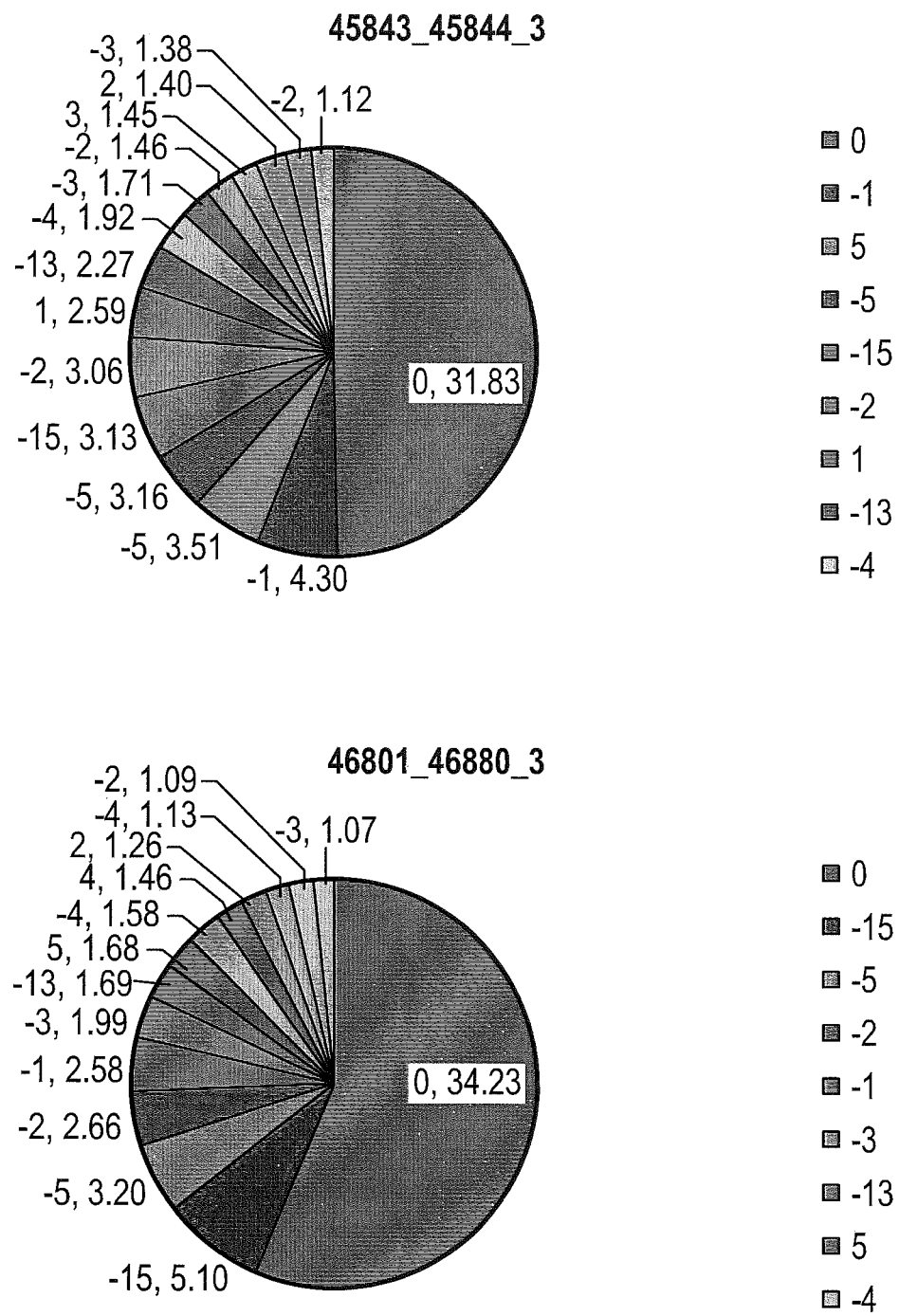

As can be seen in FIG. 12, the binding site of the new pairs is located one base pair closer to the center of the GATA-1 consensus sequence. All pairs were active for binding and cleaving their targets in the genome as gauged by an initial screen in K562 cells. mRNAs encoding the ZFNs were electroporated into CD34+ cells and then the cells were differentiated into the erythroid lineage as described in Example 2. To analyze relative gamma globin expression, the ratios of mRNAs encoding gamma globin and beta globin following ZFN treatment were determined by Taqman® analysis at 14 days following ZFN introduction. The results (FIG. 12B) demonstrated that the ZFN pairs targeting the shifted binding sites had a greater influence on the expression of gamma globin.

Next, the proteins were made with an alternate linker types to test the effect on the Bcl11a proteins. Similar sets of ZFNs were made that comprised the same helices in the same fingers but where each contained different linkers between the ZFP DNA binding domain and the FokI nuclease. For example, ZFNs 46801, 46786, 46816 and 46934 have the same ZFP DNA binding domain, but are linked to the nuclease domain using the L7a, L0, L8c4 and L7c5 linkers respectively. Similarly, ZFNs 45844 and 47021 have the same DNA binding domain, but 45844 has the L7a linker while 47021 uses the L7c5 linker. In addition, 46880, 47923, 50679 and 50680 have the same DNA binding domains, but 46880 uses the L7a linker; 47923 has the L7c5 linker; 50679 uses L0[−1] and 50680 has L0[−3]. The linkers are shown in FIG. 14 and FIG. 17.

Figure 13:
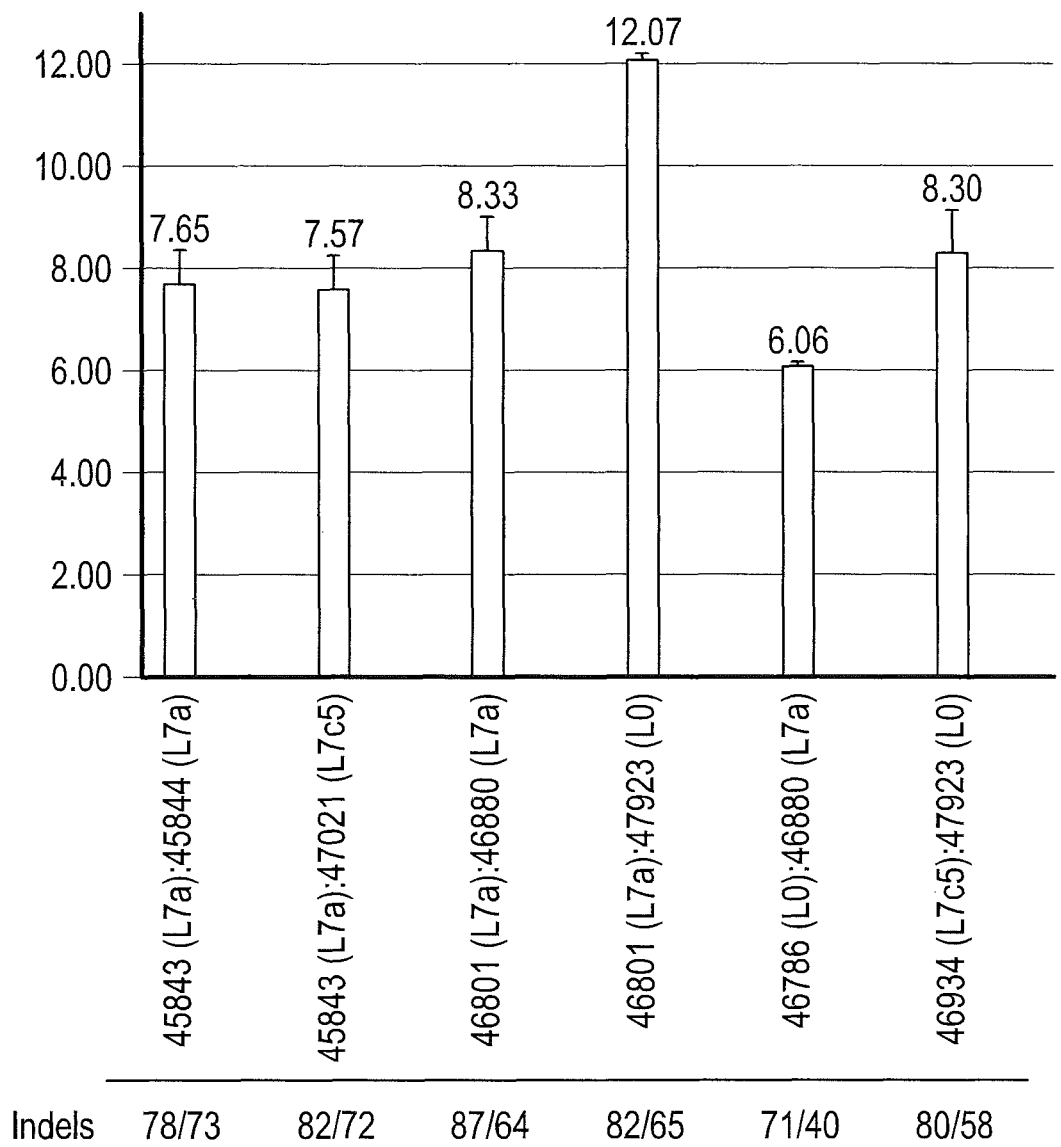
FIG. 13 demonstrates that altering the linker between the zinc finger and FokI moiety in ZFNs used for genome editing of the BCL11A enhancer affects fetal globin levels following in vitro erythropoiesis despite comparable levels disrupted chromatids. Human HSPCs were electroporated with the indicated ZFNs (the linker used in each ZFN monomer is indicated in parentheses), and immediately prior and following in vitro erythroid differentiation, the % of disrupted alleles was measured (shown below each sample in "X/Y" form, with the first number corresponding to % of non-wild-type indels following electroporation, and the second number show results following 14 days of in vitro erythroid differentiation). Whole mRNA was harvested and the levels of fetal globin (normalized to alpha globin) were measured.

As shown in FIG. 13, the ZFNs were tested in various pairs where one set of pairs targeted the binding site typified by the one targeted by the 45843/45844 pair, and then a second set typified by the one targeted by 46801/46880. The pairs tested are shown below in Table 9 as follows along with the percent cleavage (NHEJ) as measured by sequence analysis at either Day 0 (D0) or Day 14 (D14). Each data point is a mean of three replicates.

TABLE 9

Effect of Linker on ZFN cleavage activity

| Pair | Linkers | Target type | NHEJ, D 0 | NHEJ, D 14 | HGB/HBA ratio |
|---|---|---|---|---|---|
| 45843/45844 | L7a/L7a | 45843/45844 | 78% | 73% | 7.65 |
| 45843/47021 | L7a/L7c5 | 45843/45844 | 82% | 72% | 7.57 |
| 46801/46880 | L7a/L7a | 46801/46880 | 87% | 64% | 8.33 |
| 46801/47923 | L7a/L0 | 46801/46880 | 82% | 65% | 12.07 |
| 46786/46880 | L0/L7a | 46801/46880 | 71% | 40% | 6.06 |
| 46934/47923 | L7c5/L0 | 46801/46880 | 80% | 58% | 8.3 |
| GFP | | | | | 2.71 |

Additional tests were designed to measure the number of indel containing edits that destroyed the GATA site in the target. Shown in Table 10 below are combinations of ZFNs with various linkers and the effect the linkers have in increasing the percent of indels overall and the increase in indels that result in the loss of the GATA binding site.

TABLE 10

Exemplary linker activity

| Left ZFN | | Right ZFN | | % indel, | | % of no GATA/ |
|---|---|---|---|---|---|---|
| SBS# | Linker Type | SBS# | Linker Type | no GATA left | % total _indels | total indel |
| 50670 | L0 [+9] | 47923 | L0 | 28.0 | 30.8 | 0.91 |
| 50671 | L0 [+7] | | | 24.5 | 26.7 | 0.92 |
| 50672 | L0 [+5] | | | 30.3 | 33.0 | 0.92 |
| 46801 | L7a | | | 27.6 | 30.4 | 0.91 |
| 46816 | L8c4 | | | 27.7 | 29.9 | 0.93 |
| 46934 | L7c5 | | | 43.8 | 47.8 | 0.92 |
| 50670 | L0 [+9] | 50679 | L0 [−1] | 30.1 | 32.6 | 0.92 |
| 50671 | L0 [+7] | | | 23.3 | 25.3 | 0.92 |
| 50672 | L0 [+5] | | | 31.1 | 34.2 | 0.91 |
| 46801 | L7a | | | 16.1 | 18.0 | 0.89 |
| 46816 | L8c4 | | | 33.8 | 36.2 | 0.93 |
| 46934 | L7c5 | | | 23.7 | 25.4 | 0.94 |
| 50670 | L0 [+9] | 50680 | L0 [−2] | 16.9 | 18.1 | 0.94 |
| 50671 | L0 [+7] | | | 16.9 | 17.9 | 0.94 |

TABLE 10-continued

| | Exemplary linker activity | | | | | |
|---|---|---|---|---|---|---|
| Left ZFN | | Right ZFN | | % indel, | | % of no GATA/ |
| SBS# | Linker Type | SBS# | Linker Type | no GATA left | % total _indels | total indel |
| 50672 | L0 [+5] | | | 23.2 | 24.9 | 0.93 |
| 46801 | L7a | | | 24.2 | 26.0 | 0.93 |
| 46816 | L8c4 | | | 21.3 | 23.2 | 0.92 |
| 46934 | L7c5 | | | 25.1 | 27.0 | 0.93 |
| 46801 | | 47923 | | 16.5 | 19.1 | 0.86 |
| | | | GFP | 1.4 | 0.8 | 1.64 |

As can be seen in the table above, refining of the original pair, 46801 (L7a)/47923 (L0), whose activity was measured in this experiment to be 19% overall indel formation, with 86% of those measured indels having a destroyed GATA binding site, can lead to an overall increased in cleavage (indel) activity, and an overall increase in the percent of indels that lead to destruction of GATA. See for example 46934(L7c5)/47923 (L0) where 47.8% total indels were observed and 92% of those indels had a destroyed GATA site. These and other linkers described (see FIG. 17) may be incorporated into the ZFNs to increase and/or refine activity.

Thus, alternate linkers may be used with the ZFN pairs described herein to cleave Bcl11a and increase in gamma hemoglobin relative to alpha hemoglobin.

Example 8

In Vivo Administration

Compositions including cells (e.g., HSCs and/or RBC precursor cells), proteins (e.g., nucleases) and/or polynucleotides (e.g., encoding nucleases) as described herein are administered to a subject, for example a subject with a hemoglobinopathy, essentially as described in U.S. Pat. Nos. 7,837,668; 8,092,429; U.S. Patent Publication No. 20060239966; U.S. Pat. Nos. 6,180,613; 6,503,888 and/or 6,998,118 and 7,101,540 to provide therapy for a subject in need thereof.

In addition, the cells are studied for use in large scale production of edited LT-HSC. Bulk CD34+ cells are pre-stimulated with cytokines comprising Stemspan™ CC110, Flt-3 ligand, SCF, and TPO and all combinations thereof in concentrations from 10 ng/mL to 1000 ng/mL. Pre-stimulation may require exposure times of 24, up to 48 and up to 72 hours. For clinical-scale HSPC transfection, any high capacity system may be used (e.g. Maxcyte GT Flow Transfection System).

For ex vivo therapies, edited cells (e.g., HSCs) are subjected to colony forming assays in methylcellulose medium to confirm the frequency of pluripotent cells and to verify that the colonies possess the desired genetic editing at the expected frequencies. The methylcellulose studies are carried out using methods known in the art (see for example Keller et at (1993) *Mol Cell Bio* 13(1):473).

To further ensure the engraftability of the BLC11a-edited cells (e.g., HSC), the cells are engrafted into a relevant mouse model and/or a non-human primate model. Engraftment in these animals is done according to methods known in the art. See, for example Holt, et al. (2010) *Nat Biotech* 28, 839-847, Ho et al (2009) *Retrovirology* 6:65 and Peterson et al (2013) *J. Med Primatol* 42: 237. Engraftment with (1020 cGy irradiation) or without (200 cGy irradiation) myeloablative preconditioning is used to investigate optimum engraftment and expansion conditions for stem cell transplantation.

Example 9

In Vivo Administration and Engraftment

As described above, CD34+ human cells were treated with mRNAs encoding the +55 enhancer specific ZFNs and then engrafted into NSG mice. CD34+ cells were obtained from healthy human volunteers. In some cases, CD34+ mobilization strategies were done, using either G-CSF (Neupogen®) or G-CSF+ Plerixafor (Mozobil®) prior to apheresis. The G-CSF was administered daily for the four days prior to apheresis according to manufacturer's instructions, and if Plerixafor was used, it was administered on the final evening prior to harvest, again according to manufacturer's instructions. The apheresis was performed by standard methods. CD34+ cells were enriched from the mobilized PBMC leukopaks using a Miltenyi CliniMACs system by standard methods and according to manufacturer's instructions.

Capped and poly-adenylated mRNAs encoding the ZFNs were synthesized using Ambion mMessage mMachine® T7 ultra kit as instructed by the manufacturer and then electroporated into the CD34+ cells using either a Maxcyte GT system or a BTX ECM830 electroporator, both according to manufacturer's instructions.

NOD.Cg-Prkdc$^{scid}$ Il2rg$^{tm1Wjl}$/SzJ mice were used to receive the CD34+ transplant. One day (16-24 hours) prior to implantation, the mice were subject to sublethal irradiation (300 RAD). The ZFN-treated CD34+ cells from above were transplanted into the irradiated mice through a tail vein injection, where 1 million cells in 0.5 mL PBS-0.1% BSA were given per mouse.

Figure 15A:
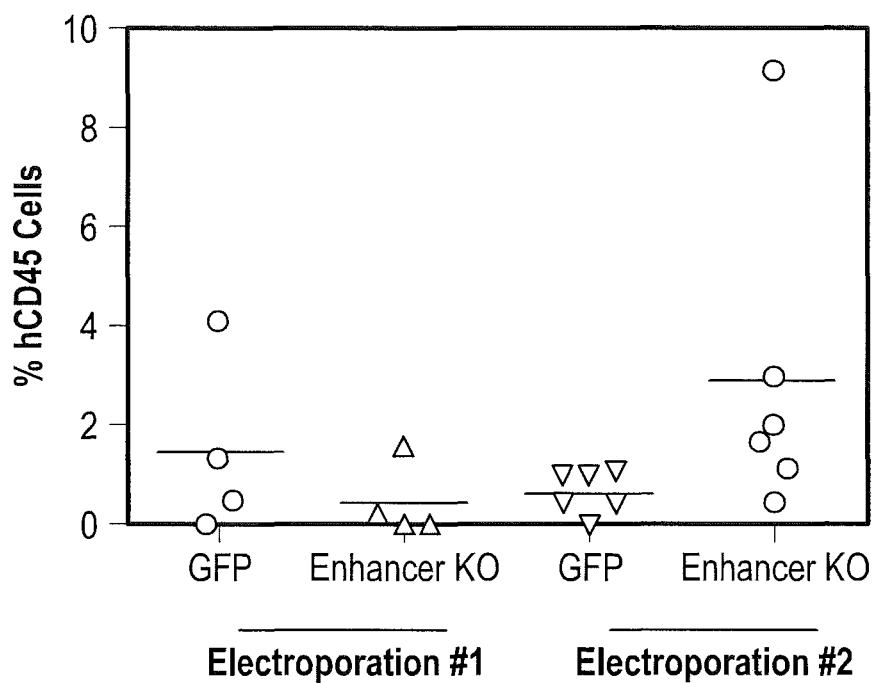
FIGS. 15A and 15B depict the percent of cells of human origin, and targeted genetic modification at the nuclease target site in these human cells, respectively found in the peripheral blood of mice following edited human CD34+ cell transplant.
Figure 15B:
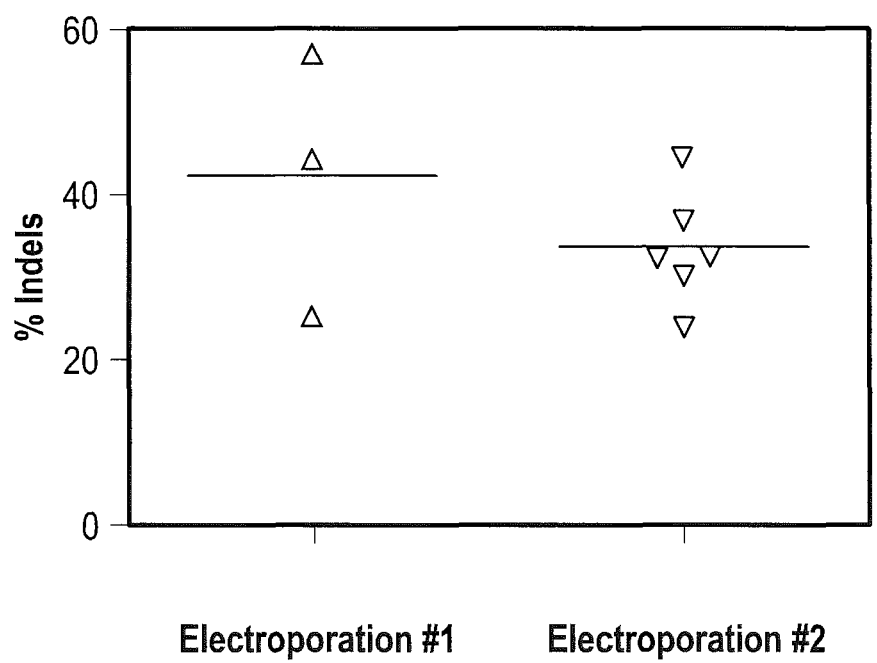
Figure 16A:
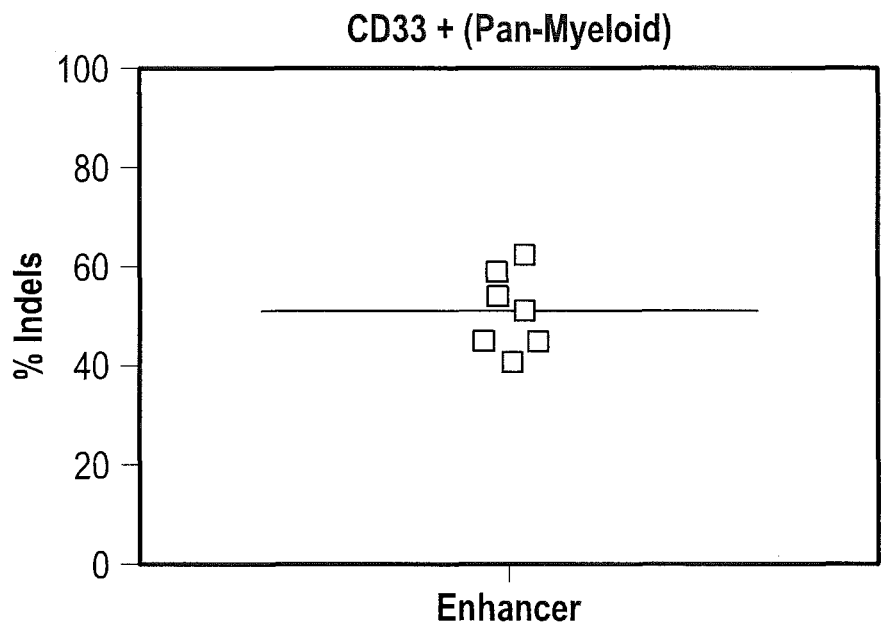
FIGS. 16A through 16D, depict the percentage of indels induced by the nucleases in human cells that differentiated from the original transplanted CD34+ cells 16 weeks post transplantation.
Figure 16B:
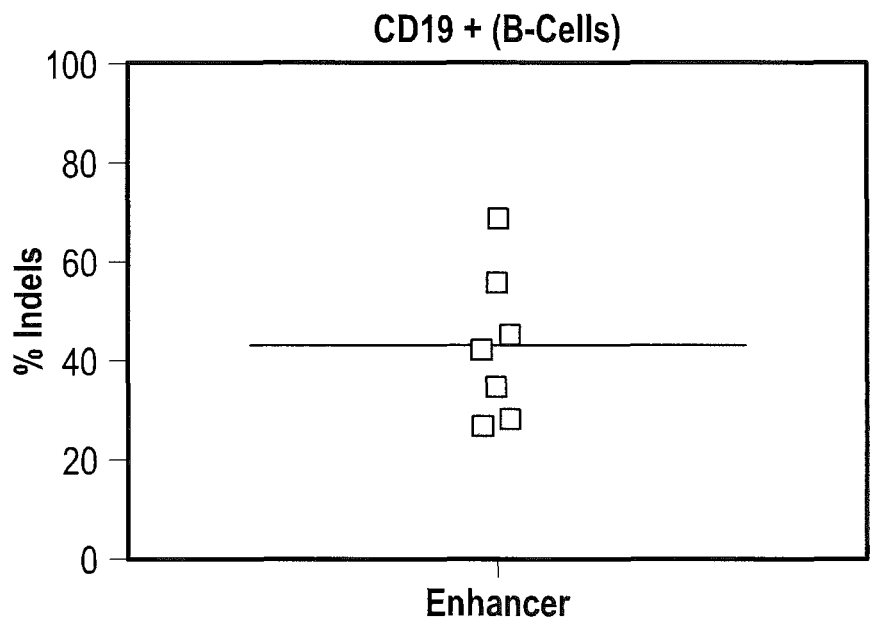
Figure 16C:
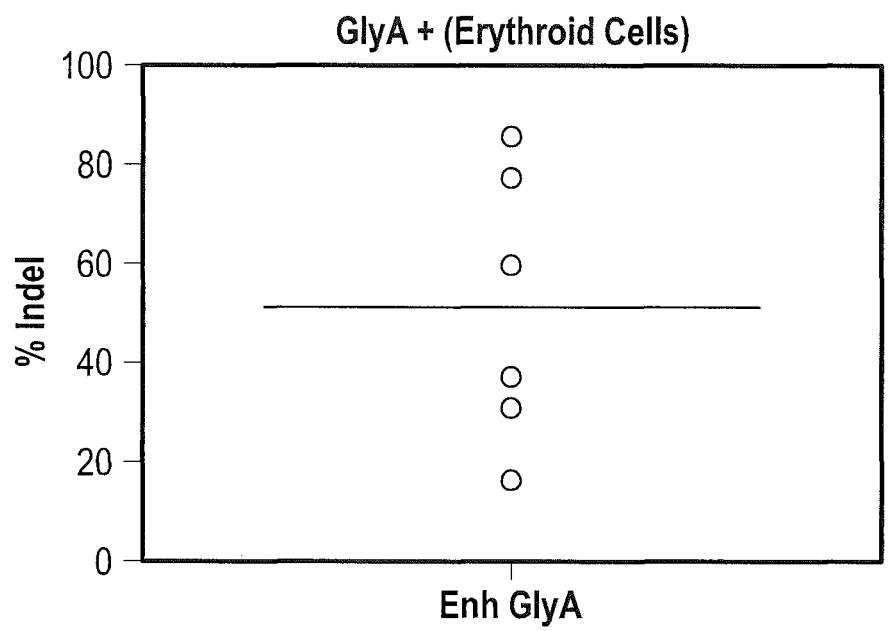
Figure 16D:
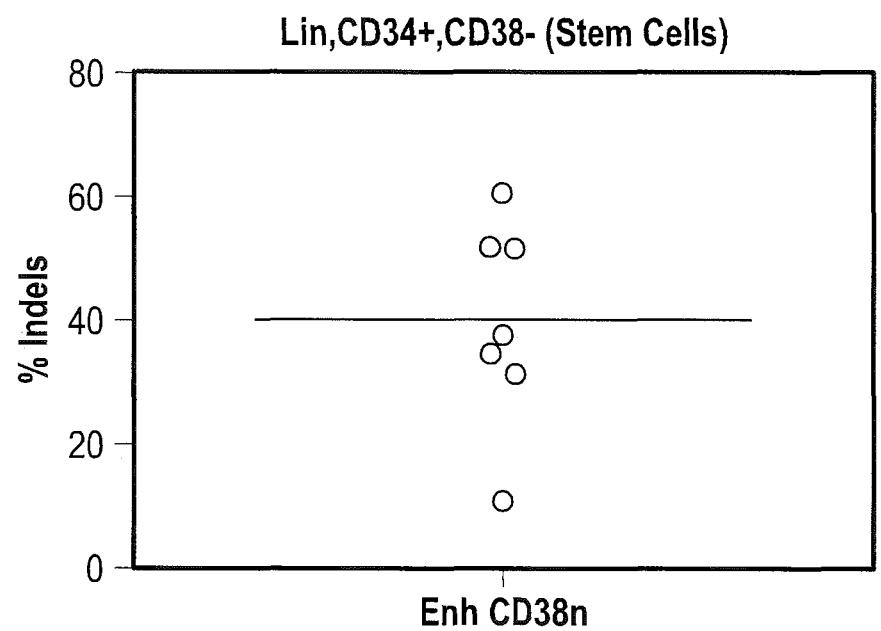

For this experiment, CD34+ cells were electroporated with mRNAs encoding either the 45843/45844 pair (electroporation #1) or the 46801/46880 pair (electroporation #2). In both cases, GFP was used as a control. Following transplantion into the mice, samples were taken at either 4 or 16 weeks post-transplant to observe the level of marking in cells. At week 4, up to approximately 4% of the cells in the peripheral blood were human cells from both electroporations (see FIG. 15A). Genome editing (indels) in these cells was about 30-40% (FIG. 15B).

At week 16 post transplantation, the level of editing was measured in human pan-myeloid, B-cells, erythroid and stem cells in the mice. In these experiments, the cells from both electroporations were pooled. The data (FIG. 16) indicated that 40-50% gene editing was detected in all human cell populations analyzed. This experiment demonstrates that transplanted CD34+ cells are maintained and differentiate while maintaining the gene editing at the BCL11A locus.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An isolated genetically modified human hematopoietic stem or precursor cell comprising
   (i) an endogenous BCL11a enhancer sequence; and
   (ii) a pair of TALENs, each TALEN of the pair comprising a FokI cleavage half-domain and a DNA-binding domain comprising a plurality of TALE repeat units, each repeat unit comprising a hypervariable diresidue region (RVD), wherein the RVDs of the TALE repeats units are shown in a single row of as shown in Table 1, Table 2 or Table 4, and further wherein the pair of TALENs is selected from the group consisting of: 102740 and 102741; 102736 and 102737; 102756 and 102757; 102752 and 102753; 102750 and 102751; 102775 and 102774; 102795 and 102794; 102832 and 102833; 102834 and 102835; 102836 and 102837; 102838 and 102839; 102840 and 102841; 102842 and 102843; 102844 and 102845; 102846 and 102847; 102848 and 102849; 102850 and 102851; 102852 and 102853; 102854 and 102855; 102856 and 102857; 102858 and 102859; 102860 and 102861; 102862 and 102863; 102864 and 102865; 102866 and 102867; 102868 and 102869; 102870 and 102871; 102872 and 102873; 102874 and 102875; 102756 and 102757; 102752 and 102753; 102759 and 102751; 102876 and 102877; 102878 and 102879; 102880 and 102881; 102882 and 102883; 102884 and 102885; 102886 and 102887; 102888 and 102889; 102890 and 102891; 102892 and 102893; 102894 and 102895; 102896 and 102897; 102898 and 102899; 102902 and 102903; 102904 and 102905; 102906 and 102907; 102912 and 102913; 102914 and 102915; 102916 and 102917; 102918 and 102919; 102920 and 102921; or 102922 and 102923, wherein the pair of TALENs cleave and genetically modify the BCL11a enhancer sequence.

2. The cell of claim 1, wherein the hematopoietic stem cell is a CD34+ cell.

3. The cell of claim 1, wherein the TALEN pair is introduced into the cell as a polynucleotide.

4. A pharmaceutical composition comprising the cell of claim 1.

5. A method of treating a human patient in need of an increase in gamma-globin gene or protein expression, the method comprising administering to the patient the pharmaceutical composition of claim 4 in an amount sufficient to increase the gamma-globin gene or protein expression in the human patient.

6. The method of claim 5, wherein the human patient has β-thalassemia.

* * * * *

UNITED STATES PATENT AND TRADEMARK OFFICE
CERTIFICATE OF CORRECTION

PATENT NO. : 11,021,696 B2
APPLICATION NO. : 14/540729
DATED : June 1, 2021
INVENTOR(S) : Orkin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 90 days.

Signed and Sealed this
Seventh Day of February, 2023

Katherine Kelly Vidal
*Director of the United States Patent and Trademark Office*

SEQUENCE LISTING

```
<160> NUMBER OF SEQ ID NOS: 287

<210> SEQ ID NO 1
<211> LENGTH: 366
<212> TYPE: DNA
<213> ORGANISM: Homo sapiens

<400> SEQUENCE: 1
caattctagg aagggaagtg ggtatggggc agcccattgc cttcctggta ccaggatgat      60
gcaatgcttg gaggctgtga gctccccacc ttctcagggc acaccctgtg atcttgtggg     120 accectctgt ccagcccagc ctgggtgtgc atcttgtgtg cttggtcggc actgataggg     180
gtcgcggtag ggagttgtcg gcacacactg ctgcatgtcc tgtgagcggt ccccaaggct     240
gtgcccagcc ttcagtgtcc agggcctctt ctgacaggcc ctgctggtta tcactgttgg     300
cattatctcc acgcaccact tctgtgccca gggctgctgg gtcaccttaa ggagccacac     360
acccgt                                                                366

<210> SEQ ID NO 2
<211> LENGTH: 553
<212> TYPE: DNA
<213> ORGANISM: Homo sapiens

<400> SEQUENCE: 2
gaggtactga tggaccttgg gtgctattcc tgtgataagg aaggcagcta gacaggactt      60
gggagttatc tgtagtgaga tggctgaaaa gcgatacagg gctggctcta tgccccaggt     120
gtgcataagt aagagcagat agctgattcc agtgcaaagt ccatacaggt aataacatag     180
gccagaaaag agatatggca tctactctta gacataacac accagggtca atacaactttt    240 gaagctagtc tagtgcaagc taacagttgc ttttatcaca ggctccagga agggtttggc     300
ctctgattag ggtgggggcg tgggtggggt agaagaggac tggcagacct ctccatcggt     360
ggccgtttgc ccaggggggc ctctttcgga aggctctctt ggtgatggag aattggattt     420
tatttctcaa tgggaatgaa ataatttgta tgccatgccg tgtggactcc caaaattgta     480
aaggaggtga agcttcccct gtctgcactc tcccctcctc ataattgtcc attttcatc     540 tgtcgggctg tcc                                                         553

<210> SEQ ID NO 3
<211> LENGTH: 352
<212> TYPE: DNA
<213> ORGANISM: Homo sapiens

<400> SEQUENCE: 3
cgtttttaga acttagcttt ttgcattgag gatgcgcagg tggctgagac taacttcttt      60
gcagatgacc atggttgaaa gtcagctata gagttgcaca accacgtagt tgggcttcac     120
atatagaaga tgttgtcatt ttttggtaac tctgtcagac tttaccaacc tggcgcacag     180
tctggttggc acataaactt cacatttgct cttctccagg gtgtggggtg gctgtttaaa     240
gagggtggat attcatgcta atctttgtgt agcataacat gttactgcaa cttgcttttt     300
tttttttatc tgaaagttca agtagatatc agaagggaaa tgtttgtggg tg             352
```

```
<210> SEQ ID NO 4
<211> LENGTH: 21
<212> TYPE: DNA
<213> ORGANISM: Homo sapiens

<400> SEQUENCE: 4
gtggagggga taactgggtc a                                             21

<210> SEQ ID NO 5
<211> LENGTH: 21
<212> TYPE: DNA
<213> ORGANISM: Homo sapiens

<400> SEQUENCE: 5
ttgtgtgctt ggtcggcact g                                             21

<210> SEQ ID NO 6
<211> LENGTH: 21
<212> TYPE: DNA
<213> ORGANISM: Homo sapiens

<400> SEQUENCE: 6
gtgccgacaa ctccctaccg c                                             21

<210> SEQ ID NO 7
<211> LENGTH: 21
<212> TYPE: DNA
<213> ORGANISM: Homo sapiens

<400> SEQUENCE: 7
attatttcat tcccattgag a                                             21

<210> SEQ ID NO 8
<211> LENGTH: 21
<212> TYPE: DNA
<213> ORGANISM: Homo sapiens

<400> SEQUENCE: 8
ataggccaga aaagagatat g                                             21

<210> SEQ ID NO 9
<211> LENGTH: 21
<212> TYPE: DNA
<213> ORGANISM: Homo sapiens

<400> SEQUENCE: 9
ctggtgtgtt atgtctaaga g                                             21

<210> SEQ ID NO 10
<211> LENGTH: 21
<212> TYPE: DNA
<213> ORGANISM: Homo sapiens

<400> SEQUENCE: 10
ctagtttata gggggttcta c                                             21

<210> SEQ ID NO 11
<211> LENGTH: 21
<212> TYPE: DNA
<213> ORGANISM: Homo sapiens

<400> SEQUENCE: 11
atagcaccca aggtccatca g                                             21
```

<210> SEQ ID NO 12
<211> LENGTH: 21
<212> TYPE: DNA
<213> ORGANISM: Homo sapiens

<400> SEQUENCE: 12
attcaacaaa tagcatataa a                                              21

<210> SEQ ID NO 13
<211> LENGTH: 21
<212> TYPE: DNA
<213> ORGANISM: Homo sapiens

<400> SEQUENCE: 13
cttccctttt aggaaggtaa a                                              21

<210> SEQ ID NO 14
<211> LENGTH: 21
<212> TYPE: DNA
<213> ORGANISM: Homo sapiens

<400> SEQUENCE: 14
atgccagagg gcagcaaaca t                                              21

<210> SEQ ID NO 15
<211> LENGTH: 21
<212> TYPE: DNA
<213> ORGANISM: Homo sapiens

<400> SEQUENCE: 15
cttaatagct gaaggggggcc a                                             21

<210> SEQ ID NO 16
<211> LENGTH: 21
<212> TYPE: DNA
<213> ORGANISM: Homo sapiens

<400> SEQUENCE: 16
gtgtgcataa gtaagagcag a                                              21

<210> SEQ ID NO 17
<211> LENGTH: 21
<212> TYPE: DNA
<213> ORGANISM: Homo sapiens

<400> SEQUENCE: 17
ctgtatggac tttgcactgg a                                              21

<210> SEQ ID NO 18
<211> LENGTH: 21
<212> TYPE: DNA
<213> ORGANISM: Homo sapiens

<400> SEQUENCE: 18
gtaagagcag atagctgatt c                                              21

<210> SEQ ID NO 19
<211> LENGTH: 21
<212> TYPE: DNA
<213> ORGANISM: Homo sapiens

<400> SEQUENCE: 19

```
atgttattac ctgtatggac t                                              21
```

<210> SEQ ID NO 20
<211> LENGTH: 21
<212> TYPE: DNA
<213> ORGANISM: Homo sapiens

<400> SEQUENCE: 20

```
atagctgatt ccagtgcaaa g                                              21
```

<210> SEQ ID NO 21
<211> LENGTH: 21
<212> TYPE: DNA
<213> ORGANISM: Homo sapiens

<400> SEQUENCE: 21

```
ttttctggcc tatgttatta c                                              21
```

<210> SEQ ID NO 22
<211> LENGTH: 21
<212> TYPE: DNA
<213> ORGANISM: Homo sapiens

<400> SEQUENCE: 22

```
gtgcaaagtc catacaggta a                                              21
```

<210> SEQ ID NO 23
<211> LENGTH: 21
<212> TYPE: DNA
<213> ORGANISM: Homo sapiens

<400> SEQUENCE: 23

```
atgccatatc tcttttctgg c                                              21
```

<210> SEQ ID NO 24
<211> LENGTH: 21
<212> TYPE: DNA
<213> ORGANISM: Homo sapiens

<400> SEQUENCE: 24

```
atacaggtaa taacataggc c                                              21
```

<210> SEQ ID NO 25
<211> LENGTH: 21
<212> TYPE: DNA
<213> ORGANISM: Homo sapiens

<400> SEQUENCE: 25

```
ctaagagtag atgccatatc t                                              21
```

<210> SEQ ID NO 26
<211> LENGTH: 21
<212> TYPE: DNA
<213> ORGANISM: Homo sapiens

<400> SEQUENCE: 26

```
ataacatagg ccagaaaaga g                                              21
```

<210> SEQ ID NO 27
<211> LENGTH: 21
<212> TYPE: DNA
<213> ORGANISM: Homo sapiens

<400> SEQUENCE: 27

```
gtgttatgtc taagagtaga t                                        21

<210> SEQ ID NO 28
<211> LENGTH: 21
<212> TYPE: DNA
<213> ORGANISM: Homo sapiens

<400> SEQUENCE: 28
ctcttagaca taacacacca g                                        21

<210> SEQ ID NO 29
<211> LENGTH: 21
<212> TYPE: DNA
<213> ORGANISM: Homo sapiens

<400> SEQUENCE: 29
ctagactagc ttcaaagttg t                                        21

<210> SEQ ID NO 30
<211> LENGTH: 21
<212> TYPE: DNA
<213> ORGANISM: Homo sapiens

<400> SEQUENCE: 30
ataacacacc agggtcaata c                                        21

<210> SEQ ID NO 31
<211> LENGTH: 21
<212> TYPE: DNA
<213> ORGANISM: Homo sapiens

<400> SEQUENCE: 31
gttagcttgc actagactag c                                        21

<210> SEQ ID NO 32
<211> LENGTH: 21
<212> TYPE: DNA
<213> ORGANISM: Homo sapiens

<400> SEQUENCE: 32
gtcaatacaa ctttgaagct a                                        21

<210> SEQ ID NO 33
<211> LENGTH: 20
<212> TYPE: DNA
<213> ORGANISM: Homo sapiens

<400> SEQUENCE: 33
ataaaagcaa ctgttagctt                                          20

<210> SEQ ID NO 34
<211> LENGTH: 21
<212> TYPE: DNA
<213> ORGANISM: Homo sapiens

<400> SEQUENCE: 34
ttgaagctag tctagtgcaa g                                        21

<210> SEQ ID NO 35
<211> LENGTH: 21
<212> TYPE: DNA
<213> ORGANISM: Homo sapiens
```

<400> SEQUENCE: 35
ctggagcctg tgataaaagc a                                              21

<210> SEQ ID NO 36
<211> LENGTH: 20
<212> TYPE: DNA
<213> ORGANISM: Homo sapiens

<400> SEQUENCE: 36
ctagtctagt gcaagctaac                                                20

<210> SEQ ID NO 37
<211> LENGTH: 21
<212> TYPE: DNA
<213> ORGANISM: Homo sapiens

<400> SEQUENCE: 37
cttcctggag cctgtgataa a                                              21

<210> SEQ ID NO 38
<211> LENGTH: 21
<212> TYPE: DNA
<213> ORGANISM: Homo sapiens

<400> SEQUENCE: 38
gtgcaagcta acagttgctt t                                              21

<210> SEQ ID NO 39
<211> LENGTH: 21
<212> TYPE: DNA
<213> ORGANISM: Homo sapiens

<400> SEQUENCE: 39
atcagaggcc aaacccttcc t                                              21

<210> SEQ ID NO 40
<211> LENGTH: 21
<212> TYPE: DNA
<213> ORGANISM: Homo sapiens

<400> SEQUENCE: 40
ctaacagttg cttttatcac a                                              21

<210> SEQ ID NO 41
<211> LENGTH: 21
<212> TYPE: DNA
<213> ORGANISM: Homo sapiens

<400> SEQUENCE: 41
ctaatcagag gccaaaccct t                                              21

<210> SEQ ID NO 42
<211> LENGTH: 21
<212> TYPE: DNA
<213> ORGANISM: Homo sapiens

<400> SEQUENCE: 42
atcacaggct ccaggaaggg t                                              21

<210> SEQ ID NO 43
<211> LENGTH: 21
<212> TYPE: DNA
<213> ORGANISM: Homo sapiens

```
<400> SEQUENCE: 43 ctacccacc cacgccccca c                                              21

<210> SEQ ID NO 44
<211> LENGTH: 21
<212> TYPE: DNA
<213> ORGANISM: Homo sapiens

<400> SEQUENCE: 44
ctccaggaag ggtttggcct c                                             21

<210> SEQ ID NO 45
<211> LENGTH: 21
<212> TYPE: DNA
<213> ORGANISM: Homo sapiens

<400> SEQUENCE: 45 ctacccacc cacgccccca c                                              21

<210> SEQ ID NO 46
<211> LENGTH: 21
<212> TYPE: DNA
<213> ORGANISM: Homo sapiens

<400> SEQUENCE: 46
ttggcctctg attagggtgg g                                             21

<210> SEQ ID NO 47
<211> LENGTH: 21
<212> TYPE: DNA
<213> ORGANISM: Homo sapiens

<400> SEQUENCE: 47
ctgccagtcc tcttctaccc c                                             21

<210> SEQ ID NO 48
<211> LENGTH: 21
<212> TYPE: DNA
<213> ORGANISM: Homo sapiens

<400> SEQUENCE: 48
attagggtgg gggcgtgggt g                                             21

<210> SEQ ID NO 49
<211> LENGTH: 21
<212> TYPE: DNA
<213> ORGANISM: Homo sapiens

<400> SEQUENCE: 49
atggagaggt ctgccagtcc t                                             21

<210> SEQ ID NO 50
<211> LENGTH: 21
<212> TYPE: DNA
<213> ORGANISM: Homo sapiens

<400> SEQUENCE: 50
gtggggtaga agaggactgg c                                             21

<210> SEQ ID NO 51
<211> LENGTH: 21
<212> TYPE: DNA
```

```
<213> ORGANISM: Homo sapiens

<400> SEQUENCE: 51
ctgggcaaac ggccaccgat g                                              21

<210> SEQ ID NO 52
<211> LENGTH: 21
<212> TYPE: DNA
<213> ORGANISM: Homo sapiens

<400> SEQUENCE: 52
ctggcagacc tctccatcgg t                                              21

<210> SEQ ID NO 53
<211> LENGTH: 21
<212> TYPE: DNA
<213> ORGANISM: Homo sapiens

<400> SEQUENCE: 53
cttccgaaag aggcccccct g                                              21

<210> SEQ ID NO 54
<211> LENGTH: 20
<212> TYPE: DNA
<213> ORGANISM: Homo sapiens

<400> SEQUENCE: 54
atcggtggcc gtttgcccag                                                20

<210> SEQ ID NO 55
<211> LENGTH: 21
<212> TYPE: DNA
<213> ORGANISM: Homo sapiens

<400> SEQUENCE: 55
atcaccaaga gagccttccg a                                              21

<210> SEQ ID NO 56
<211> LENGTH: 21
<212> TYPE: DNA
<213> ORGANISM: Homo sapiens

<400> SEQUENCE: 56
gtttgcccag gggggcctct t                                              21

<210> SEQ ID NO 57
<211> LENGTH: 21
<212> TYPE: DNA
<213> ORGANISM: Homo sapiens

<400> SEQUENCE: 57
attctccatc accaagagag c                                              21

<210> SEQ ID NO 58
<211> LENGTH: 21
<212> TYPE: DNA
<213> ORGANISM: Homo sapiens

<400> SEQUENCE: 58
ttgcccaggg gggcctcttt c                                              21

<210> SEQ ID NO 59
<211> LENGTH: 21
```

```
<212> TYPE: DNA
<213> ORGANISM: Homo sapiens

<400> SEQUENCE: 59
ataaaatcca attctccatc a                                              21

<210> SEQ ID NO 60
<211> LENGTH: 21
<212> TYPE: DNA
<213> ORGANISM: Homo sapiens

<400> SEQUENCE: 60
ctttcggaag gctctcttgg t                                              21

<210> SEQ ID NO 61
<211> LENGTH: 21
<212> TYPE: DNA
<213> ORGANISM: Homo sapiens

<400> SEQUENCE: 61
attgagaaat aaaatccaat t                                              21

<210> SEQ ID NO 62
<211> LENGTH: 21
<212> TYPE: DNA
<213> ORGANISM: Homo sapiens

<400> SEQUENCE: 62
ctcttggtga tggagaattg g                                              21

<210> SEQ ID NO 63
<211> LENGTH: 28
<212> TYPE: DNA
<213> ORGANISM: Homo sapiens

<400> SEQUENCE: 63
atggctgaaa agcgatacag ggctggct                                       28

<210> SEQ ID NO 64
<211> LENGTH: 28
<212> TYPE: DNA
<213> ORGANISM: Homo sapiens

<400> SEQUENCE: 64
tcactacaga taactcccaa gtcctgtc                                       28

<210> SEQ ID NO 65
<211> LENGTH: 28
<212> TYPE: DNA
<213> ORGANISM: Homo sapiens

<400> SEQUENCE: 65
cataagtaag agcagatagc tgattcca                                       28

<210> SEQ ID NO 66
<211> LENGTH: 28
<212> TYPE: DNA
<213> ORGANISM: Homo sapiens

<400> SEQUENCE: 66
cacctggggc atagagccag ccctgtat                                       28

<210> SEQ ID NO 67
```

-continued

```
<211> LENGTH: 28
<212> TYPE: DNA
<213> ORGANISM: Homo sapiens

<400> SEQUENCE: 67
tccatacagg taataacata ggccagaa                                          28

<210> SEQ ID NO 68
<211> LENGTH: 28
<212> TYPE: DNA
<213> ORGANISM: Homo sapiens

<400> SEQUENCE: 68
actttgcact ggaatcagct atctgctc                                          28

<210> SEQ ID NO 69
<211> LENGTH: 28
<212> TYPE: DNA
<213> ORGANISM: Homo sapiens

<400> SEQUENCE: 69
aagtaagagc agatagctga ttccagtg                                          28

<210> SEQ ID NO 70
<211> LENGTH: 28
<212> TYPE: DNA
<213> ORGANISM: Homo sapiens

<400> SEQUENCE: 70
cacacctggg gcatagagcc agccctgt                                          28

<210> SEQ ID NO 71
<211> LENGTH: 28
<212> TYPE: DNA
<213> ORGANISM: Homo sapiens

<400> SEQUENCE: 71
tcacaggctc caggaagggt ttggcctc                                          28

<210> SEQ ID NO 72
<211> LENGTH: 28
<212> TYPE: DNA
<213> ORGANISM: Homo sapiens

<400> SEQUENCE: 72
aagcaactgt tagcttgcac tagactag                                          28

<210> SEQ ID NO 73
<211> LENGTH: 28
<212> TYPE: DNA
<213> ORGANISM: Homo sapiens

<400> SEQUENCE: 73
cacaggctcc aggaagggtt tggcctct                                          28

<210> SEQ ID NO 74
<211> LENGTH: 28
<212> TYPE: DNA
<213> ORGANISM: Homo sapiens

<400> SEQUENCE: 74
aaagcaactg ttagcttgca ctagacta                                          28
```

```
<210> SEQ ID NO 75
<211> LENGTH: 28
<212> TYPE: DNA
<213> ORGANISM: Homo sapiens

<400> SEQUENCE: 75
gtgggggcgt gggtgggta gaagagga                                           28

<210> SEQ ID NO 76
<211> LENGTH: 28
<212> TYPE: DNA
<213> ORGANISM: Homo sapiens

<400> SEQUENCE: 76
ctaatcagag gccaaaccct tcctggag                                          28

<210> SEQ ID NO 77
<211> LENGTH: 28
<212> TYPE: DNA
<213> ORGANISM: Homo sapiens

<400> SEQUENCE: 77
tggccgtttg cccaggggg cctctttc                                           28

<210> SEQ ID NO 78
<211> LENGTH: 28
<212> TYPE: DNA
<213> ORGANISM: Homo sapiens

<400> SEQUENCE: 78
cgatggagag gtctgccagt cctcttct                                          28

<210> SEQ ID NO 79
<211> LENGTH: 28
<212> TYPE: DNA
<213> ORGANISM: Homo sapiens

<400> SEQUENCE: 79
ttgcccaggg gggcctcttt cggaaggc                                          28

<210> SEQ ID NO 80
<211> LENGTH: 28
<212> TYPE: DNA
<213> ORGANISM: Homo sapiens

<400> SEQUENCE: 80
ccaccgatgg agaggtctgc cagtcctc                                          28

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Arg Ser Asp Asn Leu Ser Glu
1               5

<210> SEQ ID NO 82
<211> LENGTH: 7
<212> TYPE: PRT
<213> ORGANISM: Artificial Sequence
<220> FEATURE:
```

<223> OTHER INFORMATION: Description of Artificial Sequence: Synthetic
       peptide

<400> SEQUENCE: 82

Thr Arg Ser Pro Leu Arg Asn
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 83

Arg Ser Asp Asp Leu Thr Arg
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 84

Gln Lys Ser Asn Leu Ser Ser
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 85

Gln Ser Ala His Arg Lys Asn
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 86

Asp Ser Ser His Arg Thr Arg
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 87

Asp Ser Ser Asp Arg Lys Lys
1               5

```
<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Arg Ser Asn Arg Thr Thr
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Thr Asn Ser Asn Arg Lys Arg
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Ser Gly Asp Leu Thr Arg
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Leu Lys Asp Thr Leu Arg Arg
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Tyr Cys Cys Leu Arg Asp
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93
```

```
Thr Ser Gly Asn Leu Thr Arg
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Arg Thr His Leu Lys Ala
1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Ser Gly Ala Leu Ala Arg
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Ser Ala Asn Arg Thr Lys
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Asn Ala His Arg Lys Thr
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Ser Asp His Leu Ser Arg
1               5

<210> SEQ ID NO 99
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 99

Gln Gln Trp Asp Arg Lys Gln
1               5

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Ser Asp Tyr Leu Ser Lys
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Ser Ser Val Arg Thr Thr
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Thr Asn Gln Asn Leu Thr Val
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Thr Ser Gly His Leu Ser Arg
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Ser Ala Asp Leu Thr Arg
1               5
```

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Thr Asn Gln Asn Arg Ile Thr
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Leu Asp Trp Leu Pro Met
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

His Lys Trp Val Leu Arg Gln
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Leu Lys Gln Asn Leu Asp Ala
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Ser Ala His Leu Ser Arg
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 110

Arg Ser Asp Val Leu Ser Thr
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asp Thr Arg Asn Leu Arg Ala
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Leu Arg His His Leu Thr Arg
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Arg Arg Asp Asn Leu His Ser
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Ser Asp His Leu Ser Asn
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Asp Ser Arg Ser Arg Ile Asn
1               5

<210> SEQ ID NO 116
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 116

Asp Arg Ser His Leu Thr Arg
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Ser Gly Thr Arg Lys Thr
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asp Gln Ser Asn Leu Arg Ala
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Pro Tyr Thr Leu Arg Leu
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Thr Gly Tyr Asn Leu Thr Asn
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Thr Ser Gly Ser Leu Thr Arg
1               5
```

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gln His Gln Val Leu Val Arg
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gln Asn Ala Thr Arg Thr Lys
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Thr Ser Gly Ser Leu Ser Arg
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Ser Asp His Leu Thr Gln
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gln Ser Gly His Leu Ala Arg
1               5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 127

Gln Lys Gly Thr Leu Gly Glu
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gln Ser Ser Asp Leu Ser Arg
1               5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Gln Cys Cys Leu Phe His
1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Arg Ser Asp Ala Leu Ala Arg
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gln Ser Asn Asp Leu Ser Asn
1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Arg Ser His His Leu Lys Ala
1               5

<210> SEQ ID NO 133
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Thr Ser Ser Asn Arg Lys Thr
1               5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ala Ser Lys Thr Arg Lys Asn
1               5

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gln Trp Lys Ser Arg Ala Arg
1               5

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asp Arg Ser Ala Leu Ser Arg
1               5

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Arg Ser Asp Val Leu Ser Glu
1               5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Arg Ser Ala Asn Leu Ala Arg
```

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Arg Ser Asp Ala Leu Thr Gln
1               5

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Arg Ser Asp Asn Leu Thr Arg
1               5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gln Ser Gly His Leu Ser Arg
1               5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asp Leu Thr Thr Leu Arg Lys
1               5

<210> SEQ ID NO 143
<211> LENGTH: 21
<212> TYPE: DNA
<213> ORGANISM: Homo sapiens

<400> SEQUENCE: 143
ataatgaatg tcccaggcca a                                                   21

<210> SEQ ID NO 144
<211> LENGTH: 20
<212> TYPE: DNA
<213> ORGANISM: Homo sapiens

<400> SEQUENCE: 144
ctgccccata cccacttccc                                                     20

```
<210> SEQ ID NO 145
<211> LENGTH: 21
<212> TYPE: DNA
<213> ORGANISM: Homo sapiens

<400> SEQUENCE: 145
attctaggaa gggaagtggg t                                        21

<210> SEQ ID NO 146
<211> LENGTH: 21
<212> TYPE: DNA
<213> ORGANISM: Homo sapiens

<400> SEQUENCE: 146
gtaccaggaa ggcaatgggc t                                        21

<210> SEQ ID NO 147
<211> LENGTH: 21
<212> TYPE: DNA
<213> ORGANISM: Homo sapiens

<400> SEQUENCE: 147
gtgggtatgg ggcagcccat t                                        21

<210> SEQ ID NO 148
<211> LENGTH: 20
<212> TYPE: DNA
<213> ORGANISM: Homo sapiens

<400> SEQUENCE: 148
attgcatcat cctggtacca                                          20

<210> SEQ ID NO 149
<211> LENGTH: 21
<212> TYPE: DNA
<213> ORGANISM: Homo sapiens

<400> SEQUENCE: 149
cttcctggta ccaggatgat g                                        21

<210> SEQ ID NO 150
<211> LENGTH: 21
<212> TYPE: DNA
<213> ORGANISM: Homo sapiens

<400> SEQUENCE: 150
gtggggagct cacagcctcc a                                        21

<210> SEQ ID NO 151
<211> LENGTH: 21
<212> TYPE: DNA
<213> ORGANISM: Homo sapiens

<400> SEQUENCE: 151
atgatgcaat gcttggaggc t                                        21

<210> SEQ ID NO 152
<211> LENGTH: 21
<212> TYPE: DNA
<213> ORGANISM: Homo sapiens

<400> SEQUENCE: 152
gtgtgccctg agaaggtggg g                                        21
```

```
<210> SEQ ID NO 153
<211> LENGTH: 21
<212> TYPE: DNA
<213> ORGANISM: Homo sapiens

<400> SEQUENCE: 153
atgcttggag gctgtgagct c                                          21

<210> SEQ ID NO 154
<211> LENGTH: 21
<212> TYPE: DNA
<213> ORGANISM: Homo sapiens

<400> SEQUENCE: 154
atcacaggdt gtgccctgag a                                          21

<210> SEQ ID NO 155
<211> LENGTH: 21
<212> TYPE: DNA
<213> ORGANISM: Homo sapiens

<400> SEQUENCE: 155
ctccccacct tctcagggca c                                          21

<210> SEQ ID NO 156
<211> LENGTH: 21
<212> TYPE: DNA
<213> ORGANISM: Homo sapiens

<400> SEQUENCE: 156
ctggacagag gggtcccaca a                                          21

<210> SEQ ID NO 157
<211> LENGTH: 21
<212> TYPE: DNA
<213> ORGANISM: Homo sapiens

<400> SEQUENCE: 157
cttctcaggg cacccctgt g                                           21

<210> SEQ ID NO 158
<211> LENGTH: 21
<212> TYPE: DNA
<213> ORGANISM: Homo sapiens

<400> SEQUENCE: 158
ctgggctgga cagaggggtc c                                          21

<210> SEQ ID NO 159
<211> LENGTH: 20
<212> TYPE: DNA
<213> ORGANISM: Homo sapiens

<400> SEQUENCE: 159
ctgtgatctt gtgggacccc                                            20

<210> SEQ ID NO 160
<211> LENGTH: 20
<212> TYPE: DNA
<213> ORGANISM: Homo sapiens

<400> SEQUENCE: 160
atgcacaccc aggctgggct                                            20
```

```
<210> SEQ ID NO 161
<211> LENGTH: 21
<212> TYPE: DNA
<213> ORGANISM: Homo sapiens

<400> SEQUENCE: 161
cttgtgggac ccctctgtcc a                                               21

<210> SEQ ID NO 162
<211> LENGTH: 21
<212> TYPE: DNA
<213> ORGANISM: Homo sapiens

<400> SEQUENCE: 162
gtgccgacca agcacacaag a                                               21

<210> SEQ ID NO 163
<211> LENGTH: 21
<212> TYPE: DNA
<213> ORGANISM: Homo sapiens

<400> SEQUENCE: 163
ctgtccagcc cagcctgggt g                                               21

<210> SEQ ID NO 164
<211> LENGTH: 21
<212> TYPE: DNA
<213> ORGANISM: Homo sapiens

<400> SEQUENCE: 164
atcagtgccg accaagcaca c                                               21

<210> SEQ ID NO 165
<211> LENGTH: 21
<212> TYPE: DNA
<213> ORGANISM: Homo sapiens

<400> SEQUENCE: 165
ctgggtgtgc atcttgtgtg c                                               21

<210> SEQ ID NO 166
<211> LENGTH: 21
<212> TYPE: DNA
<213> ORGANISM: Homo sapiens

<400> SEQUENCE: 166
ctaccgcgac ccctatcagt g                                               21

<210> SEQ ID NO 167
<211> LENGTH: 21
<212> TYPE: DNA
<213> ORGANISM: Homo sapiens

<400> SEQUENCE: 167
gtagggagtt gtcggcacac a                                               21

<210> SEQ ID NO 168
<211> LENGTH: 21
<212> TYPE: DNA
<213> ORGANISM: Homo sapiens

<400> SEQUENCE: 168
```
ttggggaccg ctcacaggac a                                              21

<210> SEQ ID NO 169
<211> LENGTH: 20
<212> TYPE: DNA
<213> ORGANISM: Homo sapiens

<400> SEQUENCE: 169
ctgctgcatg tcctgtgagc                                                20

<210> SEQ ID NO 170
<211> LENGTH: 21
<212> TYPE: DNA
<213> ORGANISM: Homo sapiens

<400> SEQUENCE: 170
ctgaaggctg ggcacagcct t                                              21

<210> SEQ ID NO 171
<211> LENGTH: 21
<212> TYPE: DNA
<213> ORGANISM: Homo sapiens

<400> SEQUENCE: 171
gtccccaagg ctgtgcccag c                                              21

<210> SEQ ID NO 172
<211> LENGTH: 21
<212> TYPE: DNA
<213> ORGANISM: Homo sapiens

<400> SEQUENCE: 172
ctgtcagaag aggccctgga c                                              21

<210> SEQ ID NO 173
<211> LENGTH: 21
<212> TYPE: DNA
<213> ORGANISM: Homo sapiens

<400> SEQUENCE: 173
ttctgacagg ccctgctggt t                                              21

<210> SEQ ID NO 174
<211> LENGTH: 21
<212> TYPE: DNA
<213> ORGANISM: Homo sapiens

<400> SEQUENCE: 174
gtggtgcgtg gagataatgc c                                              21

<210> SEQ ID NO 175
<211> LENGTH: 21
<212> TYPE: DNA
<213> ORGANISM: Homo sapiens

<400> SEQUENCE: 175
ctgctggtta tcactgttgg c                                              21

<210> SEQ ID NO 176
<211> LENGTH: 21
<212> TYPE: DNA
<213> ORGANISM: Homo sapiens

<400> SEQUENCE: 176

```
ctgggcacag aagtggtgcg t                                          21
```

<210> SEQ ID NO 177
<211> LENGTH: 21
<212> TYPE: DNA
<213> ORGANISM: Homo sapiens

<400> SEQUENCE: 177

```
ttggcattat ctccacgcac c                                          21
```

<210> SEQ ID NO 178
<211> LENGTH: 21
<212> TYPE: DNA
<213> ORGANISM: Homo sapiens

<400> SEQUENCE: 178

```
gtgacccagc agccctgggc a                                          21
```

<210> SEQ ID NO 179
<211> LENGTH: 21
<212> TYPE: DNA
<213> ORGANISM: Homo sapiens

<400> SEQUENCE: 179

```
atctccacgc accacttctg t                                          21
```

<210> SEQ ID NO 180
<211> LENGTH: 21
<212> TYPE: DNA
<213> ORGANISM: Homo sapiens

<400> SEQUENCE: 180

```
ctccttaagg tgacccagca g                                          21
```

<210> SEQ ID NO 181
<211> LENGTH: 21
<212> TYPE: DNA
<213> ORGANISM: Homo sapiens

<400> SEQUENCE: 181

```
gtgcccaggg ctgctgggtc a                                          21
```

<210> SEQ ID NO 182
<211> LENGTH: 21
<212> TYPE: DNA
<213> ORGANISM: Homo sapiens

<400> SEQUENCE: 182

```
ctatgtagac gggtgtgtgg c                                          21
```

<210> SEQ ID NO 183
<211> LENGTH: 21
<212> TYPE: DNA
<213> ORGANISM: Homo sapiens

<400> SEQUENCE: 183

```
gtcaccttaa ggagccacac a                                          21
```

<210> SEQ ID NO 184
<211> LENGTH: 21
<212> TYPE: DNA
<213> ORGANISM: Homo sapiens

<400> SEQUENCE: 184
gtcagacccc aagcaggaag g                                              21

<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ala Ala Cys Asn Arg Asn Ala
1               5

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Trp Lys Cys Gln Leu Pro Ile
1               5

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Asp Arg Ser Asn Leu Thr Arg
1               5

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Arg Ser Asp His Leu Ser Gln
1               5

<210> SEQ ID NO 189
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Asp Ser Ser Thr Arg Lys Lys
1               5

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Arg Lys Tyr Tyr Leu Ala Lys
1               5

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Arg Ser Asp Asn Leu Ser Val
1               5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gln Ser Gly Asn Leu Ala Arg
1               5

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ala Arg Trp Ser Leu Gly Lys
1               5

<210> SEQ ID NO 194
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Arg Gln Glu His Arg Val Ala
1               5

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Arg Ser Asp Ser Leu Ser Ala
1               5

<210> SEQ ID NO 196
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Asp Asn Ser Asn Arg Ile Lys
1               5

<210> SEQ ID NO 197
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ser Pro Ser Ser Arg Arg Thr
1               5

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Arg Ser Asp Asn Leu Ala Arg
1               5

<210> SEQ ID NO 199
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Trp Gln Ser Ser Leu Ile Val
1               5

<210> SEQ ID NO 200
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Leu Lys Trp Asn Leu Arg Thr
1               5

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 201

Pro Cys Arg Tyr Arg Leu Asp
1               5

<210> SEQ ID NO 202
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Arg Ser Ala Asn Leu Thr Arg
1               5

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gln Lys Pro Trp Arg Thr Pro
1               5

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gln Ser Ser His Leu Thr Arg
1               5

<210> SEQ ID NO 205
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Tyr Arg Ser Ser Leu Lys Glu
1               5

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Arg Ser Asp Thr Leu Ser Ala
1               5

<210> SEQ ID NO 207
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 207

Asp Lys Ser Thr Arg Thr Lys
1               5

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Asp Arg Ser Ala Leu Ala Arg
1               5

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gln Gly Ala His Leu Gly Ala
1               5

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gln Ser Ser Asp Leu Thr Arg
1               5

<210> SEQ ID NO 211
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Arg Ser Asp Ser Leu Leu Arg
1               5

<210> SEQ ID NO 212
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ser Ala Ser Ala Arg Trp Trp
1               5
```

```
<210> SEQ ID NO 213
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Thr Gln Ser Asn Leu Arg Met
1               5

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Arg Asn Ala Ser Arg Thr Arg
1               5

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Arg Arg Ser Asp Leu Lys Arg
1               5

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Arg Ser Asp Asn Leu Ser Thr
1               5

<210> SEQ ID NO 217
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Asp Asn Ser Asn Arg Ile Asn
1               5

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 218

Gln Ser Gly Asn Leu His Val
1               5

<210> SEQ ID NO 219
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Asp Arg Ser Asp Leu Ser Arg
1               5

<210> SEQ ID NO 220
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Asp Ser Ser Thr Arg Arg Arg
1               5

<210> SEQ ID NO 221
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Asp Arg Ser His Leu Ser Arg
1               5

<210> SEQ ID NO 222
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gln Ala Gly His Leu Ala Lys
1               5

<210> SEQ ID NO 223
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Arg Ser Asp Ser Leu Ser Val
1               5

<210> SEQ ID NO 224
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Thr Ser His Asn Arg Asn Ala
1               5

<210> SEQ ID NO 225
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Asp Arg Ser Asn Leu Ser Ser
1               5

<210> SEQ ID NO 226
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Arg Ser His Ser Leu Leu Arg
1               5

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Asp Asn Arg Asp Arg Ile Lys
1               5

<210> SEQ ID NO 228
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ala Ser Lys Thr Arg Thr Asn
1               5

<210> SEQ ID NO 229
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Tyr Ser Ser Thr Arg Asn Ser
```

```
<210> SEQ ID NO 230
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Gln Ser Thr Pro Arg Asn Thr
1               5

<210> SEQ ID NO 231
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Trp Pro Asp Tyr Leu Pro Thr
1               5

<210> SEQ ID NO 232
<211> LENGTH: 28
<212> TYPE: DNA
<213> ORGANISM: Homo sapiens

<400> SEQUENCE: 232
tggcctggga cattcattat ttagccac                                          28

<210> SEQ ID NO 233
<211> LENGTH: 28
<212> TYPE: DNA
<213> ORGANISM: Homo sapiens

<400> SEQUENCE: 233
tctaggaagg gaagtgggta tggggcag                                          28

<210> SEQ ID NO 234
<211> LENGTH: 28
<212> TYPE: DNA
<213> ORGANISM: Homo sapiens

<400> SEQUENCE: 234
tagaattggc ctgggacatt cattattt                                          28

<210> SEQ ID NO 235
<211> LENGTH: 28
<212> TYPE: DNA
<213> ORGANISM: Homo sapiens

<400> SEQUENCE: 235
gaagggaagt gggtatgggg cagcccat                                          28

<210> SEQ ID NO 236
<211> LENGTH: 28
<212> TYPE: DNA
<213> ORGANISM: Homo sapiens

<400> SEQUENCE: 236
tcatcctggt accaggaagg caatgggc                                          28
```

<210> SEQ ID NO 237
<211> LENGTH: 28
<212> TYPE: DNA
<213> ORGANISM: Homo sapiens

<400> SEQUENCE: 237
gcaatgcttg gaggctgtga gctcccca                                28

<210> SEQ ID NO 238
<211> LENGTH: 28
<212> TYPE: DNA
<213> ORGANISM: Homo sapiens

<400> SEQUENCE: 238
cctgagaagg tggggagctc acagcctc                                28

<210> SEQ ID NO 239
<211> LENGTH: 28
<212> TYPE: DNA
<213> ORGANISM: Homo sapiens

<400> SEQUENCE: 239
acaccctgtg atcttgtggg acccctct                                28

<210> SEQ ID NO 240
<211> LENGTH: 28
<212> TYPE: DNA
<213> ORGANISM: Homo sapiens

<400> SEQUENCE: 240
gggctggaca gagggtccc acaagatc                                 28

<210> SEQ ID NO 241
<211> LENGTH: 28
<212> TYPE: DNA
<213> ORGANISM: Homo sapiens

<400> SEQUENCE: 241
gcctgggtgt gcatcttgtg tgcttggt                                28

<210> SEQ ID NO 242
<211> LENGTH: 28
<212> TYPE: DNA
<213> ORGANISM: Homo sapiens

<400> SEQUENCE: 242
caggctgggc tggacagagg ggtcccac                                28

<210> SEQ ID NO 243
<211> LENGTH: 28
<212> TYPE: DNA
<213> ORGANISM: Homo sapiens

<400> SEQUENCE: 243
gtgtgcatct tgtgtgcttg gtcggcac                                28

<210> SEQ ID NO 244
<211> LENGTH: 28
<212> TYPE: DNA
<213> ORGANISM: Homo sapiens

<400> SEQUENCE: 244
gtgccgacca agcacacaag atgcacac                                    28

<210> SEQ ID NO 245
<211> LENGTH: 28
<212> TYPE: DNA
<213> ORGANISM: Homo sapiens

<400> SEQUENCE: 245 atagggtcg cggtagggag ttgtcggc                                     28

<210> SEQ ID NO 246
<211> LENGTH: 28
<212> TYPE: DNA
<213> ORGANISM: Homo sapiens

<400> SEQUENCE: 246
cctatcagtg ccgaccaagc acacaaga                                    28

<210> SEQ ID NO 247
<211> LENGTH: 28
<212> TYPE: DNA
<213> ORGANISM: Homo sapiens

<400> SEQUENCE: 247
tcgcggtagg gagttgtcgg cacacact                                    28

<210> SEQ ID NO 248
<211> LENGTH: 28
<212> TYPE: DNA
<213> ORGANISM: Homo sapiens

<400> SEQUENCE: 248
ctcacaggac atgcagcagt gtgtgccg                                    28

<210> SEQ ID NO 249
<211> LENGTH: 28
<212> TYPE: DNA
<213> ORGANISM: Homo sapiens

<400> SEQUENCE: 249
tccccaaggc tgtgcccagc cttcagtg                                    28

<210> SEQ ID NO 250
<211> LENGTH: 28
<212> TYPE: DNA
<213> ORGANISM: Homo sapiens

<400> SEQUENCE: 250
gtgtggctcc ttaaggtgac ccagcagc                                    28

<210> SEQ ID NO 251
<211> LENGTH: 28
<212> TYPE: DNA
<213> ORGANISM: Homo sapiens

<400> SEQUENCE: 251
ccgtctacat agaggccctt cctgcttg                                    28

<210> SEQ ID NO 252
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 252

Gln Ser Gly Ser Leu Thr Arg
1               5

<210> SEQ ID NO 253
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ser Gly Tyr Asn Leu Glu Asn
1               5

<210> SEQ ID NO 254
<211> LENGTH: 494
<212> TYPE: DNA
<213> ORGANISM: Homo sapiens

<400> SEQUENCE: 254
tatttgctat taaaatttga aaaacaaatg caggtgccag aggtggctaa ataatgaatg      60
tcccaggcca attctaggaa gggaagtggg tatggggcag cccattgcct tcctggtacc     120
aggatgatgc aatgcttgga ggctgtgagc tccccacctt ctcagggcac accctgtgat     180
cttgtgggac ccctctgtcc agcccagcct gggtgtgcat cttgtgtgct tggtcggcac     240 tgatagggt cgcggtaggg agttgtcggc acacactgct gcatgtcctg tgagcggtcc      300
ccaaggctgt gcccagcctt cagtgtccag ggcctcttct gacaggccct gctggttatc     360
actgttggca ttatctccac gcaccacttc tgtgcccagg gctgctgggt caccttaagg     420
agccacacac ccgtctacat agaggccctt cctgcttggg gtctgaccca gttatcccct     480
ccacacctcc attc                                                      494

<210> SEQ ID NO 255
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
agtctagtgc aagctaacag ttgcttttat cacaggctcc aggaagggtt tggcctctg       59

<210> SEQ ID NO 256
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Gly Ser Gln Leu Val Lys Ser Glu Leu Glu Glu Lys
1               5                   10

<210> SEQ ID NO 257
<211> LENGTH: 36
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(36)

<400> SEQUENCE: 257 gga tcc cag ctg gtg aag agc gag ctg gag gag aag              36
Gly Ser Gln Leu Val Lys Ser Glu Leu Glu Glu Lys
1               5                   10

<210> SEQ ID NO 258
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gly Ser Gln Leu Val Lys Ser Lys Ser Glu Ala Ala Ala Arg Glu Leu
1               5                   10                  15

Glu Glu Lys

<210> SEQ ID NO 259
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(57)

<400> SEQUENCE: 259 gga tcc cag ctg gtg aag agc aag agc gag gcc gct gcc cgc gag ctg       48
Gly Ser Gln Leu Val Lys Ser Lys Ser Glu Ala Ala Ala Arg Glu Leu
1               5                   10                  15 gag gag aag                                                           57
Glu Glu Lys <210> SEQ ID NO 260
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Gly Ser Ile Ser Arg Ala Arg Pro Leu Asn Pro His Pro Glu Leu Glu
1               5                   10                  15

Glu Lys

<210> SEQ ID NO 261
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(54)

<400> SEQUENCE: 261
```

```
gga tcc atc agc aga gcc aga cca ctg aac ccg cac ccg gag ctg gag    48
Gly Ser Ile Ser Arg Ala Arg Pro Leu Asn Pro His Pro Glu Leu Glu
1               5                   10                  15 gag aag                                                             54
Glu Lys

<210> SEQ ID NO 262
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Gly Ser Tyr Ala Pro Met Pro Pro Leu Ala Leu Ala Ser Pro Glu Leu
1               5                   10                  15

Glu Glu Lys

<210> SEQ ID NO 263
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(57)

<400> SEQUENCE: 263 gga tcc tac gct cca atg cca ccc ctg gct ctg gct tcc cca gag ctg    48
Gly Ser Tyr Ala Pro Met Pro Pro Leu Ala Leu Ala Ser Pro Glu Leu
1               5                   10                  15 gag gag aag                                                         57
Glu Glu Lys <210> SEQ ID NO 264
<211> LENGTH: 677
<212> TYPE: DNA
<213> ORGANISM: Homo sapiens

<400> SEQUENCE: 264
cacaacaggc agagaatgtc tgcaccccac cctggaaaac agcctgactg tgccccatgg     60
gcaaaccaga ctagtttata gggggttcta ctctgaggta ctgatggacc ttgggtgcta   120
ttcctgtgat aaggaaggca gctagacagg acttgggagt tatctgtagt gagatggctg   180
aaaagcgata cagggctggc tctatgcccc aggtgtgcat aagtaagagc agatagctga   240
ttccagtgca aagtccatac aggtaataac ataggccaga aaagagatat ggcatctact   300
cttagacata acacaccagg gtcaatacaa cttttgaagct agtctagtgc aagctaacag   360
ttgcttttat cacaggctcc aggaagggtt tggcctctga ttagggtggg ggcgtgggtg   420
gggtagaaga ggactggcag acctctccat cggtggccgt ttgcccaggg gggcctcttt   480
cggaaggctc tcttggtgat ggagaattgg atttttattc tcaatgggaa tgaaataatt   540
tgtatgccat gccgtgtgga ctcccaaaat tgtaaaggag gtgaagcttc ccctgtctgc   600
actctcccct cctcataatt gtccattttt catctgtcgg gctgtccacc catccatcac   660
atataggcac ctatcag                                                  677

<210> SEQ ID NO 265
```

```
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Leu Arg Gly Ser Gln Phe Val Ile Pro Asn Arg Gly Val Thr Lys Gln
1               5                   10                  15

Leu Val Lys Ser Glu Leu Glu Glu Lys Lys Ser Glu Leu
            20                  25

<210> SEQ ID NO 266
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Leu Arg Gly Ser Val Ile Pro Asn Arg Gly Val Thr Lys Gln Leu Val
1               5                   10                  15

Lys Ser Glu Leu Glu Glu Lys Lys Ser Glu Leu
            20                  25

<210> SEQ ID NO 267
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Leu Arg Gly Ser Pro Asn Arg Gly Val Thr Lys Gln Leu Val Lys Ser
1               5                   10                  15

Glu Leu Glu Glu Lys Lys Ser Glu Leu
            20                  25

<210> SEQ ID NO 268
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Leu Arg Gly Ser Arg Gly Val Thr Lys Gln Leu Val Lys Ser Glu Leu
1               5                   10                  15

Glu Glu Lys Lys Ser Glu Leu
            20

<210> SEQ ID NO 269
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Leu Arg Gly Ser Val Thr Lys Gln Leu Val Lys Ser Glu Leu Glu Glu
1               5                   10                  15
```

```
Lys Lys Ser Glu Leu
        20

<210> SEQ ID NO 270
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Leu Arg Gly Ser Gln Leu Val Lys Ser Lys Ser Glu Ala Ala Ala Arg
1               5                   10                  15

Glu Leu Glu Glu Lys Lys Ser Glu Leu
            20                  25

<210> SEQ ID NO 271
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Leu Arg Gly Ser Tyr Ala Pro Met Pro Pro Leu Ala Leu Ala Ser Pro
1               5                   10                  15

Glu Leu Glu Glu Lys Lys Ser Glu Leu
            20                  25

<210> SEQ ID NO 272
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Leu Arg Gly Ser Ile Ser Arg Ala Arg Pro Leu Asn Pro His Pro Glu
1               5                   10                  15

Leu Glu Glu Lys Lys Ser Glu Leu
            20

<210> SEQ ID NO 273
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Leu Arg Gly Ser Gln Leu Val Lys Ser Glu Leu Glu Glu Lys Lys Ser
1               5                   10                  15

Glu Leu

<210> SEQ ID NO 274
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 274

Leu Arg Gly Ser Leu Val Lys Ser Glu Leu Glu Glu Lys Lys Ser Glu
1               5                   10                  15
Leu

<210> SEQ ID NO 275
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Leu Arg Gly Ser Val Lys Ser Glu Leu Glu Glu Lys Lys Ser Glu Leu
1               5                   10                  15

<210> SEQ ID NO 276
<211> LENGTH: 21
<212> TYPE: DNA
<213> ORGANISM: Homo sapiens

<400> SEQUENCE: 276
ctacatagag gcccttcctg c                                          21

<210> SEQ ID NO 277
<211> LENGTH: 78
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 277
acacaccagg gtcaatacaa ctttgaagct agtctagtgc aagctaacag ttgcttttat    60
cacaggctcc aggaaggg                                                  78

<210> SEQ ID NO 278
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
acacaccagg gtcaatacaa ctttgaagct agtctagtga aagctaacag gctcaaggaa    60
gg                                                                   62

<210> SEQ ID NO 279
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
acacaccagg gtcaatacaa ctttgaagct agtctagtgc aagctaacag ttgctccagg    60
aagg                                                                 64

<210> SEQ ID NO 280

```
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
acacaccagg gtcaatacaa ctttgaagct agtctagtgc aagctaacag ttgctttatc    60
acaggctccg ggaagg                                                   76

<210> SEQ ID NO 281
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
acacaccagg gtcaatacaa ctttggagct agtctagtgc aagctaacag ttgcccacag    60
gctccaggaa gg                                                       72

<210> SEQ ID NO 282
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
acacaccagg gtcaatacaa ctttgaagct agtctagtgc aagctaacag ttgcttttat    60
cacaggctcc aggaagg                                                  77

<210> SEQ ID NO 283
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
acacaccagg gtcaatacaa ctttgaagct agtctagtgc aagctaccag ttgcttttat    60
ccaggaagg                                                           69

<210> SEQ ID NO 284
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
acacaccagg gtcaatacaa ctttgaagct agtctagtgc aagctaccag ttgctccagg    60
aagg                                                                64

<210> SEQ ID NO 285
<211> LENGTH: 75
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 285
acacaccagg gtcaatacaa ctttgaagct agtctagtgc aagctaacag ttgctttcat    60
caggctccag gaagg                                                    75

<210> SEQ ID NO 286
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
acacaccagg gtcaatacaa ctttgaagct agtctagtgc aagctaacag ttgcttttgt    60
ccaggctcca ggaagg                                                   76

<210> SEQ ID NO 287
<211> LENGTH: 9
<212> TYPE: PRT
<213> ORGANISM: Unknown
<220> FEATURE:
<223> OTHER INFORMATION: Description of Unknown:
      cleavage site

<400> SEQUENCE: 287

Leu Ala Gly Leu Ile Asp Ala Asp Gly
1               5
```